US006949378B1

(12) United States Patent
Hekimi et al.

(10) Patent No.: US 6,949,378 B1
(45) Date of Patent: Sep. 27, 2005

(54) C. ELEGANS GRO-1 GENE

(75) Inventors: Siegfried Hekimi, Montreal (CA); Bernard Lakowski, Munich (DE); Thomas Barnes, Boston, MA (US); Jason Lemieux, Toronto (CA)

(73) Assignee: McGill University, Montreal (CA)

( * ) Notice: Subject to any disclaimer, the term of this patent is extended or adjusted under 35 U.S.C. 154(b) by 0 days.

(21) Appl. No.: 09/513,151

(22) Filed: Feb. 25, 2000

Related U.S. Application Data

(63) Continuation-in-part of application No. PCT/CA98/00803, filed on Aug. 20, 1998.

(30) Foreign Application Priority Data

Aug. 25, 1997 (CA) .............................................. 2210251

(51) Int. Cl.[7] .............................. C12N 5/10; C07H 21/04
(52) U.S. Cl. ................. 435/320.1; 435/325; 435/252.3; 435/254.11; 536/23.5; 536/24.5
(58) Field of Search .............................. 435/320.1, 325, 435/252.3, 254.11; 536/23.5, 24.5, 23.1

(56) References Cited

PUBLICATIONS

Verma et al Nature, 1997, vol. 389, pp. 239–242.*
Eck et al, Gene–Based Therapy, In: The Pharmacological Basis of Therapeutics, Goodman and Gilman, Ed.s, 1996, pp. 77–101.*
Orkin et al "Report and Recommendation of the Panel to Assess the NIH Investment in Research on Gene Therapy", NIH, 1995).*
Houdebine, Journal of Biotechnology, 1994, vol. 34, pp. 269–287.*
(Alberts p. 585, Molecular Biology of the Cell, 1989).*
Smerdon et al, In: DNA Damage and Repair (monograph), vol. II, pp. 210–212.*
Ushijima et al (1997, PNAS, vol. 94, pp. 2284–2289.*
Jones et al (PNAS, 1997, vol. 94, pp. 2103–2105.*
Hudson (Accession No. G24438, May 31, 1996).*
Accession No. BM721352, Mar. 2, 2002.*
Bork, Nature Genetics, 1998, vol. 18, pp. 313–318.*
Alberts et al, Molecular Boilogy of the Cell, (textbook), 1989, pp. 902.*
Bowie et al "Deciphering the Message in protein Sequences: Tolerance to Amino Acid substitutions" Science, vol. 247, pp. 1306–1310, 1990.*
Lasar et al, "Transforming Growth Factor Alpha: Mutation of Aspartic Acid 47 and Leuine 48 Results in Different Biological Activities", Molecular and Cellular Biology, vol. 8, pp. 1247–1252, 1988.*

Burgess et al "Possible Dissociation of the Heparin–binding and Mitogenic Activies of Heparin–binding Growth Factor–1 from its Receptor–binding Activities by Site–directed Mutagenesis of a single Lysine Residue", Journal of Cellular biology, vol. 111, pp, 1990.*
P. Bork, "Powers and pitsfalls in sequence analysis", Genome Research, vol. 10, pp. 398–400, 2000.*
Friedburg et al, Ed., DNA Repair and Mutagenesis (Monograph), p. 94, 1995.*
PubMed Accession No. D83702, Oct. 1998.*
Fu et al, "Translational regulation of human p53 gene expression", EMBO, vol. 15, pp. 4392–4401, 1996.*
Alberts et al, Ed., Molecular Biology of the Cell (textbook), 3rd edition, p. 465, 1994.*
Shantz and Pegg, "Translational regulation of ornithine decarboxylase and other enzymes", International J of Biochemistry and Cell Biology, vol. 31, pp. 107–122, 1999.*
McClean and Hill, "Evidence of post–translational regulation of p–glycoprotein", European J. of Cancer, vol. 29A, pp. 2243–2248, 1993.*
Benko et al., "Competition between a sterol biosynthetic enzyme and tRNA modification in addition to changes in the protein synthesis machinery causes altered nonsense suppression" PNAS, Jan. 4, 2000, vol. 97. No. 1, 61–66.
Wilson, R. et al. "2.2 MB of contiguous nucleotide sequence from chromosome III of *C. elegans*", Nature, vol. 368, No. 6466, Mar. 3, 1994, pp. 32–28, XP002029739.
Database EMBL EMINV Entry CEC34E10, Acc. No. U10402, Jun. 30, 1994 Wilson, R. et al., *Caenorhabditis elegans* cosmid C34E10' XP002089545.
Database EMBL—CEZC395 Entry CEZC395, Acc. No. U13642, Nov. 30, 1994 Wilson, R. et al.: "*Caenorhabditis elegans* cosmid ZC395" XP002089006.
Adams, M. D. et al., "Initial assessment of human gene diversity cDNA sequence" Nature, vol. 377 (6547 Suppl), Sep. 28, 1995, pp. 3–174 XP002042918.
Database EMBL—EMEST14 Entry HSZZ37212, Acc. No. AA332152, Apr. 18, 1997, Adams, M. D. et al.: "EST36068 Embryo, 8 week I *Homo sapiens* cDNA 5' end similar to similar to tRNA isopentenyltransferase" XP002089546.
Database EMBL—EMEST14 Entry HSZZ61218, Acc. No. AA356092, Apr. 18, 1997 Adams, M. D. et al.: EST64588 Jurkat T–cells VI *Homo sapiens* cDNA 5' end similar to similar to tRNA isopentenyltransferase. XP002089547.
Stern et al., 1993, "The human GRB2 and *Drosophilia* Drk genes can functionally replace the *Caenorhabditis elegans* cell signaling gene sem–5" *Mol. Biol. Cell* 4:1175–88.
Levitan et al., 1996, "Assessment of normal and mutant human presenilin function in *Caenorhabditis elegans*" *PNAS* 93:14940–4.

(Continued)

*Primary Examiner*—Karen A. Canella
(74) *Attorney, Agent, or Firm*—Jones Day

(57) ABSTRACT

The invention relates to the identification of gro-1 gene and to demonstrate that the gro-1 gene is involved in the control of a central physiological clock. Also disclosed are four other genes located within the same operon as the gro-1 gene.

8 Claims, 32 Drawing Sheets

OTHER PUBLICATIONS

Rugarli, E.I. et al., The Kallman syndrome gene homolog in *C. elegans* is involved in epidermal morphogenesis and neurite branching, Development 129:pp.1283–1294, 2002.

Gengyo–Ando K., et al., A Murine Neutral–Specific Homolog Corrects Cholinergic Defects in *Caenorhabditis elegans* unc–18 Mutants, Journal of Neuroscience, 16(21):pp.6695–6702, Nov. 1, 1996.

Antoshechkin, I and Han M., The *C. elegans* evl–20 Gene is a Homolog of the Small GTPase ARL2 and Regulates Cytoskeleton Dynamics during Cytokinesis and Morphogenesis, Developmental Cell, 2:pp.579–591, May 2002

Baumeister, R. et al., Human presenilin–1, but not familial Alzheimer's disease (FAD) mutants, facilitate *Caenorhabditis elegans* Notch signalling independently of proteolytic processing, Genes Funct, 1(2):pp. 149–59, Apr. 1997.

Westmoreland, J.J. et al., Conserved Function of *Caenorhabditis elegans* UNC–30 and Mouse Pitx2 in Controlling GABergic Neuron Differentiation, The Journal of Neuroscience, 21(17):pp.6810–6819, Sep. 2001.

Zhang, J. et al., Evolutionary Conservation of MyoD Function and Differential Utilization of E Proteins, Developmental Biology, 208:pp. 465–472, 1999.

Takahashi, M. et al., Mouse coq7/clk–1 Orthologue Rescued Slowed Rhythmic Behavior and Extended Life Span of clk–1 Longevity Mutant in *Caenorhabditis elegans*, Biochemical and Biophysical Research Communications, 286:pp.534–540, 2001.

Vaux D.L. et al., Prevention of programmed cell death cell death in *Caenorhabditis elegans* by human bcl–2, Science, 258(5090):pp.1955–1957, Dec. 18, 1992.

Laible, G. et al., Mammalian homologues of the Polycomb–group gene Enhancer of zeste mediate gene silencing in *Drosophila heterochromatin* and at *S. cerevisiae telomeres*, The EMBO Journal, 16(11):pp.3219–3232, 1997.

Hudson, J.B. et al., The *Drosophila Medea* gene is required downstream of dpp and enclodes a functional homolog of human Smad4, Development 125,pp.1407–1420, 1998.

Wang, J. et al., Mouse Homolog of the *Drosophila Pc–G* Gene esc Exerts a Dominant Negative Effect in *Drosophila*, Genesis, 26:pp.67–76 , 2000.

Li, X. et al., Isolation and characterization of the putative nuclear modifier gene MTO1 involved in the pathogenesis of deafness–associated mitochondrial 12S rRNA A1555G mutation, Journal of Biological Chemistry Papers in Press, Manuscript—M203267200, Published May 14, 2002.

Lindsey, L.A. et al., Functional Conservation of the Human Homolog of the Yeast Pre–mRNA Splicing Factor Prp17p, The Journal of Biological Chemistry, 273(49):pp.32771–32775, 1998.

Queimado, L. et al., Cloning the human and mouse MMS19 genes and functional complementation of a yeast mms 19 deletion mutant, Nucleic Acids Research, 29(9):pp.1884–1891, 2001.

Ohi, R. et al., Myb–Related *Schizosaccharomyces pombe* cdc5p Is Structurally and Functionally Conserved in Eukaryotes, Molecular and Cellular Biology, 18(7):pp.4097–4108, Jul. 1998.

Nikawa, J. et al., Structural and functional conservation of human and yeast HCP1 genes which can suppress the growth defect of the *Saccharomyces cerevisiae* ire15 mutant, Gene, 171:pp.107–111, 1996.

Dotan, I. et al., Functional Conservation between the Human, Nematode, and Yeast CK2 Cell Cycle Genes, Biochemical and Biophysical Research Communications, 288:pp.603–609, 2001.

Adams, A.E.M., et al., Isoform–Specific Complementation of the Yeast sac6 Null Mutation by Human Fimbrin, Molecular and Cellular Biology,pp. 69–75, Jan. 1995.

Kissil, J.L. et al., Structure–function analysis of an evolutionary conserved protein, DAP3, which mediates TNF–a– and Fas–induced cell death, The EMBO Journal, 18(2):pp.353–362, 1999.

Rothbacher, U. et al., Functional Conservation of the Wnt Signaling Pathway Revealed by Ectopic Expression of *Drosophila* dishevelled in *Xenopus*, Developmental Biology, 170:pp.717–721, 1995.

Buzanska, L., et al., Human Medulloblastoma Cell Line DEV Is a Potent Tool to Screen for Factors Influencing Differentiation of Neural Stem Cells, Journal of Neuroscience Research, 65:17–23, 2001.

Fossett, N. and Schulz, R., Functional conservation of hematopoietic factors in *Drosphila* and vertebrates, Differentiation, 69:pp.83–90, 2001.

Ferrier, D.E.K. and Holland P.W.H., Ancient Origin of the Hox Gene Cluster, Reviews, School of Animal & Microbial Science.

Hanson, I. and Van Heyningen, V. et al., Pax6: more than meets the eye, TIG, 11(7), Jul. 1995.

Laufer, E. et al., Expression of Radical fringe in limb–bud ectoderm regulates apical ectodermal ridge formation, Nature, 386:pp.366–373, Mar. 27, 1997.

Wilson, R. et al. (1994): Nature 368:32–38.

Wilson, R. et al. (1994), XP–002089006 "*Caenorhabditis elegans* cosmid ZC395".

Wilson, R. et al. (1994), XP–002089545 "*Caenorhabditis elegans* cosmid C34E10".

Adams, M.D. et al. (1995), Nature 377:3–17.

Adams, M.D. et al. (1997), XP–002089546 "EST36068 Embryo, 8 week 1 *Homo sapiens* CDNA 5' end similar to similar to IRNA isopenlenyltransferase".

Adams, M.D. et al. (1997), XP–002089547, "EST64588 Jurkat T–cells VI *Homo sapiens* CDNA 5' end similar to similar to tRNA Isopentenyltransferase".

Lakowski, B. et al (1996), Science 272:1010–1013.

Ewbank, J.J. et al. (1997), Science 275:980–3.

Spieth, J. et al. (1993), Cell 73:521–32.

Hodgkin et al. (1997) Genetics 146:149–64.

Wong et al. (1995) Genetics 139:1247–59.

Hekimi et al. (1995) Genetics 141:1351–67.

\* cited by examiner

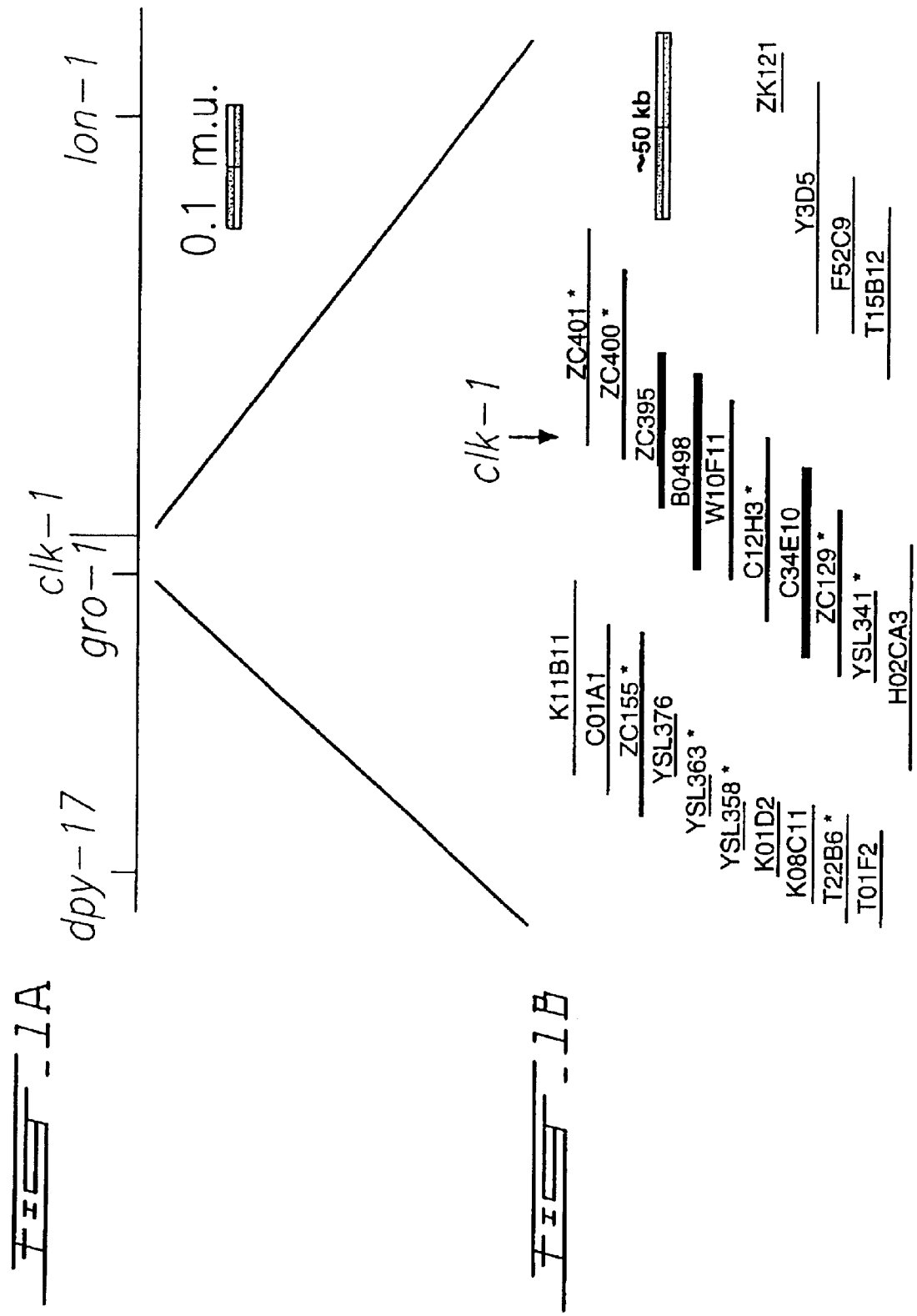

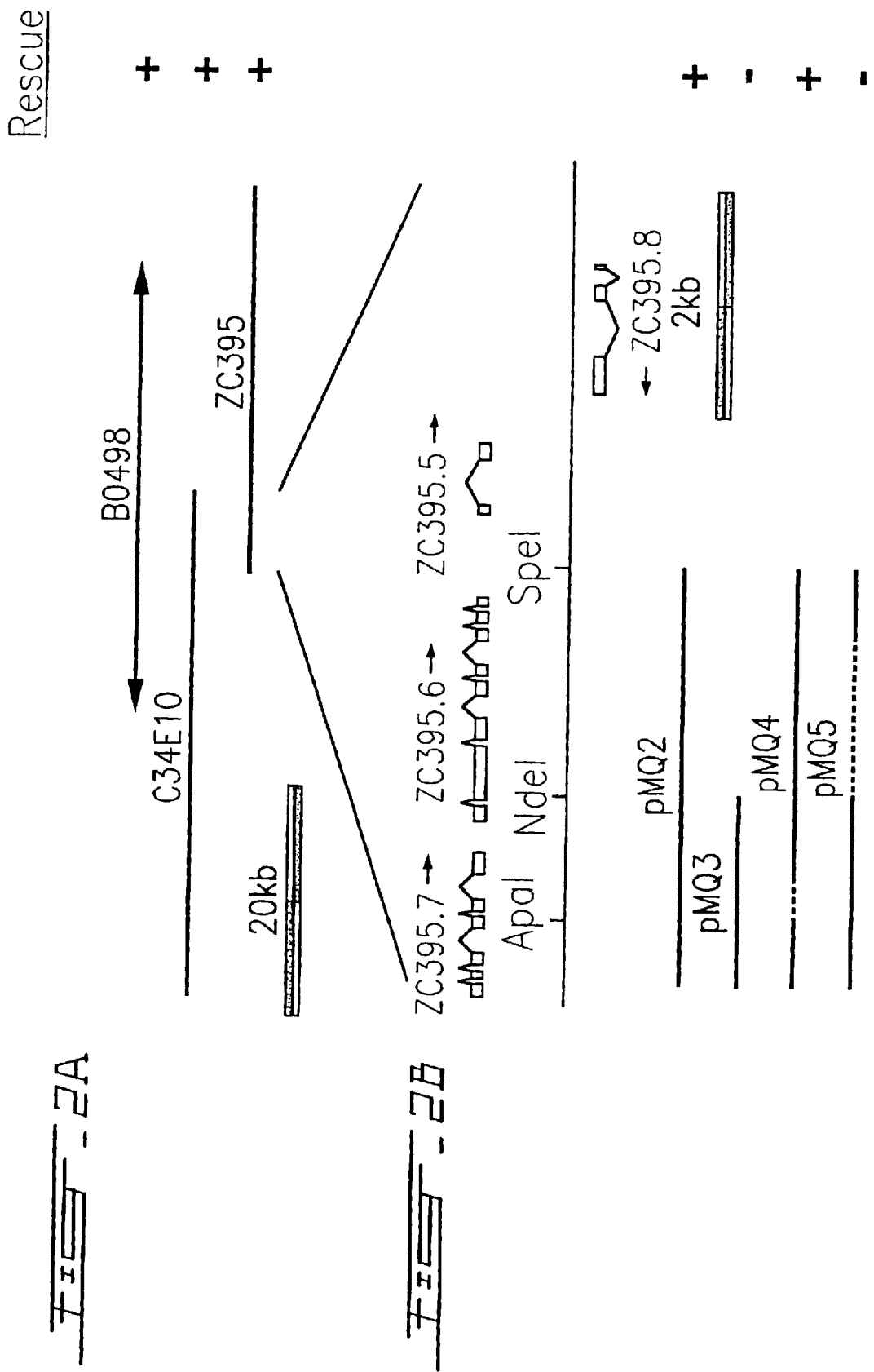

*gro-1*

```
                    SL2                        M  I  F  R  K  F  L  N  F  L  K  P  Y  K  N  R    16
aaatatcgtcaggaaataataacatttcagatatacctgaactctacagtttATGATATTCAGGAAATTTCTGAATTTTCTGAAACCTTACAAAATGC  1394
```

```
 T  D  P  I  I  F  V  I  G  C  T  G  T  G  K  S  D  L  G  V  A  I  A  K  K  Y  G  G  E  V  I  S  V    49
GAACGGATCCGATTATTTTCGTGATTGGGTGCACTGGAACCGGGAAAAGTGATCTTGGAGTGGCAATTGCAAAGAAATATGGAGGAGAGGTGATTAGTGT  1494
                                                                                    ▼ SHP109
```

```
 D  S  M  Q  F  Y  K  G                                            L  D  I  A  T  N  K  I  T    66
AGATTCAATGCAATTTTATAAAGgtacatgggttttgtttcaattttaaattaattaattttcgttttcagGACTTGACATTGCCACGAATAAGATAAC  1594
```

```
 E  E  E  S  E  G  I  Q  H  H  M  M  S  F  L  N  P  S  E  S  S  S  Y  N  V  H  S  F  R  E  V  T  L    99
GGAAGAAGAATCTGAAGGGATTCAACATCATATGATGTCATTTTTGAATCCATCTGAATCATCATCTTATAATGTACATAGTTTCCGAGAAGTCACGTTG  1694
                                                                             SHP94      ▼
```

```
 D  L  I  K                                       K  I  R  A  R  S  K  I  P  V  I  V  G   116
GATCTTATTAAAgtgcttaattcgccacttttttgaacttgatcctaattttcataattttcagAAAATCCGCGCCCGTTCAAAAATTCCTGTAATTGTCG  1794
                                                          ▼ SHP95
```

```
 G  T  T  Y  Y  A  E  S  V  L  Y  E  N  N  L  I  E  T  N  T  S  D  D  V  D  S  K  S  R  T  S  S  E   149
GAGGAACCACTTATTATGCTGAAAGTGTCCTTTATGAGAATAATCTGATTGAAACCAACACTTCAGATGACGTGGATTCCAAATCGAGAACATCATCAGA  1894
                                                          SHP96      ▼
```

```
 S  S  S  E  D  T  E  E  G  I  S  N  Q  E  L  W  D  E  L  K  K  I  D  E  K  S  A  L  L  L  H  P  N   182
ATCGTCATCTGAAGACACTGAAGAAGGAATTAGTAATCAAGAATTATGGGATGAATTGAAAAAAATCGACGAAAAATCAGCACTTCTTCTACATCCAAAT  1994
```

FIG. 3A gro-1 continued...

```
                N  R  Y  R  V  Q  R  A  L  Q  I  F  R  E  T  G                                               198
AATCGTTATCGAGTACAGAGAGCATTGCAAATTTTCAGAGAAACTGgtaattgatttgcaaatttccagattaaaaacaaatcaagtaaagttttttgca         2094

I  R  K  S  E  L  V  E  K  Q  K  S  D  E  T  V  D  L  G  G  R  L  R  F  D  N  S  L  V  I  F  M  D    231
gGAATCCGAAAAAGTGAACTTGTTGAAAAACAGAAATCAGATGAAACTGTTGATTTGGGTGGACGACTACGATTTGATAATTCTTTAGTTATTTTTATGG         2194
         ─────SHP97─────▼

A  T  P  E  V  L  E  E  R  L  D  G  R  V  D  K  M  I  K  L  G  L  K  N  E  L  I  E  F  Y  N  E         263
ATGCAACACCTGAAGTTTTAGAAGAAAGACTTGATGGAAGAGTTGATAAAATGATTAAATTGGGTTTGAAGAATGAATTGATCGAGTTTTATAACGAGgt      2294 aaatatttgaattttttccagaaaaaaaaagaaaattttttattattttgttttttttttcattctttactattttccaaaaaagtttaaacttttgaaaac     2394

H  A  E  Y         267
tgttcagaaaatgttcgtgtatttattttagcttactgaggcattatttcattgtgatttttactatactctataaactaaattttcagCACGCCGAGTA       2494

I  N  H  S  K  Y  G  V  M  Q  C  I  G  L  K  E  F  V  P  W  L  N  L  D  P  S  E  R  D  T  L  N  G      300
CATAAATCACAGCAAATATGGTGTCATGCAATGTATTGGTCTTAAAGAATTCGTTCCATGGCTCAATTTGGACCCATCAGAAAGAGATACACTCAATGGG       2594
                         └CG ┘e2400 lesion                                                  ─────SHP98─────▼

D  K  L  F  K  Q  G                                                  C  D  D  V  K  L  H  T  R  Q  Y       318
GATAAATTGTTCAAGCAAGGgtaatttaaatttattttcaatttttataaattccaagctattttcagATGCGATGATGTGAAGCTTCACACTCGACAAT      2694
```

FIG. 3B

*gro-1* continued...

```
                A  R  R  Q  R  R  W  Y  R  S  R  L  L  K  R  S  D  G  D  R                                                      33
ATGCACGGCGCCAGAGACGGTGGTATCGATCGAGACTTTTAAAACGGTCGGATGGTGATCGGtatgttgatttaaaaaaattgaattttaaagaact  279
         ▼    SHP99 ttttactaaattaacaaagttattggctgaaaatggctgaaaattatagtaaaactaatcaaaaaaattgaatttgaattaaagtcataaagtgacg  289

K  M  A  S  T  K  M  L  D    34
accagaaaattaaaaaaaaacatttttctattttaattaattcactctacttcactttaaaaataattttcagAAAATGGCAAGTACAAAAATGCTGGAT  299

T  S  D  K  Y  R  I  I  S  D  G  M  D  I  V  D  Q  W  M  N  G  I  D  L  F  E  D                  37
ACATCTGACAAGTACCGAATAATTAGTGATGGAATGGACATTGTTGATCAATGGATGAATGGAATCGATCTATTTGAAGATgtaaaatttcacaaattct  309

I  S  T  D  T  N  P  I  L  K  G  S  D  A  N  I  L  L  N  C  E  I   39
aaaatttccgaatcacaaattaaaatttctacagATCTCCACAGACACCAATCCAATTCTAAAAGGGTCCGATGCAAATATTCTGCTGAATTGTGAAATC  319

C  N  I  S  M  T  G  K  D  N  W                                                Q  K  E  I  D  G  K  K    41
TGTAATATTTCAATGACTGGAAAAGATAATTGgtttgtttcaatacatattataatttcgaaatgaattttttcagGCAGAAACATATCGATGGAAAAA  329
                        SHP110 ▼   ▼ SHP100

H  K  H  H  A  K  Q  K  K  L  A  E  T  R  T  •                                                          43
GCACAAGCATCATGCTAAGCAAAAGAAATTGGCAGAGACTCGCACAtaagacgctatatttattttttgttaacttaaattatttttgttgttgattgtt  339 polyA
                                              /
ctctaaataaaaaaacagctcagagagaagattaggcgctcgtccacatctccgacgatagtcaacccgaacgaagggaactatctttaattgtcagtga  349
                                                                                ▼   SHP92
```

*FIG. 3C*

```
tgattttractatactctataaactaaattttcagCACGCCGAGTACATAAATCACAGCAAATATGGTGTCACG    1197
                                   H  A  E  Y  I  N  H  S  K  Y  G  V  T      276

TTGGTCTTAAAGAATTCGTTCCATGGCTCAATTTGGACCCATCAGAAAGAGATACACTCAATGGGGATAAATTGT  1272
    L  V  L  K  N  S  F  H  G  S  I  W  T  H  Q  K  W  I  H  S  M  G  I  N  C  301

TCAAGCAAGGgtaatttaaatttattttcaattttrataaattccaagctattttcagATGCGATGATGtgaagcttc  1350
 S  S  K  D                                                A  M  M  *           308
```

FIG. 3D

Sequence of GRO-1 and homologues

```
                        .  .  . ..  .       .  ..  .   . . .  .
C.elegans     1  MIFRKFLNPLKPYKMRTDPIIFVIGCTGTGKSDLGVAIAKKYGGEVISVDSMQFYKGLDIATNKITEEESEGIQ
S.cerevisiae  1     MLKGPLKGCLNMSKKVIVIAGTTGVGKSQLSIQLAQKFNGEVINSDSMQVYKDIPIITNKHPLQEREGIP
E.coli        1        MSDISKASLPKAIFLMGPTASGKTALAIELRKILPVELISVDSALIYKGMDIGTAKPNAEELLAAP
                                         ─────────
                                          ATP/GTP
                                         binding site .   .   .         .  ..  ....  .
C.elegans     76 HMMSFLMPSESSSYNVHSFREVTLDLIKKIRARSKIPVIVGGTTYYAESVLYENNLIETNTSDDVDSKSRTSSE
S.cerevisiae  72 HVMNHVDWSE--EYYSHRFETECMNAIEDIHRRGKIPIVVGGTHYYLQTLFNKRVDTKSSERKLTRKQLDILES
E.coli        68 RLLDIRDPSQ--AYSAADFRRDALAEMADITAAGRIPLLVGGTMLYFKALLEGLSPLPSADPEVRARIEQQAAE .   .   . ...   .  ..      .   .                    .
C.elegans     151 SSEDTEEGISNQELWDELKKIDEKSALLLHPNNRYRVQRALQIFRETGIRKSELVEKQKSDETVDLGGRLRFDN
S.cerevisiae  147 DPDV---------IYNTLVKCDPDIATKYHPNDYRRVQRMLEIYYKTGKKPSETFNEQK--------ITLKFD-'
E.coli        141 GWES---------LHRQLQEVDPVAAARIHPNDPQRLSRALEVFPISGKTLTELTQTSG--------DALPYQV
```

Fig. 5A

```
                                                          e2400
                  . . . . . . .                             |
C.elegans     226 LVIFMDATPEVLEERLDGRVDKMIKLGLKNELIEFYNEHAEYINHSKYGVMQCIGLKEFVPWLNLDPSERDTLN
S.cerevisiae  205 LFLWLYSKPEPLFQRLDDRVDDMLERGALQEIKQLYEYYSQNKFTPEQCENGVWQVIGFKEFLPWLTGKTDDNT
E.coli        202 QFAIAPASRELLHQRIEQRFEQMLASGFEAEVRALFARGDLHTDLPSIRCVGYRQMWSYLEGEISYDEMVYRGV ... . .. .                                                         .
C.elegans     301 DKLFKQGCDDVKLHTRQYARRQRRWYRSRLLKRSDGDRKMASTKMLDTSDKYRIISDGMDIVDQWMNGIDLFED
S.cerevisiae  280 KLEDCIERMKT--RTRQYAKRQVKWIKKMLIPDIKGDILLDATDLSQWDTNASQRAIAISNDFISNRPIKQERA
E.coli        277 -------------ATRQLAKRQITWLRGWEGVHWLDSEKPEQARDEVLQVVGAIAG ..    .   C2H2 zinc finger   .
C.elegans     376 STDTNPILKGSDANILLNCEICNISMTGKDNWQKEIDGKKKEKHHAKQKKLATRT
S.cerevisiae  353 KALEELLSKGETTMKKLDDWTHYTRNVCRNADGKNVVAIGEKYWKIELGSRREKSNLKRNTRQADFEKWKINKK
                                                                      .
```

FIG. 5B

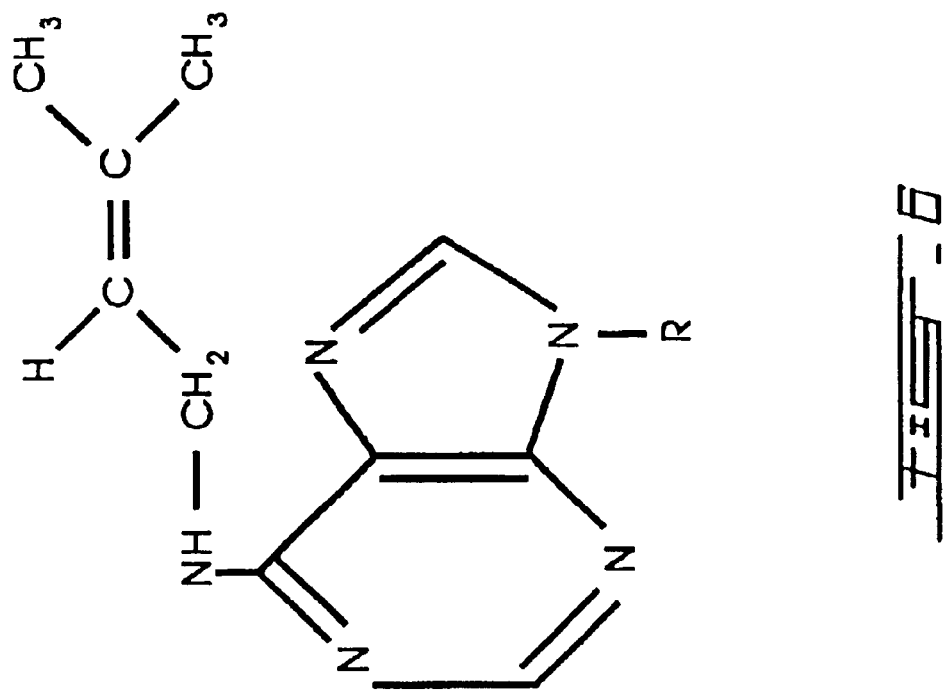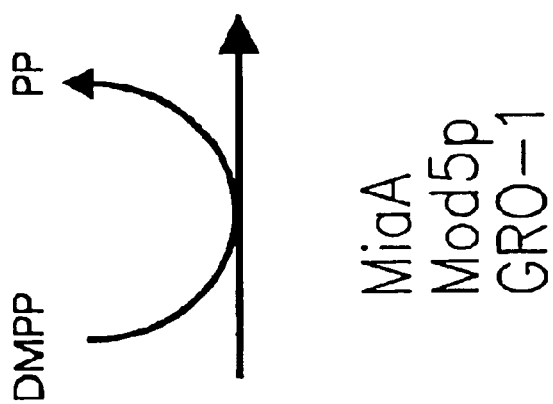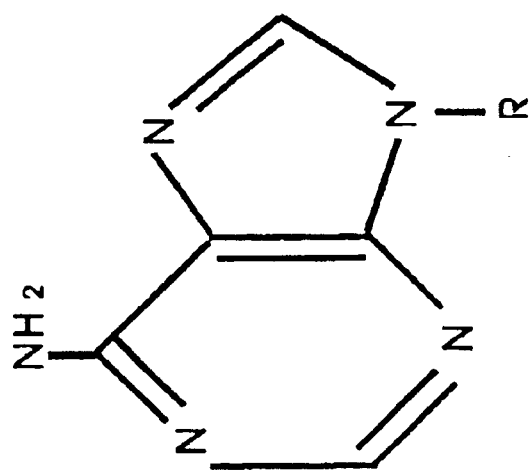
FIG. 6

Sequence of HAP-1 and its homologues

```
                    ...  . .                                              .
H. sapiens          MAASLVGKKIVFVTGNAKKLEEVVQILGDKFP-----CTLVAQKIDLPEYXG-EPDEISIQKCQE
C. elegans          MLYILWKLNYLQKKMSLRKINFVTGNVKKLEEVKAILKNFE--------VSNVDVDLDEFQG-EPEFIAERKCRE
S. cerevisiae             MSNNEIVFVTGNANKLKEVQSILTQEVDNNNKTIHLINEALDLEELQDTDLNAIALAKGKQ
E. coli                   MQKVVLATGNVGKVRELASLLSDFGLD-----IVAQTDLGVDSAEETGLTFIENAILKA .  . .    .. .              .           .
H. sapiens          AVRQV-QG-PVLVEDTCLCFNALGXLPGPYIKWFL--EKLKPEGLHQLLAGFED-----KSAYALCTFALSTGDP
C. elegans          AVEAV-KG-PVLVEDTSLCFNAMGGLPGPYIKWFL--KNLKPEGLHNMLAGFSD-----KTAYAQCIFAYTEG-L
S. cerevisiae       AVAALGKGKPVFVEDTALRFDEFNGLPGAYIKWFL--KSMGLEKIVKMLEPFEN-----KNAEAVTTICFADSRG
E. coli             RHAAKVTALPAIADDSGLAVDVLGGAPGIYSARYSGEDATDQKNLQKLLETMKDVPDDQRQARFHCVLVYLRHAE .  ..     .  .. . .     . .    .   . ... .
H. sapiens          SQPVRLFRGRTSGRIV-APRGCQDFGWDPCFQP-DGYEQTYAEMPKAEKNAVSHRFRALLELQEYFGSLAA
C. elegans          GKPIHVFAGKCPGQIV-APRGDTAFGWDPCFQP-DGFKETFGEMDKDVKNEISHRAKALELLKEYFQNN
S. cerevisiae       E--YHFPQGITRGKIV-PSRGPTTFGWDSIFEPFDSHGLTYAEHSKDAKNAISERGKAFAQFKEYLYQNDF
E. coli             DPTPLVCHGSWPGVITREPAGTGGFGYDPIFFV-PSEGKTAAELTREEKSAISERGQALKLLLDALRNG
```

FIG. 7 mRNA sequence of human homologue of *gro-1*: hgro-1

```
CTGCCATAAG ATGGCGTCCG TGGCGGCTGC ACGAGCAGTT CCTGTGGGCA
GTGGGCTCAG GGGCCTGCAA CGGACCCTAC CTCTTGTAGT GATTCTCGGG
GCCACGGGCA CCGGCAAATC CACGCTGGCG TTGCAGCTAG GCCAGCGGCT
CGGCGGTGAG ATCGTCAGCG CTGACTCCAT GCAGGTCTAT GAAGGCCTAG
ACATCATCAC CAACAAGGTT TCTGCCCAAG AGCAGAGAAT CTGCCGGCAC
CACATGATCA GCTTTGTGGA TCCTCTTGTG ACCAATTACA CAGTGGTGGA
CTTCAGAAAT AGAGCAACTG CTCTGATTGA AGATATATTT GCCCGAGACA
AAATTCCTAT TGTTGTGGGA GGAACCAATT ATTACATTGA ATCTCTGCTC
TGGAAAGTTC TTGTCAATAC CAAGCCCCAG GAGATGGGCA CTGAGAAAGT
GATTGACCGA AAAGTGGAGC TTGAAAAGGA GGATGGTCTT GTACTTCACA
AACGCCTAAG CCAGGTGGAC CCAGAAATGG CTGCCAAGCT GCATCCACAT
GACAAACGCA AAGTGGCCAG GAGCTTGCAA GTTTTGAAG AAACAGGAAT
CTCTCATAGT GAATTTCTCC ATCGTCAACA TACGGAAGAA GGTGGTGGTC
CCCTTGGAGG TCCTCTGAAG TTCTCTAACC CTTGCATCCT TTGGCTTCAT
GCTGACCAGG CAGTTCTAGA TGAGCGCTTG GATAAGAGGG TGGATGACAT
GCTTGCTGCT GGGCTCTTGG AGGAACTAAG AGATTTCAC AGACGCTATA
ATCAGAAGAA TGTTTCGGAA AATAGCCAGG ACTATCAACA TGGTATCTTC
CAATCAATTG GCTTCAAGGA ATTTCACGAG TACCTGATCA CTGAGGGAAA
ATGCACACTG GAGACTAGTA ACCAGCTTCT AAAGAAGGA CCTGGTCCCA
TTGTCCCCCC TGTCTATGGC TTAGAGGTAT CTGATGTCTC GAAGTGGGAG
GAGTCTGTTC TTGAACCTGC TCTTGAAATC GTGCAAAGTT TCATCCAGGG
CCACAAGCCT ACAGCCACTC CAATAAAGAT GCCATACAAT GAAGCTGAGA
ACAAGAGAAG TTATCACCTG TGTGACCTCT GTGATCGAAT CATCATTGGG
GATCGCGAAT GGGCAGCGCA CATAAAATCC AAATCCCACT TGAACCAACT
GAAGAAAAGA AGAAGATTGG ACTCAGATGC TGTCAACACC ATAGAAAGTC
AGAGTGTTTC CCCAGACTAT AACAAAGAAC CTAAAGGGAA GGGATCCCCA
GGGCAGAATG ATCAAGAGCT GAAATGCAGC GTTTAAGAGA CATGTCCAGT
GGCCTTTGGA AAGGTGGTGG GGATCCAGTT CAGGAGGGAG GGGTATGTTT
GTCTCCCAGT CTGGGCAAAG GAGTGCTATG CGGAATTCTC TGCATAGCAG
AAAAGCTCCC ACCATTTTCT TTTGATGTGG TTTTAAAGTC TCACGTTCTC
TATAATAGAA ACAGCAGGTC TTGTCAGCTC CTTGTGTGGC TGATGTGTCT
GGAAATGATG TAGTTCAGGA AAGCATTTTT TTTTTCTTTG AACCTTAAAG
GTTCTATTAT TAAAAGCAGC ACAGATTCCA CATTTTTATA CATGAGGATC
TTCTTTGTGG TGAATACCAG GATTGACTGC ATCCCTTTAA AAGAAGTTTT
ATGTCCCTGA CTCTGGCTAA AATTATCTAA TTTCCAGATG CTTTTGTAGA
TGACTGAAGT ATTTGTGAGC ACATATTGG GAGTTCTAGA TTTGAGTGAA
TGGCAGGAAA GGGCCATCTC CATTGAGATG ATTAAGTGAA CCAAACTAGT
TCTCGGAATT CTACAGAGAA GGAGGGAATC AGACTGAGGA AGCTGTGACA
TAGGACTTGA AGACCAAAGA CTTTGAAATT TGCGAGCTGC TCATGTGTGA
GTTATTATCA CTGCTGTCTT TCTATTGAGT TACAAATCTA TATTTTATT
GAAGTTTAAA TAAAGAAAAA ATTTACAAGA AAAAAAAAA A
```

FIG. 8

GRO-1 and its human homologue hgro-1p

```
                 ...    . ...... .          ... . .... . .... ..
hgro-1p    MASVAAARAVPVGSGLRGLQRTLPLVVILGATGTGKSTLALQLGQRLGGEIVSADSMQVYEGLDIITN
GRO-1            MIFRKFLNFLKPYKMRTDPIIFVIGCTGTGKSDLGVAIAKKYGGEVISVDSMQFYKGLDIATN .  .   ... ..  .   . .  ..   ..  . .. ...  .... .. .. .
hgro-1p    KVSAQEQRICRHHMISFVDPL-VTNYTVVDFRNRATALIEDIFARDKIPIVVGGTNYYIESLLWKVLVN
GRO-1      KITEEESEGIQHHMMSFLNPSESSSYNVHSFREVTLDLIKKIRARSKIPVIVGGTTYYAESVLYENNLI .  ..      .   .  .  .  . ...    . . .. . ....
hgro-1p    TKPQEMGTEKVIDRKVELEKEDGLV------LHKRLSQVDPEMAAKLHPHDKRKVARSLQVFEETGISH
GRO-1      ETNTSDDVDSKSRTSSESSSEDTEEGISNQELWDELKKIDEKSALLLHPNNRYRVQRALQIFRETGIRK
```

FIG. 9A

```
              ..  .  .  ... . .      .  .. .... ... .  ..  ..       .
hgro-1p    SEFLHRQHTEEGGGPLGGPLKFSNPCILWLHADQAVLDERLDKRVDDMLAAGLLEELRDFHRRYNQKNV
GRO-1      SELVEKQKSDETVD-LGGRLRFDNSLVIFMDATPEVLEERLDGRVDKMIKLGLKNELIEF---YNEHAE .  .  . .. ...  .           . .
hgro-1p    SENSQDYQHGIFQSIGFKEFHEYLITEGKCTLETSNQLLKKGPGPIVPPVYGLE--------------
GRO-1      YINHSKY--GVMQCIGLKEFVPWLNLDPSERDTLNGDKLFKQGCDDVKLHTRQYARRQRRWYRSRLLK ..    .           .                 .
hgro-1p    VSDVSKWEESVLEPALEIVQSFIQGHKPTATPIKMPYNEAENKRSYHL------------
GRO-1      RSDGDRKMASTKMLDTSDKYRIISDGMDIVDQWMNGIDLFEDISTDTNPILKGSDANILLN . .   .  .  .. ..   .
hgro-1p    CDICDRIIIGDREWAAHIKSKSHLNQLKKRRRLDSDAVNTIESQSVSPDYNKEPKGKGSPGQNDQELKCSV
GRO-1      CEICNISMTGKDNWQKHIDGKKHKHHAKQKKLAETRT
                C2H2 zinc finger
```

FIG. 9B

Conceptual translation of a partial sequence of the Drosophila homologue of *gro-1*

PITCKHKKQLTATSGSVPIGIHVLKTCGFYLP Stop IHSQ Stop LT Stop VE
Met IRKVPLIVVLGSTGTGKTKLSLQLAERFGGEIISADS Met QVYTHL
DIATAKATKEEQSRARHHLLDVATPAEPFTVTHFRNAALPIVERLL
AKDTSPIVVGGTNYYIESLLWDILVDSDVKPDEGKHSGEHLKDAEL
NALSTLELHQHLAKIDAGSANRIHPNNRKIIRAIEVYQSTGQT

AGATTCAATGCAATTTTATAAAGgtacatgggttttgtttcaattttttaaattaattaattttcgtttttcagGACTTGACATTGCCACGAAT.........
```

```
    . . . H A K Q K K L A E T R T *

.........CATGCTAAGCAAAAGAAATTGGCAGAGACTCGCACAtaagacgctatatttattttttgttaacttaaattattttttgttgttgattgtt
                              ▼
                              SHP170
                                       └─(tctaga)tatact
                                           XbaI ctctaaataaaaaaacagctcagagagaagattaggcgctcgtccacatctccgacgatagtcaacccgaacgaagggaactatctttaattgtcagtga
                                                                        ▼
                                                                        SHP162
                                                                                 └─(ctgcag)tgtcat
                                                                                      PstI
```

FIG. 11B

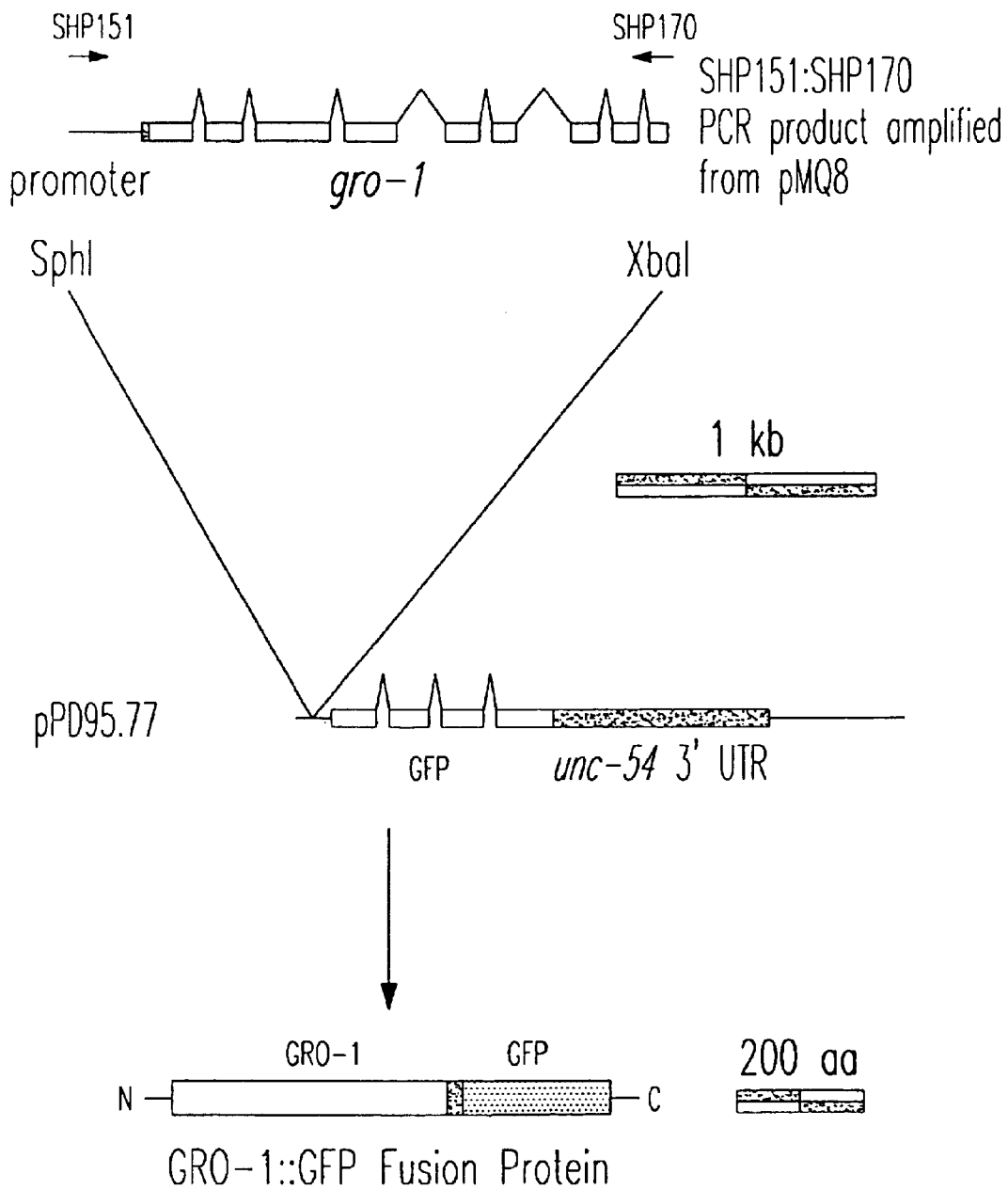

*gop-1*

```
atcgtgttccaggtgcaactatatattgagcaggaggacgagttgtttgtttcatgctgcttaaaaataaaaatggaaaattgagtcaaaaagttgagat  -9557 aaaacaaattaaaacaattttctgaaaaataaacaactgaaatttgaagtaataaacaacacgcgaaaacgttatttcggagcatcgtttgagaagtaaa  -9457 actttttttcggcgcaccccttgtgcgcagttttttatcttctcttttaatttaattttcaagctaaatctttcttttaaactttgaataaatatttaaat  -9357
```

```
                                      M F R K L G S S G S L W K P K N P H S L E    21
attcagaatgcaccaataaacctggaacaaaatcgataATGTTCCGCAAGCTTGGTTCTTCTGGGTCACTATGGAAGCCGAAAAATCCGCATTCTTTGGA  -9257
                                      ‾‾‾‾‾‾‾‾‾‾‾‾‾‾‾‾‾‾‾‾‾‾‾‾‾‾‾
                                              SHP190       ▼
```

```
  Y L K Y L Q G V L T K N E K V T E N N K K I L V E A L R A I A E I                54
ATACCTCAAATATTTACAAGGAGTGCTCACAAAAAATGAGAAAGTTACGGAAAACAATAAGAAAATATTAGTAGAAGCATTACGAGCTATCGCAGAAATT  -9157
```

```
  L I W G D Q N D A S V F D                                        F F L E R      72
CTCATTTGGGGCGATCAGAATGATGCTTCGGTTTTTGAgtgagttttttttccaatgttttttttcaaatctgatgttgaatttcagTTTCTTCCTTGAGC  -9057
```

```
  Q M L L Y F L K I M E Q G N T P L N V Q L L Q T L N I L F E N I R               105
GGCAAATGCTTCTTTATTTCTTGAAAATTATGGAACAAGGAAACACACCACTAAATGTACAATTACTGCAGACTTTGAACATTTTATTCGAAAATATTCG  -8957
                                                    ‾‾‾‾‾‾‾‾‾‾‾‾‾‾‾‾‾‾‾‾‾‾‾‾‾‾‾
                                                    ▼          SHP171
  H E T S L Y                                F L L S N N H V N S I I              123
ACATGAAACTTCACTTTgtaagttttttatatggattttcgcttaaaattgccagttttcagATTTCCTTCTAAGTAACAATCATGTAAACTCGATTATT  -8857
```

```
  S H K F D L Q N D E I M A Y Y I S F L K T L S F K L N P A T I H F F             157
TCCCACAAATTCGATTTACAAAATGATGAGATCATGGCTTACTACATTAGTTTTCTGAAAACTCTTTCATTTAAACTGAATCCAGCTACAATCCACTTCT  -8757
```

FIG. 13A

*gop-1* continued...

```
          F  N  E  T  T  E  E  F  P  L  L  V  E  V  L  K  L  Y  N  W  N  E  S  M  V  R  I  A  V  R  N  I  L                190
TCTTCAATGAAACGACTGAAGAATTTCCATTGTTGGTAGAAGTTTTGAAGCTTTATAATTGGAATGAATCAATGGTTCGAATTGCTGTTAGAAATATTCT  -8657
                                 ▼         SHP141              SHP172      ▼

L  N  I  V  R  V  Q  D  D  S  M  I  I  F  A  I  K  H  T  K                                                        210
TTTAAATATTGTGAGAGTTCAAGATGATTCAATGATTATTTTCGCTATCAAGCATACAAAAgttagtagaaaattattttgaaaaggtgtatttaagcaa  -8557

E  Y  L  S  E  L  I  D  S  L  V  G  L  S  L  E  M  D  T  F  V  R  S  A  E  N  V  L  A  N         240
taaatattacagGAATATCTATCGGAGTTAATAGATTCTCTAGTTGGTCTCTCACTTGAAATGGACACATTTGTACGATCTGCTGAGAATGTGTTAGCTA  -8457
                                                                                                    ▼

R  E  R  L  R  G  K  V  D  D  L  I  D  L  I  H  Y  I  G  E  L  L  D  V  E  A  V  A  E  S  L  S  I         273
ATCGAGAGAGATTACGAGGAAAAGTGGATGATTTAATTGATTTGATTCATTATATTGGTGAACTATTGGATGTGGAAGCTGTCGCCGAAAGTTTATCAAT  -8357
          SHP142                             SHP173           ▼

L  V                                                    T  T  R  Y  L  S  P  L  L  L  S  S  I  S  P  R         291
TTTAGgtcagttttactgctggaaaatcaagttttttaatgttaaattttcagTAACAACACGATACTTAAGCCCTCTATTACTTTCAAGTATATCACCAA  -8257

R  D  N  H  S  L  L  L  T  P  I  S  A  L  F  F  F  S  E  F  L  L                                  313
GAAGAGATAATCATTCACTTCTACTCACTCCGATTTCTGCGTTATTTTTTTTCTCTGAATTTTTATTGgtgagttttaacatttaaaattacatttttct  -8157

I  V  R  H  H  E  T  I  Y  T  F  L  S  S  F  L  F  D  T  Q  N  T  L  T  T  H  W  I         341
aatttatttattttcagATAGTTCGTCACCATGAAACAATATATACATTTTTATCATCTTTCCTATTTGACACTCAGAATACTTTGACGACCCATTGGA  -8057

R  H  N  E  K  Y  C  L  E  P  I  T  L  S  S  P  T  G  E  Y  V  N  E  D  H                         366
TACGTCATAATGAGAAATATTGCTTAGAACCGATTACATTATCATCACCAACCGGAGAATATGTGAATGAAGACCAgtaagagctgaaattttaaaattt  -7957

V  F  F  D  F  L  L  E  A  F  D  S  S  Q  A  D  D  S  K  A  F  Y  G  L  M                  391
ttgctttgaatatagtattttcagCGTATTTTTCGATTTTCTACTGGAAGCATTTGATTCCAGTCAAGCAGACGATTCGAAGGCATTCTATGGATTAATG  -7857
```

FIG. 13B

*gop-1* continued...

```
L  I  Y  S  M  F  Q  N  N  A                                                                                                401
CTGATTTATTCAATGTTTCAGAATAATGgtgagttttaaaaaattgatttgttaaattaaaatttccatttccaataactcctcttcagacagtaagttt  -7757 tcaatgttgtaaagttcctgttcatctgtgatcgttttcttcattttttagttttgcatgaacagttttcaaattttttgatatcatacagtaaatat  -7657 cgtcatccagataatttctatttaaaaaaaatgaataaaaagagggcgcgcagaaattgccgaagtaatgtaaatttaaagggacacatgcgtagcttg  -7557 ttgtgtgggtctcgccgcgctttgtttgatttatcttgttttctgctcaaagagctgttttattttagcgttgaatgctttttttaccgttctcatcggc  -7457 tttttaataggaatatttaaaaaaaaaggtttaataaatcttcgttttttacaaaatccatctaagatttgcatttgtgaagctcaacaagtaaagttta  -7357 agtaacattgttttttaaaaaacaattgaaccaaattttgccgaaacattaataacatgacgatactctataaaatattcctcttttcaaaataaatttt  -7257

D  V  G  E  L  L  S  A  A  N  F  P  V  L  K  E  S  T  T  T  S  L  Q  Q  N  427
caaaaaaaatccatttttcagCCGATGTTGGAGAACTTCTATCTGCTGCCAACTTCCCAGTGCTCAAAGAATCAACGACAACTTCATTAGCTCAACAGAA  -7157
                     ▼ SHP174

L  A  R  L  R  I  A  S  T  S  S  I  S  K  R  T  R  A  I  T  E  I  G  V  E  A  T  E  E  D  E  I  F  480
TCTTGCTCGTCTCCGAATAGCATCTACGTCTTCCATATCAAAGCGAACGAGAGCTATCACTGAAATTGGAGTAGAAGCGACCGAGGAAGATGAGATTTTT  -7057
                                                                          SHP185 ▼

H  D  V  P  E  E  Q  T  L                                                                                                469
CATGATGTTCCTGAAGAACAAACGTTGgtaagtaaataaatcaacattgattgttacacaaactttaatatttttaaatttgaaaatttttcttcaaagtg  -6957

E  D  L  V  D  D  V  L  V  D  T  E  N  S  A  I  S  D  P  E  489
ctcaaaaatcctgtcgaaaattacagGAAGATCTGGTGGATGATGTATTGGTTGATACTGAAAATTCAGCAATAAGTGATCCAGAAgtgagtagaaaacg  -6857

P  K  N  V  E  S  E  S  R  498
tgcatgtattaattattaaaaaaaaaaatatagttttccccagttttccttgacctaaaactcagcaatttcagCCTAAAAACGTGGAGTCAGAATCTCGT  -6757
```

FIG. 13C gop-1 continued...

```
          S  R  F  Q  S  A  V  D  E  L  P  P  P  S  T  S  G  C  D  G  R  L  F  D  A  L  S  S  I  I  K  A  V  G    532
TCTCGATTTCAATCTGCTGTTGATGAGCTTCCACCTCCGTCGACTTCTGGATGTGATGGTCGACTTTTTGATGCACTTTCATCGATTATCAAAGCAGTTG  -6657

T  D  D  N  R  I  R  P  I  T  L  E  L  A  C  L  V  I  R  Q  I  L  M  T  V  D  D  E  K                 561
GAACAGATGACAATCGAATTCGACCAATTACATTGGAACTTGCATGTCTTGTAATTCGGCAAATTTTAATGACTGTTGATGATGAAAAAgtaagattaca  -6557
                       SHP175           ▼

V  H  T  S  L  T  K  L  C  F  E  V  R  L  K  L  L  S         579
aattcaaaattgagcaaaatcagaatctaaatttcataaattgttcagGTACATACCAGTTTAACGAAATTATGCTTCGAAGTTCGTCTAAAACTTTTAT  -6457

S  I  G  Q  Y  V  N  G  E  N  L  F  L  E  W  F  E  D  E  Y  A  E  F  E                              603
CATCAATTGGACAATATGTTAATGGAGAGAATCTGTTTTTGGAGTGGTTTGAGGATGAATATGCAGAATTTGAAgtaagccaagaggtccgaaaataatt  -6357

V  N  H  V  N  F  D  I  I  G  H  E  M  L  L  P  P  A  A  T  P  L  S  N  L  L  L    630
taattcatcctttttattcagGTGAATCACGTGAATTTCGATATAATCGGTCACGAAATGCTTCTTCCTCCAGCTGCAACTCCTCTTTCGAATCTGCTAC  -6257

H  K  R  L  P  S  G  F  E  E  R  I  R  T                                              Q  I  V         647
TTCATAAGCGATTGCCCAGTGGATTTGAAGAACGAATAAGAACTgtaggaaacttttttaaatttgaaaattaattatatatatatttgcagCAAATCGTA  -6157

F  Y  L  H  I  R  K  L  E  R  D  L  T  G  E  G  D  T  E  L  P  V  R  V  L  N  S  D  Q  E  P  V  A  I       681
TTCTACCTACATATTCGAAAATTGGAACGAGATTTGACCGGTGAAGGAGACACAGAATTACCTGTGAGAGTGTTGAATTCTGATCAGGAACCAGTTGCCA  -6057

G  D  C  I  N  L  H                                                              N  S  D  L  L  S  C  T     696
TCGGTGATTGTATTAATTTACgtgagttcatctgcatagaaaacaccatatttctactcaaattaacaattttcagATAATTCGGATCTTCTATCCTGCA  -5957

V  V  P  Q  Q  L  C  S  L  G  K  P  G  D  R  L  A  R  F  L  V  T  D  R  L  Q  L  I  L  V  E  P  D       729
CTGTGGTTCCTCAACAACTATGTTCTCTTGGAAAACCTGGTGATCGTCTTGCTCGATTCCTTGTCACTGATAGACTTCAATTAATTCTTGTCGAACCGGA  -5857
                    ▼   SHP176

S  R  K  A  G  W  A  I  V  R  F  V  G  L  L  Q  D  T  T  I  N  G  D  S  T  D  S  K  V  L  H  V  V       762
TTCTCGAAAAGCCGGATGGGCAATTGTTCGATTCGTAGGACTTCTTCAAGATACAACAATTAATGGAGATTCTACGGATTCGAAAGTTTTGCATGTTGTG  -5757
                                                                          SHP177      ▼
       V  E  G  Q  P  S  R  I  K                                                 K  R  H  P  V  L  T  A       779
GTGGAAGGGCAACCCTCGAGAATTAAGgtaagaatactaacgggaaaaaaaaatcaaaaaattacttctgtttcagAAAAGACATCCGGTTTTAACTGCA  -5657
```

FIG. 13D gop-1 continued...

```
     A F I F D D H I R C M A A K Q R L T K                                                                    798
AAGTTCATATTCGATGATCACATTCGGTGTATGGCAGCAAAGCAACGGCTCACCAAGgtaacggaaaaaataaccaaaaagacggaaagttattgtaaat         -5557 ggacgaaatcggcgaaattaattgaaaacgtttgaatttgccgctaaaaccaaacgaaaaccaaacgaaagcgaaatttaactatcccttcaggtagaat        -5457

G R Q T A R G L K L Q A I C S A L G V P R I D P A T                              824
atacattttatttctctttatagGGTCGCCAAACAGCACGTGGTCTGAAACTTCAGGCGATATGTTCAGCTCTTGGAGTTCCACGTATCGATCCAGCGAC        -5357

M T S S P R M N P F R I V K G C A P G S V R K T V S T S S S S Q                                              857
AATGACGTCATCACCACGAATGAATCCATTCAGAATTGTGAAAGGATGCGCACCGGGAAGTGTACGAAAAACTGTTTCCACATCATCATCGTCAAGCCAA        -5257

G R P G H Y S A N L R S A S R N A G M I P D D P T Q P S S S E R R                                            891
GGACGTCCCGGACATTATTCTGCAAATCTTAGATCAGCATCTAGAAATGCAGGAATGATACCAGATGATCCAACTCAACCGAGTAGTTCTTCGGAAAGAA       -5157
                                                       SHP178      ▼
 S *                                                                                                         892
GATCCtagggatcaatatctcttcagtttcatcatttatgctgtaaattgtatttaagtattcctattctttgtagtactgtatttacacatcgtctag       -5057 ttaaaatcacaaatctccgaaaaaacaaaccagtgaacatgtgatatttctcttgcccatagttctctttttttttttgaaacaaaaacaattacttttat    -4957 polyA
                                                                                                  ┌─
gctcacctattcgagccatattttttttcccaattaccggttgtttatttaatttcttttttttttctgtaaatctactttattttttaaaactgcatttg     -4857 agattgtgtatatttttcaaaatggttcaaatgccgaatctatctactt                                                          -4807
```

FIG. 13E

*gop-2*

```
                     SL2              M A E K A E N L P S S S A E A S E   1
                      \
tttaatcattattcaaacagaaaaaccgattatttattcagattctcaaaaATGGCTGAAAAAGCTGAAAATCTTCCATCTTCTTCGGCCGAAGCTTCAG  -470

E P S P Q T G P N V N Q K P S I L V L G M A G S G K T T F V Q          4
AAGAGCCATCACCTCAAACTGGACCAAATGTGAATCAAAAACCATCGATTTTGGTTCTTGGAATGGCTGGTTCTGGAAAAACGACATTTGTTCAGgtaac  -460

R L T A F L H A R K T P P Y V I N L D P   6
tttcattcaattttgagagttttcaaacattactattttcagCGTCTCACAGCATTCCTACATGCTCGTAAAACACCTCCATATGTGATTAATCTGGATC  -450

A V S K V P Y P V N V D I R D T V K Y K E V M K E F G M G P N G A          10
CGGCAGTTAGCAAAGTACCTTATCCAGTGAATGTTGACATTCGAGATACTGTGAAATACAAGGAAGTTATGAAAGAATTCGGAATGGGACCAAATGGAGC  -440
                                      ▼
                                    SHP179

I N T C L N L M C T R F D K V I E L I N K R S S D F S V C L L D T   13
AATTATGACATGTCTTAACCTGATGTGTACTCGTTTTGATAAAGTAATTGAGTTGATTAATAAGAGATCTTCTGATTTCTCAGTTTGTCTTCTTGATACT  -430
      SHP180                        ▼

P G Q I E A F T W S A S G S I I T D S L A S S H P T         16
CCTGGACAAATTGAAGCATTCACTTGGAGTGCTAGTGGATCTATTATCACTGATTCATTGGCAAGTAGCCATCCCACGgtaagggatttgatttatgaa  -420
                                                        ▼
                                                      SHP143 atctgcttgaaatgaaaaaagattctaataaattttgacttttaaacatttttacagttatatttggtctatttctatcattaaaagcaaaatgaaa  -410

V V M Y I V D S A R A T N P T T F M S N          18
agtcgattctactccatatttattaatttcgacttttcagGTGGTAATGTACATTGTGGATTCCGCTCGTGCCACAAATCCAACTACATTCATGTCCAAT  -400
                                          ▼
                                        SHP144
```

FIG. 14A gop-2 continued...

```
          M  L  Y  A  C  S  I  L  Y  R  T  K  L  P  F  I  V  V  F  N  K  A  D  I  V  K  P  T  F  A  L  K  W  M    21
ATGCTCTACGCATGTTCCATTCTCTACCGTACCAAACTTCCATTCATTGTCGTTTTCAACAAAGCTGATATTGTCAAACCAACATTTGCACTCAAATGGA            -390

Q  D  F  E  R  F  D  E  A  L  E  D  A  R  S  S  Y  M  N  D  L  S  R  S  L  S  L  V  L  D  E  F  Y                24
TGCAAGATTTCGAAAGATTTGATGAAGCTTTAGAGGATGCCAGAAGCAGTTATATGAATGATTTGAGTCGTTCATTGAGTCTCGTTCTTGATGAATTCTA            -380
                            ─────────────▼
                               SHP181

C  G  L  K  T  V                                  C  V  S  S  A  T  G  E  G  F  E  D  V                          26
TTGCGGACTGAAAACAGgttttattcgaaataaaaccttttttaaataataaatttcagTTTGCGTCAGTTCTGCAACTGGAGAAGGATTCGAAGATGT              -370

M  T  A  I  D  E  S  V  E  A  Y  K  K  E  Y  V  P  M  Y  E  K  V  L  A  E  K  K  L  L  D  E  E  E               29
AATGACAGCAATCGATGAAAGTGTTGAAGCATACAAAAAAGAATATGTTCCAATGTATGAAAAAGTGTTGGCTGAGAAAAAACTATTGGATGAGGAGGAG            -360

R  K  K  R  D  E  E                                T  L  K  G  K  A  V  H  D  L  N  K  V                         31
AGAAAGAAAAGAGATGAAGAGgtaattgtagtaatttaattctgattatcttcaaattttcagACTCTGAAAGGAAAAGCTGTTCACGACCTGAACAAAG            -350

A  N  P  D  E  F  L  E  S  E  L  N  S  K  I  D  R  I  H  L  G  G  V  D  E  E  N  E  E  D  A  E  L            35
TCGCCAATCCCGACGAATTTCTGGAGTCGGAGTTGAATTCAAAAATCGATAGAATTCATTTGGGCGGAGTCGATGAAGAGAATGAGGAGGATGCTGAACT            -340
                      ─────────────────────▼
                         SHP182

E  R  S  •                                                                                                        35
CGAAAGATCCTgattttcttttgttttgaattttattctatttgatccctgtttacttcttattgttctcatttgttgcgttgttttacattta                   -330 polyA
                                                    ┌──
ctcatttttgcataaacttgttgcaaaaatcaatataattttgatctggaaatggttttaaaccttaaccttcatatattaataatttttttcaaaa                -320 aaacgttctaaaaggttcctcatttttcaatataggaaattttgaaga                                                                  -315
```

FIG. 14B

*gop-3*

```
                                               SL2
                                               ⌐              M  S  E  K  T  F  H  K      8
tcttttccaaaaatgaggttcttcgcttgaaaagccaacatttaaaaccttttttttttccagaaacctagtggttaATGTCTGAAAAGACGTTCCACAAG  -3057

A  Q  T  I  R  A  K  A  S  G  V  P  S  I  V  E  A  V  Q  F  H  G  V  R  I  T  K  N  D  A  L  V  K  E     42
GCACAGACCATCCGTGCAAAGGCATCCGGAGTGCCTTCAATCGTCGAAGCTGTACAGTTTCATGGAGTTCGCATCACAAAAAACGATGCTTTGGTTAAGG  -2957

V  S  E  L  Y  R     48
AGgtactacccaaatttcaaaatgttgcacaattcaattgaaaatataaattgtgaattaaattcaacttacatgttttttcagGTTTCCGAATTATACA  -285

S  K  N  L  D  E  L  V  H  N  S  H  L  A  A  R  H  L  Q  E  V  G  L  M  D  N  A  V  A  L  I  D  T     81
GAAGTAAAAATCTAGATGAACTTGTTCATAACTCTCATCTGGCGGCTCGTCATCTTCAAGAAGTTGGATTAATGGATAATGCAGTTGCTCTAATTGATAC  -275
                                                               ▼ ─────────────
                                                                     SHP183
 S  P  S  S  N  E  G  Y  V  V  N  F  L  V  R  E  P  K  S  F  T  A  G  V  K  A  G  V  S  T  N  G  D    114
ATCTCCAAGCTCAAATGAAGGATATGTTGTCAATTTCCTAGTTCGAGAACCAAAATCATTCACTGCTGGAGTCAAAGCAGGAGTTTCAACGAATGGAGAT  -26

A  D  V  S  L  N  A  G  K  Q  S  V  G  G  R  G  E  A  I  N  T  Q  Y  T  Y  T  V  K                     14
GCGGATGTCAGTTTAAATGCCGGAAAACAAAGTGTTGGAGGACGAGGAGAGGCAATCAATACACAGTATACATATACTGTAAAGgtaaggacgagagttg  -255
                              ▼ ──────────
                                  SHP145 gcactgccagtttggcatgttctcccaatatttttttaattataaaatttggaagtataaaaaaatgtttgcttcatctaaaaatagccttttcacatga  -245 aaaaattgaaaaaaagtgctcaaaaatttcagaaatttccaatttccaaacaatttggagaactttcaaaaattttccaactgaaattaaagctata    -235
```

*FIG._15A*

*gop-3* continued...

```
                                                                  G D H C F    147
ttctatcactaaattttatacaagtcttaagagaaaatgatgaagtggctcattttgtagaatttcctaaaaaataatatcttcagGGCGATCACTGCTT    -225

N I S A I K P F L G W Q K Y S N V S A T L Y R S L A H M P W N Q S           180
CAACATTTCCGCAATCAAACCATTCCTGGGATGGCAAAAATATTCGAATGTATCAGCGACTCTATACCGTTCACTTGCACATATGCCATGGAATCAATCA    -215
       SHP138        ▼                                                 SHP146 ▼

D V D E N A A V L A Y N G Q L W N Q K L L H Q V K L N A                    208
GATGTTGATGAGAATGCAGCTGTTCTTGCATATAATGGACAACTATGGAATCAAAAGCTTTTGCATCAAGTCAAATTGAATGCGgtaaagtattataagt    -205

I W R T L R A T R D A A F S V R E Q A G H T L         23
gttttgtccaaactatgatacagttcttcagATATGGAGAACACTTCGTGCCACTCGAGATGCCGCATTTTCAGTTCGTGAACAAGCCGGACACACTTTG   -195

K F S L E N A V A V D T R D R P I L A S R G I L A                          25
AAATTCTCGTTGGAGAATGCTGTAGCTGTTGATACAAGAGATAGACCTATTCTTGCAAGTCGTGGAATTCTTGgtaagagtaacaacgactattttttaaa  -185 aaatatctttttcgaaaaaattacgaacgaaaaaaaaactgtattatgtacccaaacgcgaaattttgcagttcttgcgcgttcttgttgataaaaaatat  -175

R F A Q  26
gtaaaaaattggaaaaactacgaaaagtcgataaaaattccgtaccaaccggaaaatgtttcattaatttctcttccttttttcagCTCGTTTTGCTCAA   -165

E Y A G V F G D A S F V K N T L D L Q                                      279
GAGTACGCAGGAGTATTTGGTGATGCGTCATTTGTGAAGAATACATTAGATTTACAGgtaacaaccttatttcaacaattatttcaaattctattaaaaa  -155
         SHP139        ▼

A A A P L P L G F I L A A S F Q A K H L K G L G D R E V H I L         31
taattccagGCAGCTGCCCCTCTTCCACTCGGTTTCATTCTTGCCGCCTCATTCCAAGCGAAACATTTGAAAGGACTCGGAGATCGAGAAGTTCATATTT   -145
         SHP140    ▼
```

FIG. 15B

*gop-3* continued...

```
          D   R   C   Y   L   G   G   Q   Q   D   V   R   G   F   G   L   N   T   I   G                                    330
TGGATAGATGTTATTTGGGTGGACAACAGGATGTTCGAGGATTTGGTCTGAATACTATTGGAgtgagttttaacgaaattctcttgaaagtcaaataatc  -1357
                                                              ▼
                                                             SHP184

V   K   A   D   N   S   C   L   G   G   G   A   S   L   A   G   V   V   H   L   Y   R   P   L   I   P   P   N   M   L   F    361
attttcagGTTAAAGCAGATAACAGTTGTCTTGGAGGAGGTGCTTCACTTGCTGGTGTCGTTCATTTGTATCGGCCATTGATTCCACCAAATATGCTATT  -1257

A   H   A   F   L   A   S   G   S   V   A   S   V   H   S   K   N   L   V   Q   Q   L   Q   D   T   Q   R   V   S   A   G   F   G    394
TGCACACGCATTCCTTGCATCTGGAAGTGTTGCATCAGTTCATTCCAAAAATTTGGTGCAACAATTACAGGATACTCAACGAGTATCAGCCGGATTTGgt  -1157
                       ─────────────────────────▶              ▼
                                 SHP163 gagtttgaaatttaggaaacatttggatgaaatgtatttttaaaaatagatcagctttatttatttgaaaaaaaacgctcattaatcaatagtgatagt  -1057 tccattctgagtttcttcttcttcctcgcggaatacaattttttgacttgttcgcatccttcttgtgtactttgtcaccaatcttctcatcaactaaatct  -957 cgaaactgaaaaaatttcaaaattattccaaaaaatattgatgcagactacctttttgatggcttctggtacgtttctagcgtcgaatggattggctcct  -857 ccaataattaaagtctcgttcggtagtttagccagacggacggtgtgcttcaacattttctaattaatctatttcaattcaagtcactcactctctctt  -757
```

*gop-3* continued...

```
gacgtcttcttctatattccaagaactctgcagaaaatccgtgtccgccttgtgtgtttctagttggcgtcggaggattcacgggtccaagacgaatgga    -657 tgtctaaaaaatgttatattttgcataaagaaaacaccataccttcaccacttttgagttgtgggcgttctgaatggaattgatcgattattattgct    -557 ctttcttgatttgcttctatcagctgcgtaatgaggtgttctaaagatcagctttaattcatttggacaagtgctcctctaataaacttaccctgtactc    -457 attttgaaacgatttacgatgataagattgaaagtggaagttaaatttagtctttcaaagttgaaataaaatcttcataataaataaatttaaatgaa    -357
                                                                                    L  A  F  V  F  K  S   401
agattaaataaattaacgttcacgtagttaaaaaaataatttaaatcttaaacttctaataaaaaatctcaattttccagGACTCGCATTCGTGTTCAAAA -257

I  F  R  L  E  L  N  Y  T  Y  P  L  K  Y  V  L  G  D  S  L  L  G  G  F  H  I  G  A  G  V  N  F  L   434
GTATTTTCCGGCTGGAACTCAACTACACGTATCCATTGAAATATGTGCTCGGCGATTCATTGCTCGGTGGATTCCATATTGGAGCTGGTGTCAACTTCTT -157

Gtagagattaattggatgcaagcaccccctcaaaaagatttttttgaaaaacgataaattcacagaatttcagttcttttttctcccccttttattgttatt -57
         SHP134
``` ttcatcgtaatgctgtgctagaagtcagagtaaatatgagttttttttgtgttctaggaattccatttttttcaggaagcaaatttaataaaaattatcgaa    44
                SHP164 polyA tttcttgctctaaagatgttgtacattttatggaaatgttcgtatagtaa    94
                    SHP135

FIG. 15D

*hap-1*

```
                                                    SL2     M S L R K I N F V T G   11
ttcgaacactttatatttctcgtttttaaaactgtcggtgttttatagtaaactatcttcagaaaaaaATGAGCCTACGAAAAATCAATTTCGTAACTGGA  194
         SHP91        ▼                                             SHP118      ▼

N V K K L E E V K A I L K N F E                                                                        27
AACGTGAAGAAGCTTGAAGAAGTCAAGGCTATTTTGAAGAATTTCGAGgtaaaatatatttgatattattcgaacgcgaaattttgcgccaaaagtacga  294 tgcctggtctcaacacgacaatatttgttaaatacaaacgaatgtgcgccttcaaagaaaagtttcaatctttcgttgccgtggagatattttagagt  394

V S N V D V D L D E F   38
ttttgtttaaattatatatttgtcgtatcgaaaccgggtaccgtaatcaatcaattaaatattttcagGTTTCAAACGTGGATGTCGATTTGGATGAATT  494
                                                                           ▼
                                                                         SHP165

Q G E P E F I A E R K C R E A V E A V K G P V L                                                         62
CCAAGGAGAACCCGAATTTATTGCCGAAAGAAAGTGCCGTGAGGCTGTTGAAGCTGTAAAAGGGCCCGTTTTGgtatggaaaattgtatttgttctaaaa  594

V E D T S L C F N A M G G L P G P Y I K W F L K N L K P E   91
attgtcaaatttcagGTCGAAGACACAAGTTTATGCTTCAACGCAATGGGCGGTCTTCCTGGACCTTATATCAAGTGGTTTTTGAAGAATTTGAAACCAG  694
                 ▼
                SHP129
```

FIG. 16A

*hap-1* continued...

```
         G  L  H  N  M  L  A                                          G  F  S  D  K  T  A  Y  A  Q  C  I  F    111
      AAGGACTACATAATATGCTAGgtaaatatttttaattttttgaaaaaacttattttttcagCCGGATTTTCTGACAAAACCGCCTATGCTCAATGCATCTTT    794

A  Y  T  E  G  L  G  K  P  I  H  V  F  A  G                                                          126
      GCGTACACTGAAGGACTCGGAAAACCTATTCATGTATTTGCTGgtatgattttttgaatttaattctttaattttatatgttaatttagttgtttcattc    894

K  C  P  G  Q  I  V  A  P  R  G  D  T  A  F  G  W  D  P   145
      ctcaatttatgagagatttttttttcaattttttctatttcagGAAAATGTCCTGGTCAAATTGTTGCTCCACGTGGTGATACTGCTTTTGGATGGGATCC   994
                                                                                              ▼
                                                                                            SHP130

C  F  Q  P  D  G  F  K  E  T  F  G  E  M  D  K  D  V  K  N  E  I  S  H  R  A  K  A  L  E  L  L  K    178
      ATGCTTCCAGCCAGATGGTTTTAAAGAAACATTCGGAGAAATGGATAAAGATGTAAAAAATGAAATTTCTCATCGTGCAAAGGCTCTGGAACTCCTCAAG  1094
                       ▼                                                             ▼
                    SHP119                                                         SHP120

E  Y  F  Q  N  N  *                                                                                     184
      GAATATTTTCAGAATAATtaaattatttttttctcatctatgcaatttcttgaaaatttgttaagtttccgttgttatgcatttgcttttatttaaaaaaa  1194 polyA
                     ⌐
      aaagaatatttttacattaatatattagatatgagaaaagagtaatttctggattttaaccttcctacaaaagaatatttatattttttgtatgattttta  1294
                              ▼
                           SHP93
```

US 6,949,378 B1

C. ELEGANS GRO-1 GENE

RELATED APPLICATIONS

This application is a continuation-in-part of PCT/CA98/00803 filed Aug. 20, 1998, now at the national phase, and claiming priority on Canadian patent application serial number 2,210,251 filed Aug. 25, 1997, now abandoned.

BACKGROUND OF THE INVENTION (a) Field of the Invention

The invention relates to the identification of gro-1 gene and four other genes located within the same operon and to show that the gro-1 gene is involved in the control of a central physiological clock.

(b) Description of Prior Art

The gro-1 gene was originally defined by a spontaneous mutation isolated from of a *Caenorhabditis elegans* strain that had recently been established from a wild isolate (J. Hodgkin and T. Doniach, Genetics 146: 149–164 (1997)). We have shown that the activity of the gro-1 gene controls how fast the worms live and how soon they die. The time taken to progress through embryonic and post-embryonic development, as well as the life span of gro-1 mutants is increased (Lakowski and Hekimi, *Science* 272: 1010–1013, (1996)). Furthermore, these defects are maternally rescuable: when homozygous mutants (gro-1/gro-1) derive from a heterozygous mother (gro-1/+), these animals appear to be phenotypically wild-type. The defects are seen only when homozygous mutants derive from a homozygous mother (Lakowski and Hekimi, *Science* 272: 10101013, (1996)). In general, the properties of the gro-1 gene are similar to those of three other genes, clk-1, clk-2 and clk-3 (Wong et al., *Genetics* 139: 1247–1259 (1995); Hekimi et al., *Genetics,* 141: 1351–1367 (1995); Lakowski and Hekimi, *Science* 272: 1010–1013, (1996)), and this combination of phenotypes has been called the Clk ("clock") phenotype. All four of these genes interact to determine developmental rate and longevity in the nematode. Detailed examination of the clk-1 mutant phenotype has led to the suggestion that there exists a central physiological clock which coordinates all or many aspects of cellular physiology, from cell division and growth to aging. All four genes have a similar phenotype and thus appear to impinge on this physiological clock.

It would be highly desirable to be provided with the molecular identity of the gro-1 gene.

SUMMARY OF THE INVENTION

One aim of the present invention is to provide the molecular identity of the gro-1 gene and four other genes located within the same operon.

In accordance with the present invention there is provided a gro-1 gene which has a function at the level of cellular physiology involved in developmental rate and longevity, wherein gro-1 is located within an operon and gro-1 mutants have a longer life and a altered cellular metabolism relative to the wild-type.

In accordance with a preferred embodiment, the gro-1 gene of the present invention codes for a GRO-1 protein having the amino acid sequence set forth in FIGS. 3A–3B (SEQ ID. NO:2).

The gro-1 gene is located within an operon which has the nucleotide sequence set forth in SEQ. ID NO:1 and which also codes for four other genes, referred as gop-1, gop-2, gop-3 and hap-1 genes.

In accordance with a preferred embodiment, the gop-1 gene of the present invention codes for a GOP-1 protein having the amino acid sequence set forth in FIGS. 13A–13C (SEQ ID. NO:4).

In accordance with a preferred embodiment, the gop-2 gene of the present invention nodes for a GOP-2 protein having the amino acid sequence set forth in FIG. 14 (SEQ ID. NO:5).

In accordance with a preferred embodiment, the gop-3 gene of the present invention codes for a GOP-3 protein having the amino acid sequence set forth in FIGS. 15A–15B (SEQ ID. NO:6).

In accordance with a preferred embodiment, the hap-1 gene of the present invention codes for a HAP-1 protein having the amino acid sequence set forth in FIG. 16 (SEQ ID. NO:7).

In accordance with a preferred embodiment of the present invention, the gro-1 gene is of human origin and has the nucleotide sequence set forth in FIG. 8 (SEQ ID. NO:3).

In accordance with a preferred embodiment of the present invention, there is provided a mutant GRO-1 protein which has the amino acid sequence set forth in FIG. 3C.

In accordance with the present invention there is also provided a GRO-1 protein which has a function at the level of cellular physiology involved in developmental rate and longevity, wherein said GRO-1 protein is encoded by the gro-1 gene identified above.

In accordance with a preferred embodiment of the present invention, there is provided a GRO-1 protein which has the amino acid sequence set forth in FIGS. 3A–3B (SEQ ID. NO:2).

In accordance with a preferred embodiment of the present invention, there is provided a GOP-1 protein which has the amino acid sequence set forth in FIGS. 13A–13C (SEQ ID. NO:4).

In accordance with a preferred embodiment of the present invention, there is provided a GOP-2 protein which has the amino acid sequence set forth in FIG. 14 (SEQ ID. NO:5).

In accordance with a preferred embodiment of the present invention, there is provided a GOP-3 protein which has the amino acid sequence set forth in FIGS. 15A–15B (SEQ ID. NO:6).

In accordance with a preferred embodiment of the present invention, there is provided a HAP-1 protein which has the amino acid sequence set forth in FIG. 16 (SEQ ID. NO:7).

In accordance with the present invention there is also provided a method for the diagnosis and/or prognosis of cancer in a patient, which comprises the steps of:
a) obtaining a tissue sample from said patient;
b) analyzing DNA of the obtained tissue sample of step a) to determine if the human gro-1 gene is altered; wherein alteration of the human gro-1 gene is indicative of cancer.

In accordance with the present invention there is also provided a mouse model of aging and cancer, which comprises a gene knock-out of murine gene homologous to gro-1.

In accordance with the present invention there is provided the use of compounds interfering with enzymatic activity of GRO-1, GOP-1, GOP-2, GOP-3 or HAP-1 for enhancing longevity of a host.

In accordance with the present invention there is provided the use of compounds interfering with enzymatic activity of GRO-1, GOP-1, GOP-2, GOP-3 or HAP-1 for inhibiting tumorous growth.

BRIEF DESCRIPTION OF THE DRAWINGS

FIG. 1A illustrates the genetic mapping of gro-1;

FIG. 1B illustrates the physical map of the gro-1 region;

FIG. 2A illustrates cosmid clones able to rescue the gro-1 (e2400) mutant phenotype;

FIG. 2B illustrates the genes predicted by Genefinder, the relevant restriction sites and the fragments used to subclone the region;

FIGS. 3A–3C illustrate the genomic sequence and translation of the C. elegans gro-1 gene (SEQ ID NO: 2 and 66);

FIG. 3D illustrates the predicted mutant protein (SEQ ID NO: 64 and 65);

FIGS. 5A–5B illustrates the alignment of gro-1 with the published sequences of the E. coli (P16384) and yeast (PO7884) enzymes;

FIG. 6 illustrates the biosynthetic step catalyzed by DMAPP transferase (MiaAp in E. coli, Mod5p in S. cerevisiae, and GRO-1 in C. elegans);

FIG. 7 illustrates the alignment of the predicted HAP-1 amino acid sequence with homolgues from other species (SEQ ID NO: 69, 7, 70 and 71);

FIG. 8 illustrates the full mRNA sequence of human homologue of gro-1 referred to as hgro-1 (SEQ. ID. NO:3);

FIGS. 9A–9B illustrates a comparison of the conceptual amino acid sequences for GRO-1 (SEQ ID NO: 2) and hgro-1p(SEQ ID NO: 63);

FIG. 10 illustrates a conceptual translation of a partial sequence of the Drosophila homologue of gx-o-1 (AA816785) (SEQ ID NO: 72);

FIG. 12 illustrates construction of pMQ18;

FIGS. 13A–13C illustrate the genomic sequence and translation of the gop-1 gene (SEQ ID NO: 73 and 4);

FIG. 14 illustrates the genomic sequence and translation of the gop-2 gene (SEQ ID NO: 74 and 75);

FIGS. 15A–15B illustrate the genomic sequence and translation of the gop-3 gene (SEQ ID NO: 75 and 6); and FIG. 16 illustrates the genomic sequence and translation of the hap-1 gene (SEQ ID NO: 6 and 77).

DETAILED DESCRIPTION OF THE INVENTION

The Gro-1 Phenotype

Figure 4A:
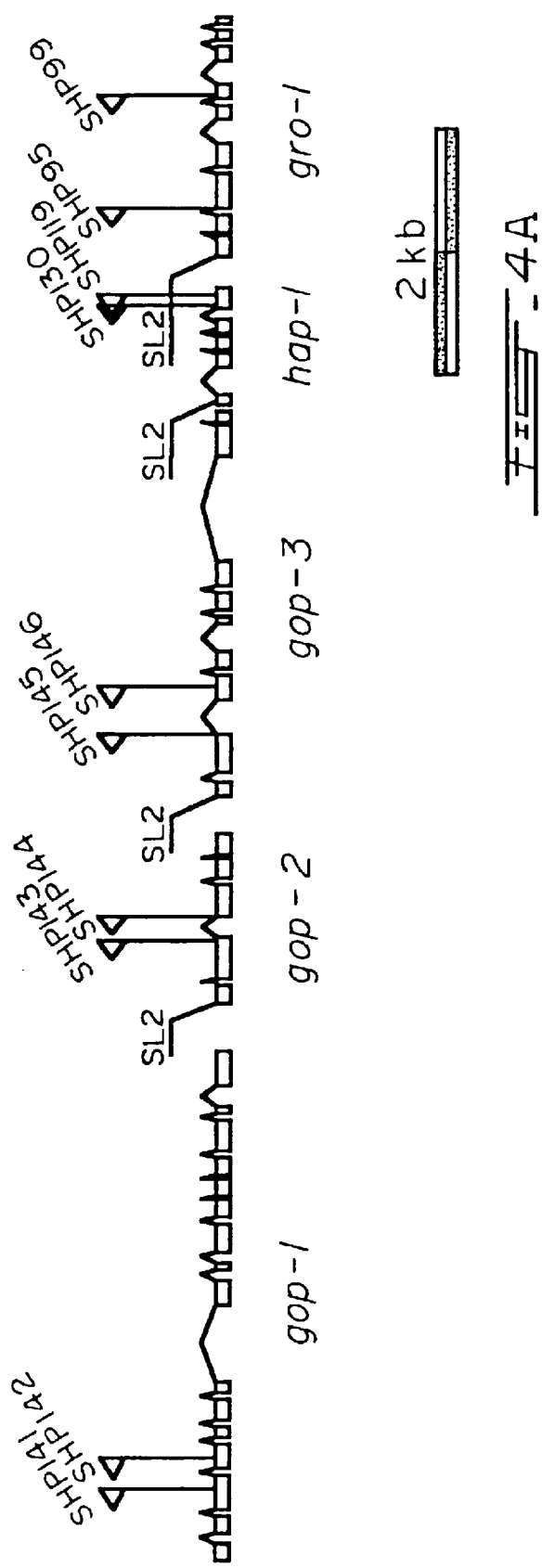
FIG. 4A illustrates the five genes of the gro-1 operon (SEQ. ID. NO:1)

In addition to the previously documented phenotypes, we recently found that gro-1 mutants were temperature-sensitive for fertility. At 25° the progeny of these mutants is reduced so much that a viable strain cannot be propagated. In contrast, gro-1 strains can easily be propagated at 15 and 20° C.

We also discovered that the gro-1 (e2400) mutation increases the incidence of spontaneous mutations. As gro-1 (e2400) was originally identified in a nonstandard background (Hodgkin and Doniach, Genetics. 146: 149–164 (1997)), we first backcrossed the mutations 8 times against N2, the standard wild type strain. We then undertook to examine the gro-1 strain and N2 for the occurrence of spontaneous mutants which could be identified visually. We focused on the two class of mutants which are detected the most easily by simple visual inspection, uncoordinated mutants (Unc) and dumpy mutants (Dpy). We examined 8200 wild type worms and found no spontaneous visible mutant. By contrast, we found 6 spontaneous mutants among 12500 gro-1 mutants examined. All mutants produced entirely mutant progeny indicating that they were homozygous.

| Name | Orientation | Sequence (5'-3') | SEQ ID NO: |
|---|---|---|---|
| SHP91 | forward | CGAACACTTTATATTTCTCG | SEQ. ID. NO:8 |
| SHP92 | reverse | GATAGTTCCCTTCGTTCGGG | SEQ. ID. NO:9 |
| SHP93 | forward | TTTCTGGATTTTAACCTTCC | SEQ. ID. NO:10 |
| SHP94 | forward | TTTCCGAGAAGTCACGTTGG | SEQ. ID. NO:11 |
| SHP95 | reverse | TACAGGAATTTTTGAACGGG | SEQ. ID. NO:12 |
| SHP96 | forward | CTTCAGATGACGTGGATTCC | SEQ. ID. NO:13 |
| SHP97 | forward | GGAATCCGAAAAAGTGAACT | SEQ. ID. NO:14 |
| SHP98 | forward | AAGAGATACACTCAATGGGG | SEQ. ID. NO:15 |
| SHP99 | reverse | ATCGATACCACCGTCTCTGG | SEQ. ID. NO:16 |
| SHP109 | reverse | TTGAATCTACACTAATCACC | SEQ. ID. NO:17 |
| SHP100 | reverse | CCAATTATCTTTTCCAGTCA | SEQ. ID. NO:18 |
| SHP110 | forward | ACATTATAAAGTTACTGTCC | SEQ. ID. NO:19 |
| SHP118 | forward | TTTTAGTTAAAGCATTGACC | SEQ. ID. NO:20 |
| SHP119 | reverse | ACATCTTTATCCATTTCTCC | SEQ. ID. NO:21 |
| SHP120 | forward | TGCAAAGGCTCTGGAACTCC | SEQ. ID. NO:22 |
| SHP129 | reverse | AAAAACCACTTGATATAAGG | SEQ. ID. NO:23 |
| SHP130 | reverse | CATCCAAAAGCAGTATCACC | SEQ. ID. NO:24 |
| SHP134 | forward | TTAATTGGATGCAAGCACCCC | SEQ. ID. NO:25 |
| SHP135 | reverse | ATTACTATACGAACATTTCC | SEQ. ID. NO:26 |
| SHP138 | forward | TTGTAAAGGCGTTAGTTTGG | SEQ. ID. NO:27 |
| SHP139 | forward | CAGGAGTATTTGGTGATGCG | SEQ. ID. NO:28 |
| SHP140 | forward | CGACGGGAGAAGGTGACGG | SEQ. ID. NO:29 |
| SHP141 | reverse | AAAACTTCTACCAACAATGG | SEQ. ID. NO:30 |
| SHP142 | reverse | CGTAATCTCTCTCGATTAGC | SEQ. ID. NO:31 |
| SHP143 | reverse | CCGTGGGATGGCTACTTGCC | SEQ. ID. NO:32 |
| SHP144 | reverse | TGGATTTGTGGCACGAGCGG | SEQ. ID. NO:33 |
| SHP145 | reverse | TTGATTGCCTCTCCTCGTCC | SEQ. ID. NO:34 |
| SHP146 | reverse | ATCAACATCTGATTGATTCC | SEQ. ID. NO:35 |
| SHP151 | forward | CAGCGAGCGCATGCAACTATATATTGAGCAGG | SEQ. ID. NO:36 |
| SHP159 | forward | AATAAATATTTAAATATTCAGATATACC | SEQ. ID. NO:37 |

-continued

| Name | Orientation | Sequence (5'-3') | SEQ ID NO: |
|---|---|---|---|
| | | CTGAACTCTACAG | |
| SHP160 | reverse | AAACTGTAGAGTTCAGGGTATATCTGA ATATTTAAATATTTATTC | SEQ. ID. NO:38 |
| SHP161 | forward | GTACGTGGAGCTCTGCAACTATATATT GAGCAGG | SEQ. ID. NO:39 |
| SHP162 | reverse | ATGACACTGCAGGATAGTTCCCTTCGT TCGGG | SEQ. ID. NO:40 |
| SHP163 | forward | GTGTTGCATCAGTTCATTCC | SEQ. ID. NO:41 |
| SHP164 | forward | GCTGTGCTAGAAGTCAGAGG | SEQ. ID. NO:42 |
| SHP165 | reverse | GTTCTCCTTGGAATTCATCC | SEQ. ID. NO:43 |
| SHP170 | reverse | AGTATATCTAGATGTGCGAGTCTCTGC CAATT | SEQ. ID. NO:44 |
| SHP171 | reverse | AGTAATTGTACATTTAGTGG | SEQ. ID. NO:45 |
| SHP172 | forward | ATTAACCTTACTTACTTACC | SEQ. ID. NO:46 |
| SHP173 | forward | CTAAACTAAGTAATATAACC | SEQ. ID. NO:47 |
| SHP174 | reverse | GTTGATTCTTTGAGCACTGG | SEQ. ID. NO:48 |
| SHP175 | forward | AATTCGACCAATTACATTGG | SEQ. ID. NO:49 |
| SHP176 | reverse | AACATAGTTGTTGAGGAAGG | SEQ. ID. NO:50 |
| SHP177 | forward | AATTAATGGAGATTCTACGG | SEQ. ID. NO:51 |
| SHP178 | forward | TCAGCATCTAGAAATGCAGG | SEQ. ID. NO:52 |
| SHP179 | reverse | CGAATGTCAACATTCACTGG | SEQ. ID. NO:53 |
| SHP180 | forward | CTTAACCTGATGTGTACTCG | SEQ. ID. NO:54 |
| SHP181 | forward | ATGAAGCTTTAGAGGATGCC | SEQ. ID. NO:55 |
| SHP182 | forward | CGACGAATTTCTGGAGTCGG | SEQ. ID. NO:56 |
| SHP183 | reverse | ACTGCATTATCCATTAATCC | SEQ. ID. NO:57 |
| SHP184 | reverse | CACCCAAATAACATCTATCC | SEQ. ID. NO:58 |
| SHP185 | forward | TTTAACCTCATCTTCGCTGG | SEQ. ID. NO:59 |
| SHP190 | forward | ATGTTCCGCAAGCTTGGTTC | SEQ. ID. NO:60 |
| SL1 | forward | TTTAATTACCCAAGTTTGAG | SEQ. ID. NO:61 |
| SL2 | forward | TTTTAACCCAGTTACTCAAG | SEQ. ID. NO:62 |

Positional Cloning of Gro-1 gro-1 lies on linkage group III, very close to the gene clk-1. To genetically order gro-1 with respect to clk-1 on the genetic map, 54 recombinants in the dpy-17 to lon-1 interval were selected from among the self progeny of a strain which was unc-79(e1030)++clk-1(e2519) lon-1(e678)+/+dpy-17 (e164) gro-1(e2400)+sma-4,(e729). Three of these showed neither the Gro-1 nor the Clk-1 phenotypes, but carried unc-79 and sma-4, indicating that these recombination events had occurred between gro-1 and clk-1. From the disposition of the markers, this showed that the gene order was dpy-17 gro-1 clk-1 lon-1, and the frequency of events indicated that the gro-1 to clk-1 distance was 0.03 map units. In this region of the genome, this corresponds to a physical map distance of ~20 kb.

Several cosmids containing wild-type DNA spanning this region of the genome were tested by microinjection into gro-1 mutants for their ability to complement the gro-1 (e2400) mutation (FIG. 1). gro-1 was mapped between dpy-17 and lon-1 on the third chromosome, 0.03 m.u. to the left of clk-1 (Fig. A).

Based on the above genetic mapping, gro-1 was estimated to be approximately 20 kb to the left of clk-1. Eight cosmids (represented by medium bold lines) were selected as candidates for transformation rescue (FIG. 1B). Those which were capable of rescuing the gro-1(e2400) mutant phenotype are represented as heavy bold lines (FIG. 1B).

Of these, only B0498, C34E10 and ZC395 were able to rescue the mutant phenotype. Transgenic animals were fully rescued for developmental speed. In addition, the transgenic DNA was able to recapitulate the maternal rescue seen with the wild-type gene, that is, mutants not carrying the transgenic DNA but derived from transgenic mothers display a wild type phenotype. The 7 kb region common to the three rescuing cosmids had been completely sequenced, and this sequence was publicly available.

We generated sabclones of ZC395 and assayed them for rescue (FIG. 2). The common 6.5 kb region is blown up in part B. B0498 has not been sequenced and therefore its ends can not be positioned and are therefore represented by arrows.

One subclone pMQ2, spanned 3.9 kb and was also able to completely rescue the growth rate defect and recapitulate the maternal effect. The sequences in pMQ2 potentially encodes two genes. However, a second subclone, pMQ3, which contained only the first of the potential genes (named ZC395.7 in FIG. 2A), was unable to rescue.

Furthermore., frameshifts which would disrupt each of the two genes' coding sequences were constructed in pMQ2 and tested for rescue. Disruption of the first gene (in pMQ4) did not eliminate rescuing ability, but disruption of the second gene (in pMQ5) did. This indicates that the gro-1 rescuing activity is provided by the second predicted gene.

pMQ2 was generated by deleting a 29.9 kb SpeI fragment from ZC395, leaving the left-most 3.9 kb region containing the predicted genes ZC395.7 and ZC395.6 (FIG. 2B). pMQ3 was created in the same fashion, by deleting a 31.4 kb NdeI fragment from ZC395, leaving only ZC395.7 intact. In pMQ4, a frameshift was induced in ZC395.7 by degrading the 4 bp overhang of the ApaI site. A frameshift was also induced in pMQ5 by filling in the 2 bp overhang of the NdeI site found in the second exon of ZC395.6. These frameshifts presumably abolish any function of ZC395.7 and ZC395.6 respectively. The dotted lines represent the extent of frameshift that resulted from these alterations.

To establish the splicing pattern of this gene, cDNAs encompassing the 5' and 3' halves of the gene were produced by reverse transcription-PCR and sequenced (FIG. 3).

This revealed that the gene is composed of 9 exons, spans ~2 kb, and produces an mRNA of 1.3 kb. To confirm that this is indeed the gro-1 gene, genomic DNA was amplified by PCR from a strain containing the gro-1(e2400) mutation and the amplified product was sequenced. A lesion was found in the 5th exon, where a 9 base-pair sequence has been replaced by a 2 base-pair insertion, leading to a frameshift (FIG. 3C). FIG. 3C illustrates those residues which differ from wild type are in bold.

The reading frame continues out-of-frame for another 33 residues before terminating.

FIGS. 3A–B illustrate the coding sequence in capital letters, while the introns, and the untranslated and intergenic sequence are in lower case letters. The protein sequence is shown underneath the coding sequence. Position 1 of the nucleotide sequence is the first base after the SL2 trans-splice acceptor sequence. Position 1 of the protein sequence is the initiator methionine. All PCR primers used for genomic and cDNA amplification are represented by arrows. For primers extending downstream (arrows pointing right) the primer sequence corresponds exactly to, the nucleotides over which the arrow extends. But for primers extending upstream (arrows pointing left) the primer sequence is actually the complement of the sequence under the arrow. In both cases the arrow head is at the 3' end of the primer. The sequence of the two primers which flank gro-1 (SHP93 and SHP92) are not represented in this figure. Their sequences are: SHP93 TTTCTGGATTTTAACCTTCC (SEQ. ID. NO:10) and SHP92 GATAGTTCCCTTCGTTCGGG (SEQ. ID. NO:9). The wild type splicing pattern was determined by sequencing of the cDNA. Identification of the e2400 lesion was accomplished by sequencing the e2400 allele. The e2400 lesion consists of a 9 bp deletion and a 2 bp insertion at position 1196, resulting in a frameshift.

Gro-1 is Part of a Complex Operon (FIGS. 3A–3B)

Amplification of the 5' end of gro-1 from cDNA occurred only when the trans-spliced leader SL2 was used as the 5' primer, and not when SL1 was used. SL2 is used for trans-splicing to the downstream gene when two genes are organized into an operon (Spieth et al., Cell 73: 521–532 (1993); Zorio et al., Nature 372: 270–272 (1994)). This indicates that at least one gene upstream of gro-1 is co-transcribed with gro-1 from a common promoter. We found that sequences from the 5' end of the three next predicted genes upstream of gro-1 (ZC395.7, C34E10.1, and C34E10.2) all could only be amplified with SL2. Sequences from the fourth predicted upstream gene (C34E10.3), however, could be amplified with neither spliced leader, suggesting that it is not trans-spliced. The distance between genes in operons appear to have an upper limit (Spieth et al., Cell 73: 521–532 (1993); Zorio et al., Nature 372: 270–272 (1994)), and no gene is predicted to be close enough upstream of C34E10.3 or downstream of gro-1 to be co-transcribed with these genes. Our findings suggest therefore that gro-1 is the last gene in an operon of five co-transcribed genes (FIG. 4).

Nested PCR was used to amplify the 5 end of each gene. SL1 or SL2 specific primers were used in conjunction with a pair of gene-specific primers cDNA generated by RT-PCR using mixed stage N2 RNA was used as template in the nested PCR. FIG. 4A illustrates a schematic of the gro-1 operon showing the coding sequences of each gene and the primers (represented by flags) used to establish the trans-splicing patterns.

Figure 4B:
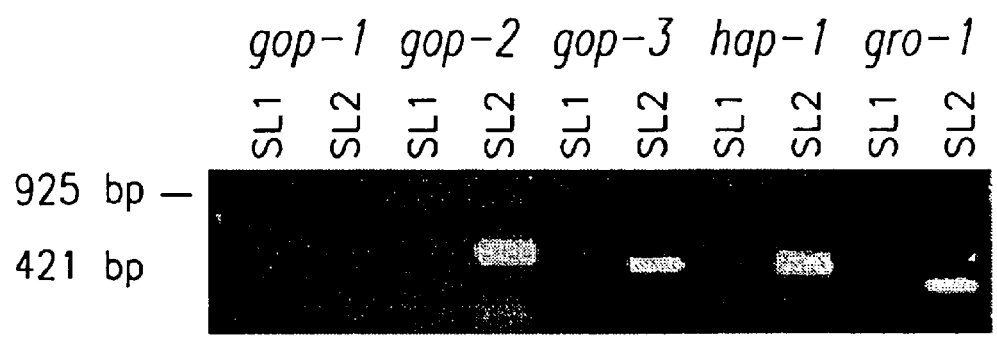
FIG. 4B illustrates the transplicing pattern of the five genes of the gro-1 operon.

FIG. 4B illustrates the products of the PCR with SL1 and SL2 specific primers for each of the five genes. The sequences of the primers used are as follows: SL1: TTTAATTACCCAAGTTTGAG (SEQ. ID. NO:61), SL2: TTTTAACCCAGTTACTCAAG (SEQ. ID. NO:62), SHP141: AAAACTTCTACCAACAATGG (SEQ. ID. NO:30), SHP142: CGTAATCTCTCTCGATTAGC (SEQ. ID. NO:31), SHP143: CCGTGGGATGGCTACTTGCC (SEQ. ID. NO:32), SHP144: TGGATTTGTGGCACGAGCGG (SEQ. ID. NO:33), SHP145: TTGATTGCCTCTC-CTCGTCC (SEQ. ID. NO:34), SHP146: ATCAACATCTGATTGATTCC (SEQ. ID. NO:35), SHP130: CATCCAAAAGCAGTATCACC (SEQ. ID. NO:24); SHP119: ACATCTTTATCCATTTCTCC (SEQ. ID. NO:21), SHP95: TACAGGAATTTTTGAACGGG (SEQ. ID. NO:12), SHP99: ATCGATACCACCGTCTCTGG (SEQ. ID. NO:16).

The gene immediately upstream of gro-1, has homology to the yeast gene HAM1, and we have renamed the gene hap-1. We have established its splicing pattern by reverse transcription PCR and sequencing. This revealed that hap-1 is composed of 5 exons and produces an mRNA of 0.9 kb. We also found that sequences which were predicted to belong to ZC395.7 (now hap-1) are in fact spliced to the exons of C34E10.1. This is consistent with our finding that hap-1 is SL2 spliced as it puts the end of the C34E10.1 very close to the start of hap-1 (FIG. 4).

The Gro-1 Gene Product

Conceptual translation of the gro-1 transcript indicated that it encodes a protein of 430 amino acids highly similar to a strongly conserved cellular enzyme: dimethylallyl-diphosphate:tRNA dimethylallyltransferase (DMAPP transferase). FIG. 5 shows an alignment of gro-1 with the published sequences of the E. coli (P16384) and yeast (P07884) enzymes. Residues where the biochemical character of the amino acids is conserved are shown in bold. Identical amino acids are indicated further with a dot. The ATP/GTP binding site and the 0.30 $C_2H_2$ zinc finger site are predicted and hot experimental. The point at which the gro-1(e2400) mutation alters the reading frame of the sequence is shown. The two alternative initiatior methionines in the yeast sequence, and the putative corresponding methionines in the worm sequence, are underlined.

Database searches also identified a homologous human expressed sequence tag (Genbank ID: Z40724). The human clone has been used to derive a sequence tagged site (STS). This means that the genetic and physical position of the human gro-1 homologue is known. It maps to chromosome 1, 122.8 cR from the top of Chr 1 linkage group and between the markers D1S255 and D1S2861. This information was found in the UniGene database or the National Center for Biotechnology Information (NCBI). We have sequenced Z40724 by classical methods but found that Z40724 is not a full length cDNA clone as it does not contain an initiator methionine nor the poly A tail. We used the sequence of Z40724 to identify further clones by database searches. We found one clone (Genbank ID: AA332152) which extended the sequence 5' by 28 nucleotides, as well as one clone (Genebank ID: AA121465) which extended the sequence substantially in the 3' direction but didn't include the poly A tail. We then used AA121465 to identify an additional clone (AA847885) extending the sequence to the poly A tail. FIG. 8 shows the full sequence with the putative initiator ATG shown in bold and the sequence of Z60724 is shown underlined. A comparison of the conceptual amino acid sequences for GRO-1 (SEQ ID NO:2) and hgro-1p as deduced from SEQ ID NO:3, is shown in FIG. 9. Amino acid identities are indicated by a dot. Both sequences contain a region with a zinc finger motif which is shown underlined.

An additional metazoan homologue is represented by Drosophila EST: Genbank accession: AA816785. In E. colii and other bacteria, the gene encoding DMAPP transferase is called miaA (a.k.a trpX) and is called modS in yeast. DMAPP transferase catalyzes the modification of adenosine 37 of tRNAs whose anticodon begins with U (FIG. 6).

In these organisms the enzyme has been shown to use dimethylallyldiphosphate as a donor to generate dimethylallyl-adenosine (dma$^6$A37), one base 3' to the anticodon (for review and biochemical characterization of the bacterial enzyme see Persson et al., *Biochimie* 76: 1152–1160 (1994); Leung et al., *J Biol Chem* 272: 13073–13083 (1997); Moore and Poulter, *Biochemistry* 36: 604–614 (1997)). In earlier literature this modification is often referred to as isopentenyl adenosine (i$^6$A37).

The high degree of conservation of the protein sequence between GRO-1 and DMAPP in *S. cerevisiae* and *E. coli* suggest that GRO-1 possesses the same enzymatic activity as the previously characterized genes. The sequence contains a number of conserved structural motifs (FIG. 5), including a region with an ATP/GTP binding motif which is generally referred to as the 'A' consensus sequence (Walker et al., *EMBO J* 1: 945–951 (1982)) or the 'P-loop' (Saraste et al., *Trends Biochem Sci* 15: 430–434 (1990)).

In addition, at the C-terminal end of the GRO-1 sequence, there is a C2H2 zinc finger motif as defined by the PROSITE database. This type of DNA-binding motif is believed to bind nucleic acids (Klug and Rhodes, *Trends Biochem Sci* 12: 464–469 (1987)). Although there appears to be some conservation between the worm and yeast sequences in the C-terminus end of the protein (FIG. 5), including in the region encompassing the zinc finger in GRO-1, the zinc finger motif per se is not conserved, in yeast but is present in humans (FIG. 9).

In yeast DMAPP transferase is the product of the MOD5 gene, and exists in two forms: one form which is targeted principally to the mitochondria, and one form which is found in the cytoplasm and nucleus. These two forms differ only by a short N-terminal sequence whose presence or absence is determined by differential translation initiation at two "in frame" ATG codons. (Gillman et al., *Mol & Cell Biol* 11: 2382–90 (1991)). The gro-1 open reading frame also contains two ATG codons at comparable positions, with the coding sequence between the two codons constituting a plausible mitochondrial sorting signal (FIGS. 3 and 5). It is likely therefore that DMAPP transferase in worms also exists in two forms, mitochondrial and cytoplasmic.

It should be noted, however, that the sequence of hgro-1 shows only one in-frame methionine before the conserved ATP/GTP binding site (FIG. 9) As we cannot be assured to have determined the sequence of the full length transcript, it is possible that further 5' sequence might reveal an additional methionine. Alternatively, in humans, the mechanism by which the enzyme is targeted to several compartments might not involved differential translation initiation. In this context, it should be noted that the sorting signals which can be predicted from the sequence of hgro-1p are predicted to be highly ambiguous by the prediction program PSORT II. Furthermore, a conceptual translation of the *Drosophila* sequence (AA816785) predicts only one initiator methionine before the ATP/GTP binding site as well as several in-frame stop codons upstream of this start (FIG. 10), suggesting that no additional upstream ATG could serve as translation initiation site. In the figure, stop codons are indicated by stop, methionines are indicated by Met, and the conserved ATP/GTP binding site is underlined.

Expression Pattern of GRO-1

We have also constructed a reporter gene expressing a fusion protein containing the entire GRO-1 amino acid sequence fused at the C-terminal end to green fluorescent protein (GFP); The promotor of the reporter gene is the sequence upstream of gop-1 (FIGS. 13A–13C), the first gene in the operon (see FIG. 4). The promotor sequence is 306 bp long starting 32 nucleotides upstream of the gop-1 ATG. It is fused at the exact level upstream of gro-1 where trans-splicing to SL2 normaly occurs.

The genes gop-2 (FIG. 14) and gop-3 (FIGS. 15A–15B) are also located in the operon (see FIG. 4), the second and third genes in the operon.

Figure 11A:
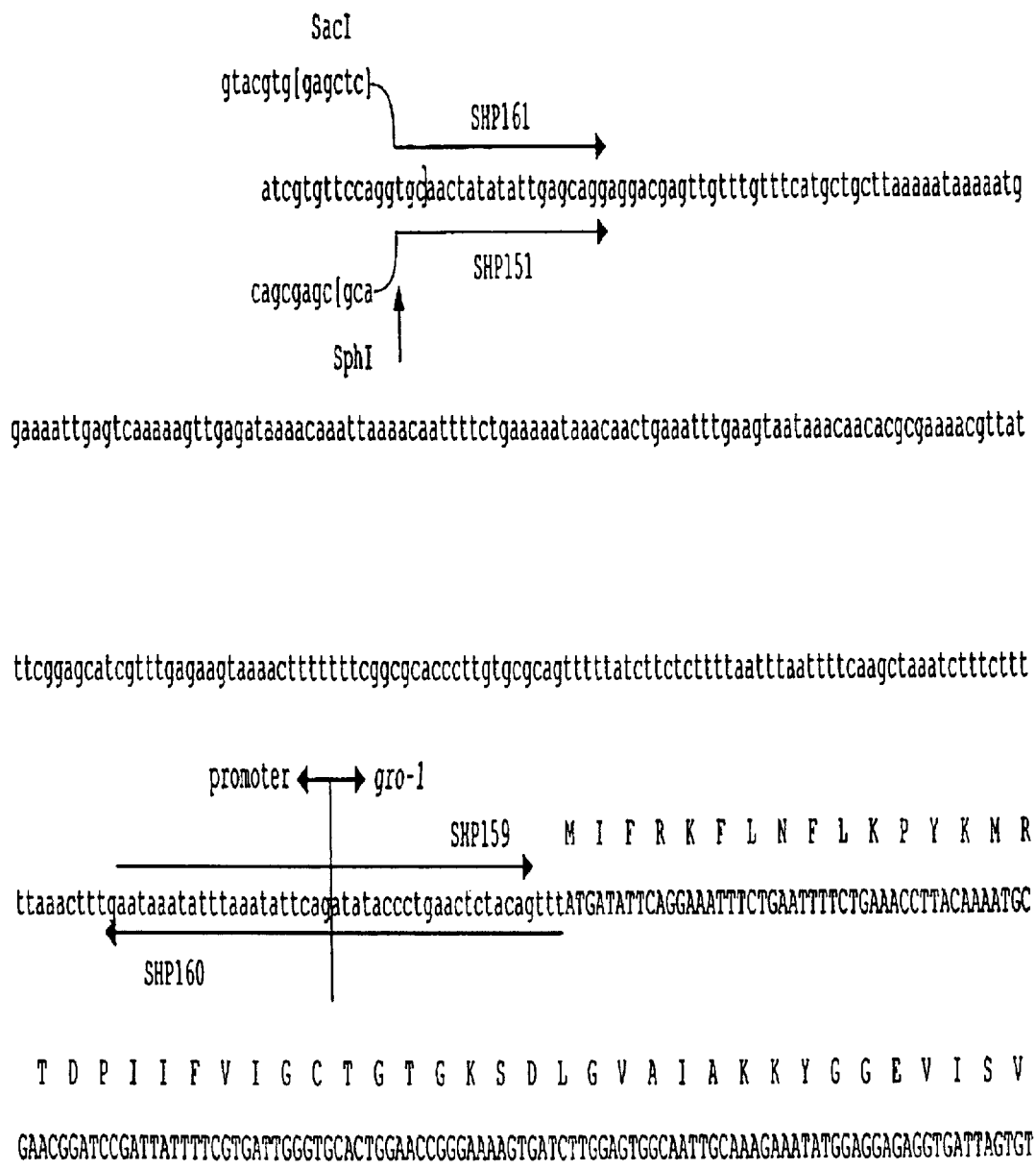
FIG. 11 illustrates the structure of pMQB (SEQ ID NO: 73 and 2)

We first construct the clone pMQ8 in which gro-1 is directly under the promoter for the whole operon using the hybrid primers SHP160 (SEQ. ID. NO, 38) and SHP159 (SEQ. ID. NO:37) and the flanking primers SHP161 (SEQ. ID. NO:39) and SHP162 (SEQ. ID. NO:40) in sequential reactions each followed by purification of the products and finally cloning into pUC18 (FIG. 11).

Primers SHP151, (SEQ. ID. NO:36) and SHP170 (SEQ. ID. NO:44) where then used to amplify part of the insert in pMQ8 and clone in pPD95.77 (gift from Dr Andrew Fire) which was designed to allow a protein of interest to be transcriptionally fused to Green Fluorescent Protein (GFP) (FIG. 12).

The reporter construct fully rescues the phenotype of a gro-1(e24.00) mutant upon injection and extrachromosomal array formation, indicating that the fusion to the GFP moiety does not significantly inhibit the function of GRO-1. Fluorescent microscopy indicated that gro-1 is expressed in most or all somatic cells. Furthermore, the GRO-1::GFP fusion protein is localized in the mitochondria, in the cytoplasm as well as in the nucleus.

The Hap-1 Gene Product (FIG. 16)

hap-1 is homologous: to the yeast gene HAM1 as well as to sequences in many organisms including bacteria and mammals (FIG. 7).

The origin of the worm and yeast sequence is as described above and below. The human, sequence was inferred from a cDNA sequence assembled from expressed sequence tags (ESTs); the accession numbers of the sequences used were: AA024489, AA024794, AA025334, AA026396, AA026452, AA026502, AA026503, AA026611, AA026723, AA035035, AA035523, AA047591, AA047599, AA056452, AA115232, AA115352, AA129022, AA129023, AA159841, AA160353, AA204926, AA226949, AA227197 and D20115. The *E. coli* sequence is a predicted gene (accession 1723866).

Mutations in HAM1 increase the sensitivity of yeast to the mutagenic compound 6-N-hydroxylaminopurine (HAP), but do not increase spontaneous mutation frequency (Nostov et al., *Yeast* 12: 17–29 (1996)). HAP is an analog of adenine and in vitro experiments suggest that the mechanism of HAP mutagenesis is its conversion to a deoxynucleoside triphosphate which is incorporated ambiguously for dATP and dGTP during DNA replication (Abdul-Masih and Bessman, *J Biol Chem* 261 (5): 2020–2026 (1986)). The role of the Ham1p gene product in increasing sensitivity to HAP remains unclear.

Explaining the Pleiotropy of MiaA and Gro-1

Mutations in miaA, the bacterial homologue of gro-1, show multiple phenotypes and affect cellular growth in complex ways. For example, in *Salmonella typhimurium*, such mutations result in 1) a decreased efficacy of suppression by some suppressor tRNA, 2) a slowing of ribosomal translation, 3) slow growth under various nutritional conditions, 4) altered regulation of several amino acid biosynthetic operons, 5) sensitivity to chemical oxidants and 6) temperature sensitivity for aerobic growth (Ericson and Björk, *J. Bacteriol.* 166: 1013–1021 (1986); Blum, *J. Bacteriol.* 170: 5125–5133 (1988)). Thus, MiaAp appears to be important in the regulation of multiple parallel processes of cellular physiology. Although we have not yet explored the cellular physiology of gro-1 mutants along the lines which have been pursued in bacteria, the apparently central role of miaA is consistent with our findings that gro-1, and the other genes with a Clk phenotype, regulate many disparate physiological and metabolic processes in *C. elegans* (Wong et al., *Genetics* 139: 1247–1259(1995); Lakowski and Hekimi, *Science* 272: 1010–1013 (1996); Ewbank et al., *Science* 275: 980–983 (1997)).

In addition to the various phenotypes discussed above, miaA mutations increase the frequency of spontaneous mutations (Connolly and Winkler, J *Bacteriol* 173(5): 1711–21 (1991); Connolly and Winkler, *J Bacteriol* 171: 3233–46 (1989)). As described in the previous section we have preliminary evidence that gro-1(e2400) also increases the frequency of spontaneous mutations in worms.

How can the alteration in the function of MDAPP transferase result in so many distinct phenotypes? Bacterial geneticists working with miaA have generally suggested that this enzyme and the tRNA modification it catalyzes have a regulatory function which is mediated through attenuation (e.g. Ericson and Björk, *J. Bacteriol.* 166: 1013–1021 (1986)). Attenuation is a phenomenon by which the transcription of a gene is interrupted depending on the rate at which ribosomes can translate the nascent transcript. Ribosomal translation is slowed in miaA mutants, and thus, through an effect on attenuation, could affect the expression of many genes whose expression is regulated by attenuation.

gro-1(e2400) also produces pleiotropic effects and, in addition, displays a maternal-effect, suggesting that it is involved in a regulatory process (Wong et al., *Genetics* 139: 1247–1259 (1995). However, attenuation involves the co-transcriptional translation of nascent transcripts, which is not possible in eukaryotic cells were transcription and translation are spatially separated by the nuclear membrane. If the basis of the pleiotropy in miaA and gro-1 is the same, then a mechanism distinct from attenuation has to be involved. Below we argue that this mechanism could be the modification by DMAPP transferase of adenine residues in DNA in addition to modification of tRNAs.

A Role for Gro-1 in DNA Modification?

We observed that gro-71 can be rescued by a maternal effect, so that adult worms homozygous for the mutation, but issued from mother carrying one wild type copy of the gene display a wild type phenotype, in spite of the fact that such adults are up to 1000 fold larger than the egg produced by their mother. It is unlikely that enough wild type product can be deposited by the mother in the egg to rescue a adult which is 1000 times larger. This observation suggests therefore that gro-1 can induce an epigenetic state which is not altered by subsequent somatic growth. One of the best documented epigenetic mechanisms is imprinting in mammals (Lalande, *Annu Rev Genet* 30: 173–196 (1996)) which is believed to rely on the differential methylation of genes (Laird and Jaenisch, *Annu Rev Genet* 30: 441–464; Klein and Costa, *Mutat Res* 386: 103–105 (1997)). Modification of bases in DNA have also been linked to regulation of gene expression in the protozoan *Trypanosoma brucei*. The presence of beta-D-glucosyl-hydroxy-methyluracil in the long telomeric repeats of *T. brucei* correlates with the repression of surface antigen gene expression (Gommers-Ampt et al., *Cell* 75: 112–1136 (1993); van Leeuwen et al., *Nucleic Acids Res* 24: 2476–2482 (1996)).

gro-1 and miaA increase the rate of spontaneous mutations, which is generally suggestive of a role in DNA metabolism, and can be related to the observation that methylation is linked to spontaneous mutagenesis, genome instability, and cancer (Jones and Gonzalgo, Proc. Natl. Acad. Sci. USA, 94: 2103–2105 (1997)).

Does gro-1 have access to DNA? Studies with mod5, the yeast homologue of gro-1, have shown that there are two forms of Mod5p, one is localized to the nucleus as well as to the cytoplasm, and the other form is localized to the mitochondria as well as the cytoplasm (Boguta et al., *Mol. Cell. Biol.* 14: 2298–2306 (1994)). The nuclear localization is striking as isopentenylation of nuclear-encoded tRNA is believed to occur exclusively in the cytoplasm (reviewed in Boguta et al., *Mol. Cell. Biol.* 14: 2298–2306 (1994)). Furthermore, studies of a gene maf1 have shown that when mod5 is mislocalized to the nucleus, the efficiency of certain suppressor tRNA is decreased, an effect known to be linked to the absence of the tRNA modification (Murawski et al., *Acta Biochim. Pol.* 41: 441–448 (1994)). Finally, as described in the previous section, gro-1 contains a zinc finger, a nuclei acid binding, motif. The zinc finger could bind tRNAs, but as it is in the C-terminal domain of gro-1 and human hgro-1 that has no equivalent in miaA, it is clearly not necessary for the basic enzymatic function. We speculate that it might be necessary to increase the specificity of DNA binding in the large metazoan genome. It should also be noticed that the second form of Mod5p which is localized to mitochondria also has the opportunity to bind and possibly modify DNA as it has access to the mitochondrial genome. See the previous section entitled "A role for gro-1 in a central mechanism of physiological coordination" for an alternative possibility as to the function of GRO-1 in the nucleus.

MiaA and Gro-1 are Found in Complex Operons

We have found that gro-1 is part of a complex operon of five genes (FIG. 4). It is believed, that genes are regulated coordinately by single promoters when they participate in a common function (Spieth et al., *Cell* 73: 521–532 (1993)). In some cases, this is tit well documented. For example, the proteins LIN-15A and LIN-15B which are both required for vulva formation in *C. elegans*, are unrelated products from two genes transcribed in a common operon (Huang et al., *Mol Biol Cell* 5 (4): 395–411 (1994)) One of the genes in the gro-1 promoter is hap-1, whose yeast homologue has been shown to be involved in the control of mutagenesis (Nostov et al., *Yeast* 12: 17–29 (1996)). Under the hypothesis that gro-1 modifies DNA, it suggest an involvement of hap-1 in this or similar processes. The presence in the same operon also suggest that all five genes might collaborate in a common function. The phenotype of gro-1 suggests that this function is regulatory. In this context, it should be noted that miaA also is part of a particularly complex operon (Tsui and Winkler, *Biochimie* 76: 1168–1177 (1994)), although, except for miaA/gro-1, there are no other homologous genes in the two operons.

A Role for Gro-1 in a Central Mechanism of Physiological Coordination

We have speculated that the genes with a Clk phenotype might participate in a central mechanism of physiological coordination, probably including the regulation of energy metabolism clk-1 encodes a mitochondrial protein (unpublished observations), 4and its homologue in yeast has also been shown to be mitochondrial (Jonassen, T (1998) *Journal of Biological Chemistry* 273: 3351–3357). The yeast clk-1 homologue is involved in the regulation of the biosynthesis of ubiquinone (Marbois, B. N. and Clarke, C. F. (1996) *Journal of Biological Chemistry* 271: 2995–3004). Ubiquinone, also called coenzyme Q, is central to the production of ATP in mitochondria., In worms, however, we have found that clk-1 is not strictly required for respiration. How might gro-1 fit into this picture?

One link is that dimethylallyldiphosphate is known to be the precursor of the lipid side-chain of ubiquinone. In bacteria, ubiquinone is the major lipid made from DMAPP.

In eukaryotes cholesterol and its derivatives are also made from DMAPP. Interestingly, *C. elegans* requires cholesterol in the growth medium for optimal growth. This link, however, remains tenuous in particular in the absence of an understanding of the biochemical function of CLK-1.

In several bacteria, the adenosine modification carried out by DMAPP transferase is only the first step in a series of further modification of this base (Persson et al., *Biochimie* 76: 1152–1160 (1994)). These additional modifications have been proposed to play the role of a sensor for the metabolic state of the cell (Buck and Ames, *Cell* 36: 523–531 (1984); Persson and Björk, *J. Bacteriol.* 175: 7776–7785 (1993)). For example, one of the subsequent steps, the synthesis of 2-methylthio-cis-ribozeatin is carried out by a hydroxylase encoded by the gene miaE. When the cells lack miaE they become incapable of using intermediates of the citric acid cycle such as fumarate and malate as the sole carbon source.

Another link to energy metabolism springs from the recent biochemical observations of Winkler and coworkers using purified DMAPP transferase (*E. coli* MiaAp) (Leung et al., *J Biol Chem* 272: 13073–13083 (1997)). These investigators observed that the enzyme in competitively inhibited by phosphate nucleotides such as ATP or GTP. Furthermore, using their estimation of $K_m$ of the enzyme and its concentration in the cell, they calculate that the level of inhibition of the enzyme in vivo, would exactly allow the enzyme to modify all tRNAs but any further inhibition would leave unmodified tRNAs. This suggests that the exact level of modification of tRNA (or of DNA) could be exquisitely sensitive to the level of phosphate nucleotides. Superficially, this is consistent with the phenotypic observations. The state of mutant cells which lack DMAPP transferase entirely would be equivalent of cells where very high levels of ATP would completely inhibit the enzyme. Such cells might therefore turn down the ATP generating processes in response to the signal provided by undermodified tRNAs (or DNA).

More generally, GRO-1 could act in the crosstalk between nuclear and mitochondrial genomes. The nuclear and mitochondrial genomes both contribute gene products to the mitochondrion energy-producing machinery and these physically separate genomes must therefore exchange information somehow to coordinate their contributions (reviewed in Poyton, R. O and McEwen J. E. (1996) *Annu. Rev. Biochem.* 65: 563–601) Furthermore, the energy producing activity of the mitochondria is essential to the rest of the cell, and the needs of a particular cell at a particular time must be somehow convey to the organelle to regulate its activity. GRO-1 could participate in this coordination in the following manner. GRO-1 is found in three compartments, the nucleus, the cytoplasm and the mitochondria (see above), and thus has the opportunity to regulate gene expression in more that one way. How could its action coordinate gene expression between compartment? GRO-1 could partition between the mitochondria and the nucleus and its relative distribution could be determined by the amount of RNA (or mtDNA) in the mitonchodria (Parikh, V. S. et al. (1987) *Science* 235: 576–580). For example, if the cell is rich in mitochondria, much GRO-1 will be bound there which could result in a relative depletion of activity in the cytoplasm with regulatory consequences on the translation machinery. Binding of GRO-1 in the nucleus could have similar consequences and provide information about nuclear gene expression to the translation machinery.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

SEQUENCE LISTING

<160> NUMBER OF SEQ ID NOS: 77

<210> SEQ ID NO 1
<211> LENGTH: 14458
<212> TYPE: DNA
<213> ORGANISM: C. elegans

<400> SEQUENCE: 1

```
gcaaaatttg ctaagatgaa gcgccggctt gttacattgc ttttcagagt cgattggttc      60
aaaattgtca attttatcca aaatagagtg cattgtgtgt acaataacta aagaatcatc     120
catatctggt ccaacacaac attgatggaa tactggatca attgtctaaa aaaatatcaa     180
tagaataatg aaacattttc agaattcatt accgtcaatg tcagatagtc attccttgag     240
tattttgtgg atgctttgaa aattcttcgc tgggccatat ctgttggata atctgaaaaa     300
cgcaataaat ttcatcgaaa atgcctatta aattgaatta ccttcttctt catcatttcc     360
taacaattca tgctcttttt gtgcttgact tgtgaccaat tctttaaatt caattaaatc     420
gtcaatatcc ttttgtacta aatccatctt gatattcaat atatctttgt cagtatagta     480
ttcagcgtat ctgaaatttc gaatttattt ttctaattcc caagaaaaat aattaataag     540
aataccttaa cgaattatta tccaatatat catcatttgc cacatctgga agacgctgag     600
```

-continued

| | |
|---|---|
| gaactgtttg agcagcttgg aggtagtcgt catcgtctct ggaaattgtt attttcaatt | 660 |
| tcaaaaaaaa aactttactt acgaaatata ctcatttgat gcaatccacg gatcaaaacg | 720 |
| acgtctttgc atctttgaat cattttccgc atggcaccgc atcacttctt tcttatgatt | 780 |
| attttctaac gtttttgaaa attcgacgtg ctcttcacaa cggccgccat gtttcgcaag | 840 |
| ttcttctttt gatcgtatct aaaatttaa atttgaaaaa aagcttacta tcaaattttc | 900 |
| gtatttttc tcacctgctt acaccgaaca agcgttcgat acgaagcata attacattgt | 960 |
| ccatacttat ttttgtcgta ttcattggca acaagacgga atcgtgttcc aggtgcaact | 1020 |
| atatattgag caggaggacg agttgtttgt ttcatgctgc ttaaaaataa aaatggaaaa | 1080 |
| ttgagtcaaa aagttgagat aaaacaaatt aaaacaattt tctgaaaaat aaacaactga | 1140 |
| aatttgaagt aataaacaac acgcgaaaac gttattcgg agcatcgttt gagagtaaa | 1200 |
| actttttttc ggcgcaccct tgtgcgcagt ttttatcttc tcttttaatt taattttcaa | 1260 |
| gctaaatctt tcttttaaa ctttgaataa atatttaaat attcagaatg caccaataaa | 1320 |
| cctggaacaa aatcgataat gttccgcaag cttggttctt ctgggtcact atggaagccg | 1380 |
| aaaaatccgc attctttgga atacctcaaa tatttacaag gagtgctcac aaaaaatgag | 1440 |
| aaagttacgg aaaacaataa gaaaatatta gtagaagcat tacgagctat cgcagaaatt | 1500 |
| ctcatttggg gcgatcagaa tgatgcttcg gttttttgagt gagttttttt ccaatgtttt | 1560 |
| ttttcaaatc tgatgttgaa tttcagtttc ttccttgagc ggcaaatgct tctttatttc | 1620 |
| ttgaaaatta tggaacaagg aaacacacca ctaaatgtac aattactgca gactttgaac | 1680 |
| attttattcg aaaatattcg acatgaaact tcactttgta agtttttat atggattttc | 1740 |
| gcttaaaatt gccagttttc agatttcctt ctaagtaaca atcatgtaaa ctcgattatt | 1800 |
| tcccacaaat tcgatttaca aaatgatgag atcatggctt actacattag ttttctgaaa | 1860 |
| actctttcat ttaaactgaa tccagctaca atccacttct tcttcaatga aacgactgaa | 1920 |
| gaatttccat tgttggtaga agttttgaag ctttataatt ggaatgaatc aatggttcga | 1980 |
| attgctgtta gaaatattct tttaaatatt gtgagagttc aagatgattc aatgattat | 2040 |
| ttcgctatca agcatacaaa agttagtaga aaattatttt gaaaaggtgt atttaagcaa | 2100 |
| taaatattac aggaatatct atcggagtta atagattctc tagttggtct ctcacttgaa | 2160 |
| atggacacat ttgtacgatc tgctgagaat gtgttagcta atcgagagag attacgagga | 2220 |
| aaagtggatg atttaattga tttgattcat tatattggtg aactattgga tgtggaagct | 2280 |
| gtcgccgaaa gtttatcaat tttaggtcag ttttactgct ggaaaatcaa gttttttaatg | 2340 |
| ttaaattttc agtaacaaca cgatacttaa gccctctatt actttcaagt atatcaccaa | 2400 |
| gaagagataa tcattcactt ctactcactc cgatttctgc gttatttttt ttctctgaat | 2460 |
| ttttattggt gagttttaac atttaaaatt acatttttct aatttattta ttttttcagat | 2520 |
| agttcgtcac catgaaacaa tatatacatt tttatcatct ttcctatttg acactcagaa | 2580 |
| tactttgacg acccattgga tacgtcataa tgagaaatat tgcttagaac cgattacatt | 2640 |
| atcatcacca accggagaat atgtgaatga agaccagtaa gagctgaaat tttaaaattt | 2700 |
| ttgctttgaa tatagtattt tcagcgtatt tttcgatttt ctactggaag catttgattc | 2760 |
| cagtcaagca gacgattcga aggcattcta tggattaatg ctgatttatt caatgtttca | 2820 |
| gaataatggt gagttttaaa aaattgattt gttaaattaa aatttccatt tccaataact | 2880 |
| cctcttcaga cagtaagttt tcaatgttgt aaagttcctg ttcatctgtg atcgttttct | 2940 |
| tcatttttttt agttttgcat gaacagtttt caaattttt tgatatcata cagtaaatat | 3000 |

-continued

```
cgtcatccag ataattttct atttaaaaaa aatgaataaa aagagggcgc gcagaaattg    3060
ccgaagtaat gtaaatttaa agggacacat gcgtagcttg ttgtgtgggt ctcgccgcgc    3120
tttgtttgat ttatcttgtt ttctgctcaa agagctgttt ttattttagc gttgaatgct    3180
tttttaccgt tctcatcggc ttttttaatag gaatatttaa aaaaaaaggt ttaataaatc    3240
ttcgttttta caaatccat ctaagatttg catttgtgaa gctcaacaag taaagtttta    3300
agtaacattg ttttttaaaa aacaattgaa ccaaattttg ccgaaacatt aataacatga    3360
cgatactcta taaatattc ctcttttcaa aataaatttt caaaaaaaat ccattttttca    3420 gccgatgttg gagaacttct atctgctgcc aacttcccag tgctcaaaga atcaacgaca    3480
acttcattag ctcaacagaa tcttgctcgt ctccgaatag catctacgtc ttccatatca    3540
aagcgaacga gagctatcac tgaaattgga gtagaagcga ccgaggaaga tgagattttt    3600
catgatgttc ctgaagaaca aacgttggta agtaaataaa tcaacattga ttgttacaca    3660
aactttaata tttttaaatt tgaaaatttt cttcaaagtg ctcaaaaatc ctgtcgaaaa    3720
ttacaggaag atctggtgga tgatgtattg gttgatactg aaaattcagc aataagtgat    3780
ccagaagtga gtagaaaacg tgcatgtatt aattattaaa aaaaaaatat agttttcccc    3840
agttttcctt gacctaaaac tcagcaattt cagcctaaaa acgtggagtc agaatctcgt    3900
tctcgatttc aatctgctgt tgatgagctt ccacctccgt cgacttctgg atgtgatggt    3960 cgacttttttg atgcactttc atcgattatc aaagcagttg gaacagatga caatcgaatt    4020
cgaccaatta cattggaact tgcatgtctt gtaattcggc aaattttaat gactgttgat    4080
gatgaaaaag taagattaca aattcaaat tgagcaaaat cagaatctaa atttcataaa    4140
ttgttcaggt acataccagt ttaacgaaat tatgcttcga agttcgtcta aaactttat    4200 catcaattgg acaatatgtt aatggagaga atctgttttt ggagtggttt gaggatgaat    4260
atgcagaatt tgaagtaagc caagaggtcc gaaaataatt taattcatcc ttttttattca    4320 ggtgaatcac gtgaatttcg atataatcgg tcacgaaatg cttcttcctc cagctgcaac    4380 tcctcttttcg aatctgctac ttcataagcg attgcccagt ggatttgaag aacgaataag    4440
aactgtagga aacttttttaa atttgaaaat taattatata tatatttgca gcaaatcgta    4500
ttctacctac atattcgaaa attggaacga gatttgaccg gtgaaggaga cacagaatta    4560
cctgtgagag tgttgaattc tgatcaggaa ccagttgcca tcggtgattg tattaattta    4620
cgtgagttca tctgcataga aaacaccata tttctactca aattaacaat ttcagataa    4680 ttcggatctt ctatcctgca ctgtggttcc tcaacaacta tgttctcttg gaaaacctgg    4740
tgatcgtctt gctcgattcc ttgtcactga tagacttcaa ttaattcttg tcgaaccgga    4800
ttctcgaaaa gccggatggg caattgttcg attcgtagga cttcttcaag atacaacaat    4860
taatggagat tctacggatt cgaaagtttt gcatgttgtg gtggaagggc aaccctcgag    4920
aattaaggta agaatactaa cgggaaaaaa aaatcaaaaa attacttctg tttcagaaaa    4980
gacatccggt tttaactgca aagttcatat tcgatgatca cattcggtgt atggcagcaa    5040
agcaacggct caccaaggta acggaaaaaa taaccaaaaa gacggaaagt tattgtaaat    5100
ggacgaaatc ggcgaaatta attgaaaacg tttgaatttg ccgctaaaac caaacgaaaa    5160
ccaaacgaaa gcgaaattta actatccctt caggtagaat atacatttta tttctcttta    5220
tagggtcgcc aaacagcacg tggtctgaaa cttcaggcga tatgttcagc tcttggagtt    5280
ccacgtatcg atccagcgac aatgacgtca tcaccacgaa tgaatccatt cagaattgtg    5340
```

```
aaaggatgcg caccgggaag tgtacgaaaa actgtttcca catcatcatc gtcaagccaa    5400
ggacgtcccg gacattattc tgcaaatctt agatcagcat ctagaaatgc aggaatgata    5460
ccagatgatc caactcaacc gagtagttct tcggaaagaa gatcctaggg atcaatatct    5520
cttcagtttc atcattttat gctgtaaatt gtatttaagt attcctattc tttgtagtac    5580
tgtatttaca catcgtctag ttaaaatcac aaatctccga aaaacaaac cagtgaacat     5640 gtgatatttc tcttgcccat agttctcttt tttttttgaa acaaaaacaa ttacttttat    5700
gctcacctat tcgagccata tttttttccc aattaccggt tgtttatttt aatttctttt    5760 tttttctgt aaatctactt tattttaaa actgcatttg agattgtgta tattttttca      5820
aaatggttca aatgccgaat ctatctactt tttaatcatt attcaaacag aaaaaccgat    5880
tatttattca gattctcaaa aatggctgaa aaagctgaaa atcttccatc ttcttcggcc    5940
gaagcttcag aagagccatc acctcaaact ggaccaaatg tgaatcaaaa accatcgatt    6000
ttggttcttg gaatggctgg ttctggaaaa acgacatttg ttcaggtaac tttcattcaa    6060
ttttgagagt tttcaaacat tactattttc agcgtctcac agcattccta catgctcgta    6120
aaacacctcc atatgtgatt aatctggatc cggcagttag caaagtacct tatccagtga    6180
atgttgacat tcgagatact gtgaaataca aggaagttat gaaagaattc ggaatgggac    6240
caaatggagc aattatgaca tgtcttaacc tgatgtgtac tcgttttgat aaagtaattg    6300
agttgattaa taagagatct tctgatttct cagtttgtct tcttgatact cctggacaaa    6360
ttgaagcatt cacttggagt gctagtggat ctattatcac tgattcattg gcaagtagcc    6420
atcccacggt aagggatttt gatttatgaa atctgcttga atgaaaaaa gattctaata    6480 aattttgac tttaaacat tttttacagt tatatttggt ctattttcta tcattaaaag      6540
caaaatgaaa agtcgattct actccatatt tattaatttc gactttttcag gtggtaatgt   6600 acattgtgga ttccgctcgt gccacaaatc caactacatt catgtccaat atgctctacg    6660
catgttccat tctctaccgt accaaacttc cattcattgt cgttttcaac aaagctgata    6720
ttgtcaaacc aacatttgca ctcaaatgga tgcaagattt cgaaagattt gatgaagctt    6780
tagaggatgc cagaagcagt tatatgaatg atttgagtcg ttcattgagt ctcgttcttg    6840
atgaattcta ttgcggactg aaaacaggtt tttattcgaa ataaaacctt ttttaaataa    6900
taaatttcag tttgcgtcag ttctgcaact ggagaaggat tcgaagatgt aatgacagca    6960
atcgatgaaa gtgttgaagc atacaaaaaa gaatatgttc caatgtatga aaagtgttg     7020 gctgagaaaa aactattgga tgaggaggag agaaagaaaa gagatgaaga ggtaattgta    7080
gtaatttaat tctgattatc ttcaaatttt cagactctga aaggaaaagc tgttcacgac    7140
ctgaacaaag tcgccaatcc cgacgaattt ctggagtcgg agttgaattc aaaaatcgat    7200
agaattcatt tgggcggagt cgatgaagag aatgaggagg atgctgaact cgaaagatcc    7260
tgattttctt tttgtttttg aattttattt ctattttgat ccctgtttac ttcttattgt    7320 tctcatttg ttgcgttgtt ttacatttta ctcattttg cataaacttg ttgcaaaaat      7380
caatataatt tttgatctgg aaatggtttt aaaccttaac ctttcatata ttaataattt    7440
tttttcaaaa aaacgttcta aaaaggttcc tcattttttc aatataggaa attttgaaga    7500
tcttttccaa aaatgaggtt cttcgcttga aaagccaaca tttaaaacct tttttttcc     7560 agaaacctag tggttaatgt ctgaaaagac gttccacaag gcacagacca tccgtgcaaa    7620
ggcatccgga gtgccttcaa tcgtcgaagc tgtacagttt catggagttc gcatcacaaa    7680
aaacgatgct ttggttaagg aggtactacc caaatttcaa aatgttgcac aattcaattg    7740
```

-continued

```
aaaatataaa ttgtgaatta aattcaactt acatgttttt tcaggttttcc gaattataca      7800 gaagtaaaaa tctagatgaa cttgttcata actctcatct ggcggctcgt catcttcaag      7860
aagttggatt aatggataat gcagttgctc taattgatac atctccaagc tcaaatgaag      7920
gatatgttgt caatttccta gttcgagaac caaaatcatt cactgctgga gtcaaagcag      7980
gagtttcaac gaatggagat gcggatgtca gtttaaatgc cggaaaacaa agtgttggag      8040
gacgaggaga ggcaatcaat acacagtata catatactgt aaaggtaagg acgagagttg      8100
gcactgccag tttggcatgt tctcccaata ttttttaatt ataaaatttg gaagtataaa      8160
aaaatgtttg cttcatctaa aaatagcctt tttcacatga aaaaaattga aaaaagtgc       8220 tcaaaaattt cagaaatttc caattttcaa acaattttgg agaactttca aaaatttttc     8280
caactgaaat taaagctata ttctatcact aaatttata caagtcttaa gagaaaatga     8340
tgaagtggct catttgtag aatttcctaa aaaataatat cttcagggcg atcactgctt      8400
caacatttcc gcaatcaaac cattcctggg atggcaaaaa tattcgaatg tatcagcgac      8460
tctataccgt tcacttgcac atatgccatg gaatcaatca gatgttgatg agaatgcagc      8520
tgttcttgca tataatggac aactatggaa tcaaaagctt ttgcatcaag tcaaattgaa      8580
tgcggtaaag tattataagt gttttgtcca aactatgata cagttcttca gatatggaga      8640
acacttcgtg ccactcgaga tgccgcattt tcagttcgtg aacaagccgg acacactttg      8700
aaattctcgt tggagaatgc tgtagctgtt gatacaagag atagacctat tcttgcaagt      8760
cgtggaattc ttggtaagag taacaacgac tatttttaaa aaatatcttt ttcgaaaaaa      8820
ttacgaacga aaaaaaactg tattatgtac ccaaacgcga aattttgcag ttcttgcgcg      8880
ttcttgttga taaaaaatat gtaaaaaatt ggaaaaacta cgaaaagtcg ataaaaattc      8940
cgtaccaacc ggaaaatgtt tcattaattt ctcttccttt tttcagctcg ttttgctcaa      9000
gagtacgcag gagtatttgg tgatgcgtca tttgtgaaga atacattaga tttacaggta      9060
acaaccttat ttcaacaatt atttcaaatt ctattaaaaa taattccagg cagctgcccc      9120
tcttccactc ggtttcattc ttgccgcctc attccaagcg aaacatttga aaggactcgg      9180
agatcgagaa gttcatattt tggatagatg ttatttgggt ggacaacagg atgttcgagg      9240
atttggtctg aatactattg gagtgagttt taacgaaatt ctcttgaaag tcaaataatc      9300
attttcaggt taaagcagat aacagttgtc ttggaggagg tgcttcactt gctggtgtcg      9360
ttcatttgta tcggccattg attccaccaa atatgctatt tgcacacgca ttccttgcat      9420
ctggaagtgt tgcatcagtt cattccaaaa atttggtgca acaattacag gatactcaac      9480
gagtatcagc cggatttggt gagtttgaaa tttaggaaac atttggatga aatgtatttt      9540
ttaaaaatag atcagcttta tttatttgaa aaaaacgct cattaatcaa tagtgatagt       9600
tccattctga gtttcttctt cttcctcgcg gaatacaatt tttgacttgt tcgcatcctt      9660
cttgtgtact ttgtcaccaa tcttctcatc aactaaatct cgaaactgaa aaaatttcaa      9720
aattattcca aaaatatttg atgcagacta ccttttttgat ggcttctggt acgtttctag     9780
cgtcgaatgg attggctcct ccaataatta agtctcgtt cggtagttta gccagacgga      9840
cggtgtgctt caacatttt ctaattaatc tatttcaatt caagtcactc actctctctt       9900
gacgtcttct tctatattcc aagaactctg cagaaaatcc gtgtccgcct tgtgtgtttc      9960
tagttggcgt cggaggattc acgggtccaa gacgaatgga tgtctaaaaa atgttatatt     10020
tttgcataaa gaaaacacca taccttcacc acttttttgag ttgtgggcgt tctgaatgga    10080
```

-continued

```
attgatcgat tattattgct ctttcttgat ttgcttctat cagctgcgta atgaggtgtt     10140
ctaaagatca gctttaattc atttggacaa gtgctcctct aataaactta ccctgtactc     10200 attttttgaaa cgatttacga tgataagatt gaaagtggaa gttaaattta gtctttcaaa    10260
gttgaaataa aatcttcata aataaataaa tttaaatgaa agattaaata aattaacgtt     10320
cacgtagtta aaaaaataat ttaaatctta acttctaata aaaaatctca attttccagg     10380
actcgcattc gtgttcaaaa gtattttccg gctggaactc aactacacgt atccattgaa     10440
atatgtgctc ggcgattcat tgctcggtgg attccatatt ggagctggtg tcaacttctt     10500
gtagagatta attggatgca agcacccctc aaaaagattt ttttgaaaaa cgataaattc     10560
acagaatttc agttcttttt ctccccctt tattgttatt ttcatcgtaa tgctgtgcta     10620
gaagtcagag taaatgtgag tttttttgtg ttctaggaat tccatttttt caggaagcaa    10680
atttaataaa aattatcgaa tttcttgctc taaagatgtt gtacatttta tggaaatgtt    10740
cgtatagtaa ttcgaacact ttatatttct cgttttaaaa ctgtcggtgt tttatagtaa    10800
actatcttca gaaaaaaatg agcctacgaa aaatcaattt cgtaactgga acgtgaaga    10860 agcttgaaga agtcaaggct attttgaaga atttcgaggt aaaatatatt tgatattatt    10920
cgaacgcgaa attttgcgcc aaaagtacga tgcctggtct caacacgaca atattttgtt    10980
aaatacaaac gaatgtgcgc cttcaaagaa aagtttcaat ctttcgttgc cgtggagata    11040
tttttagagt ttttgtttaa attatatatt tgtcgtatcg aaaccgggta ccgtaatcaa    11100
tcaattaaat attttcaggt ttcaaacgtg gatgtcgatt tggatgaatt ccaaggagaa    11160
cccgaattta ttgccgaaag aaagtgccgt gaggctgttg aagctgtaaa agggcccgtt    11220
ttggtatgga aaattgtatt tgttctaaaa attgtcaaat ttcaggtcga agacacaagt    11280
ttatgcttca acgcaatggg cggtcttcct ggaccttata tcaagtggtt tttgaagaat    11340
ttgaaaccag aaggactaca taatatgcta ggtaaatatt ttaattttt gaaaaaactt     11400 attttttcagc cggattttct gacaaaaccg cctatgctca atgcatcttt gcgtacactg    11460
aaggactcgg aaaacctatt catgtatttg ctggtatgat tttttgaatt taattctta    11520 attttatatg ttaatttagt tgtttcattc ctcaatttat gagagatttt tttttcaatt    11580
tttctatttc aggaaaatgt cctggtcaaa ttgttgctcc acgtggtgat actgcttttg    11640
gatgggatcc atgcttccag ccagatggtt ttaaagaaac attcggagaa atggataag    11700 atgtaaaaaa tgaaatttct catcgtgcaa aggctctgga actcctcaag gaatattttc    11760
agaataatta aattatttt tctcatctat gcaatttctt gaaaatttgt taagtttccg     11820
ttgttatgca tttgctttta tttaaaaaaa aaagaatatt tttacattaa tattagatat    11880
gagaaaagag taatttctgg attttaacct tcctacaaaa gaatatttat atttttttgta   11940 tgattttta aaaatatcgt caggaaataa taacatttca gatatacccct gaactctaca    12000 gtttatgata ttcaggaaat ttctgaattt tctgaaacct tacaaaatgc gaacggatcc    12060
gattattttc gtgattgggt gcactggaac cgggaaaagt gatcttggag tggcaattgc    12120
aaagaaatat ggaggagagg tgattagtgt agattcaatg caattttata aaggtacatg    12180
ggttttgttt caattttaaa ttaattaatt ttcgtttttc aggacttgac attgccacga    12240
ataagataac ggaagaagaa tctgaaggga ttcaacatca tatgatgtca ttttgaatc    12300 catctgaatc atcatcttat aatgtacata gtttccgaga agtcacgttg gatcttatta    12360
aagtgcttaa ttcgccactt tttgaacttg atcctaattt tcataatttt cagaaaatcc    12420
gcgcccgttc aaaaattcct gtaattgtcg gaggaaccac ttattatgct gaaagtgtcc    12480
```

-continued

```
tttatgagaa taatctgatt gaaaccaaca cttcagatga cgtggattcc aaatcgagaa    12540
catcatcaga atcgtcatct gaagacactg aagaaggaat tagtaatcaa gaattatggg    12600
atgaattgaa aaaatcgac gaaaatcag cacttcttct acatccaaat aatcgttatc      12660
gagtacagag agcattgcaa attttcagag aaactggtaa ttgatttgca aatttccaga    12720
ttaaaaacaa atcaagtaaa gttttttgca ggaatccgaa aaagtgaact tgttgaaaaa    12780
cagaaatcag atgaaactgt tgatttgggt ggacgactac gatttgataa ttctttagtt    12840
atttttatgg atgcaacacc tgaagtttta gaagaaagac ttgatggaag agttgataaa    12900
atgattaaat tgggtttgaa gaatgaattg atcgagtttt ataacgaggt aaatatttga    12960
atttttccag aaaaaaaaag aaatttttt attattttgt tttttttttca ttctttacta    13020 ttttccaaaa aagtttaaac ttttgaaaac tgttcagaaa atgttcgtgt atttatttta    13080
gcttactgag gcattatttc attgtgattt ttactatact ctataaacta aattttcagc    13140
acgccgagta cataaatcac agcaaatatg gtgtcatgca atgtattggt cttaaagaat    13200
tcgttccatg gctcaatttg gacccatcag aaagagatac actcaatggg gataaattgt    13260
tcaagcaagg gtaatttaaa tttatttca attttttataa attccaagct attttcagat    13320
gcgatgatgt gaagcttcac actcgacaat atgcacggcg ccagagacgg tggtatcgat    13380
cgagactttt aaaacggtcg gatggtgatc gggtatgttg atttaaaaa aattgaattt    13440 ttaaagaact ttttttactaa attaacaaag ttattggctg aaaatggctg aaaattatag    13500
taaaactaat caaaaaaatt gaatttttga attaaagtca taaagtgacg accagaaaat    13560 taaaaaaaa cattttttcta ttttaattaa ttcactctac ttcactttaa aaataattt     13620 cagaaaatgg caagtacaaa aatgctggat acatctgaca agtaccgaat aattagtgat    13680
ggaatggaca ttgttgatca atggatgaat ggaatcgatc tatttgaaga tgtaaaattt    13740
cacaaattct aaaatttccg aatcacaaat taaaatttct acagatctcc acagacacca    13800
atccaattct aaaagggtcc gatgcaaata ttctgctgaa ttgtgaaatc tgtaatattt    13860
caatgactgg aaaagataat tggtttgttt caatacatat tataaatttcg aaatgaattt    13920 tttcaggcag aaacatatcg atgggaaaaa gcacaagcat catgctaagc aaaagaaatt    13980
ggcagagact cgcacataag acgctatatt tatttttgt taacttaaat tatttttgtt     14040
gttgattgtt ctctaaataa aaaaacagct cagagagaag attaggcgct cgtccacatc    14100
tccgacgata gtcaacccga acgaagggaa ctatctttaa ttgtcagtga tgacgtcatg    14160
tcgtcaagaa ctcgtcatag ctgtgagaat tgaaccatta tagatttgga cattagttta    14220
ggttatatcc agtacactaa atggtacatg atagacagtg tacatttaca gatttataga    14280
ttgtctcagt gactagttac cggaagagga gaggagaaca tgtggcgatg tcttttggat    14340
cgatattatt ccgtctgaaa attgttcact aggggggactg ccgattacca cttcacatga    14400
cggaacatgt tagttaaaat attggctttt atacacattt tcaaaatagc acctgtat      14458
```

<210> SEQ ID NO 2
<211> LENGTH: 430
<212> TYPE: PRT
<213> ORGANISM: C. elegans

<400> SEQUENCE: 2

```
Met Ile Phe Arg Lys Phe Leu Asn Leu Lys Pro Tyr Lys Met Arg
1               5                   10                  15

Thr Asp Pro Ile Ile Phe Val Ile Gly Cys Thr Gly Thr Gly Lys Ser
```

```
                  20                  25                  30
Asp Leu Gly Val Ala Ile Ala Lys Lys Tyr Gly Gly Glu Val Ile Ser
             35                  40                  45
Val Asp Ser Met Gln Phe Tyr Lys Gly Leu Asp Ile Ala Thr Asn Lys
 50                  55                  60
Ile Thr Glu Glu Ser Glu Gly Ile Gln His His Met Met Ser Phe
 65                  70                  75                  80
Leu Asn Pro Ser Glu Ser Ser Tyr Asn Val His Ser Phe Arg Glu
                 85                  90                  95
Val Thr Leu Asp Leu Ile Lys Lys Ile Arg Ala Arg Ser Lys Ile Pro
            100                 105                 110
Val Ile Val Gly Gly Thr Thr Tyr Tyr Ala Glu Ser Val Leu Tyr Glu
            115                 120                 125
Asn Asn Leu Ile Glu Thr Asn Thr Ser Asp Asp Val Asp Ser Lys Ser
            130                 135                 140
Arg Thr Ser Ser Glu Ser Ser Glu Asp Thr Glu Glu Gly Ile Ser
145                 150                 155                 160
Asn Gln Glu Leu Trp Asp Glu Leu Lys Lys Ile Asp Glu Lys Ser Ala
                165                 170                 175
Leu Leu Leu His Pro Asn Asn Arg Tyr Arg Val Gln Arg Ala Leu Gln
            180                 185                 190
Ile Phe Arg Glu Thr Gly Ile Arg Lys Ser Glu Leu Val Glu Lys Gln
            195                 200                 205
Lys Ser Asp Glu Thr Val Asp Leu Gly Gly Arg Leu Arg Phe Asp Asn
210                 215                 220
Ser Leu Val Ile Phe Met Asp Ala Thr Pro Glu Val Leu Glu Glu Arg
225                 230                 235                 240
Leu Asp Gly Arg Val Asp Lys Met Ile Lys Leu Gly Leu Lys Asn Glu
                245                 250                 255
Leu Ile Glu Phe Tyr Asn Glu His Ala Glu Tyr Ile Asn His Ser Lys
                260                 265                 270
Tyr Gly Val Met Gln Cys Ile Gly Leu Lys Glu Phe Val Pro Trp Leu
            275                 280                 285
Asn Leu Asp Pro Ser Glu Arg Asp Thr Leu Asn Gly Asp Lys Leu Phe
 290                 295                 300
Lys Gln Gly Cys Asp Asp Val Lys Leu His Thr Arg Gln Tyr Ala Arg
305                 310                 315                 320
Arg Gln Arg Arg Trp Tyr Arg Ser Arg Leu Leu Lys Arg Ser Asp Gly
                325                 330                 335
Asp Arg Lys Met Ala Ser Thr Lys Met Leu Asp Thr Ser Asp Lys Tyr
            340                 345                 350
Arg Ile Ile Ser Asp Gly Met Asp Ile Val Asp Gln Trp Met Asn Gly
            355                 360                 365
Ile Asp Leu Phe Glu Asp Ile Ser Thr Asp Thr Asn Pro Ile Leu Lys
            370                 375                 380
Gly Ser Asp Ala Asn Ile Leu Leu Asn Cys Glu Ile Cys Asn Ile Ser
385                 390                 395                 400
Met Thr Gly Lys Asp Asn Trp Gln Lys His Ile Asp Gly Lys Lys His
                405                 410                 415
Lys His His Ala Lys Gln Lys Lys Leu Ala Glu Thr Arg Thr
            420                 425                 430

<210> SEQ ID NO 3
```

-continued

```
<211> LENGTH: 2041
<212> TYPE: DNA
<213> ORGANISM: C. elegans

<400> SEQUENCE: 3
ctgccataag atggcgtccg tgcggctgc acgagcagtt cctgtgggca gtgggctcag      60
gggcctgcaa cggaccctac ctcttgtagt gattctcggg gccacgggca ccggcaaatc     120
cacgctggcg ttgcagctag ccagcggct cggcggtgag atcgtcagcg ctgactccat      180
gcaggtctat gaaggcctag acatcatcac aacaaggtt tctgcccaag agcagagaat      240
ctgccggcac cacatgatca gctttgtgga tcctcttgtg accaattaca cagtggtgga     300
cttcagaaat agagcaactg ctctgattga agatatattt gcccgagaca aaattcctat     360
tgttgtggga ggaaccaatt attacattga atctctgctc tggaaagttc ttgtcaatac     420
caagccccag gagatgggca ctgagaaagt gattgaccga aaagtggagc ttgaaaagga     480
ggatggtctt gtacttcaca aacgcctaag ccaggtggac ccagaaatgg ctgccaagct     540
gcatccacat gacaaacgca agtggccag gagcttgcaa gttttttgaag aaacaggaat    600 ctctcatagt gaatttctcc atcgtcaaca tacggaagaa ggtggtggtc cccttggagg    660
tcctctgaag ttctctaacc cttgcatcct ttggcttcat gctgaccagg cagttctaga    720
tgagcgcttg gataagaggg tggatgacat gcttgctgct gggctcttgg aggaactaag    780
agattttcac agacgctata atcagaagaa tgtttcggaa aatagccagg actatcaaca    840
tggtatcttc caatcaattg gcttcaagga atttcacgag tacctgatca ctgagggaaa    900
atgcacactg gagactagta accagcttct aaagaaagga cctggtccca ttgtcccccc    960
tgtctatggc ttagaggtat ctgatgtctc gaagtgggag gagtctgttc ttgaacctgc   1020
tcttgaaatc gtgcaaagtt tcatccaggg ccacaagcct acagccactc caataaagat   1080
gccatacaat gaagctgaga caagagaag ttatcacctg tgtgacctct gtgatcgaat    1140
catcattggg gatcgcgaat gggcagcgca cataaaatcc aaatcccact tgaaccaact   1200
gaagaaaaga agaagattgg actcagatgc tgtcaacacc atagaaagtc agagtgtttc   1260
cccagactat aacaaagaac ctaaagggaa gggatcccca gggcagaatg atcaagagct   1320
gaaatgcagc gtttaagaga catgtccagt ggcctttgga aaggtggtgg ggatccagtt   1380
caggagggag gggtatgttt gtctcccagt ctgggcaaag gagtgctatg cggaattctc   1440
tgcatagcag aaaagctccc accatttct tttgatgtgg ttttaaagtc tcacgttctc    1500
tataatagaa acagcaggtc ttgtcagctc cttgtgtggc tgatgtgtct ggaaatgatg   1560
tagttcagga aagcattttt ttttctttg aaccttaaag gttctattat taaaagcagc    1620
acagattcca cattttata catgaggatc ttctttgtgg tgaataccag gattgactgc    1680 atcccttaa aagaagtttt atgtccctga ctctggctaa aattatctaa tttccagatg    1740
cttttgtaga tgactgaagt atttgtgagc acatattgg gagttctaga tttgagtgaa    1800
tggcaggaaa gggccatctc cattgagatg attaagtgaa ccaaactagt tctcggaatt    1860
ctacagagaa ggagggaatc agactgagga agctgtgaca taggacttga agaccaaaga   1920
ctttgaaatt tgcgagctgc tcatgtgtga gttattatca ctgctgtctt tctattgagt   1980
tacaaatcta tatttttatt gaagtttaaa taaagaaaaa atttacaaga aaaaaaaaa   2040 a                                                                   2041

<210> SEQ ID NO 4
<211> LENGTH: 892
```

```
<212> TYPE: PRT
<213> ORGANISM: C. elegans

<400> SEQUENCE: 4

Met Phe Arg Lys Leu Gly Ser Ser Gly Ser Leu Trp Lys Pro Lys Asn
1               5                   10                  15

Pro His Ser Leu Glu Tyr Leu Lys Tyr Leu Gln Gly Val Leu Thr Lys
            20                  25                  30

Asn Glu Lys Val Thr Glu Asn Lys Lys Ile Leu Val Glu Ala Leu
        35                  40                  45

Arg Ala Ile Ala Glu Ile Leu Ile Trp Gly Asp Gln Asn Asp Ala Ser
    50                  55                  60

Val Phe Asp Phe Phe Leu Glu Arg Gln Met Leu Leu Tyr Phe Leu Lys
65                  70                  75                  80

Ile Met Glu Gln Gly Asn Thr Pro Leu Asn Val Gln Leu Leu Gln Thr
                85                  90                  95

Leu Asn Ile Leu Phe Glu Asn Ile Arg His Glu Thr Ser Leu Tyr Phe
            100                 105                 110

Leu Leu Ser Asn Asn His Val Asn Ser Ile Ile Ser His Lys Phe Asp
        115                 120                 125

Leu Gln Asn Asp Glu Ile Met Ala Tyr Tyr Ile Ser Phe Leu Lys Thr
    130                 135                 140

Leu Ser Phe Lys Leu Asn Pro Ala Thr Ile His Phe Phe Asn Glu
145                 150                 155                 160

Thr Thr Glu Glu Phe Pro Leu Leu Val Glu Val Leu Lys Leu Tyr Asn
                165                 170                 175

Trp Asn Glu Ser Met Val Arg Ile Ala Val Arg Asn Ile Leu Leu Asn
            180                 185                 190

Ile Val Arg Val Gln Asp Asp Ser Met Ile Ile Phe Ala Ile Lys His
        195                 200                 205

Thr Lys Glu Tyr Leu Ser Glu Leu Ile Asp Ser Leu Val Gly Leu Ser
    210                 215                 220

Leu Glu Met Asp Thr Phe Val Arg Ser Ala Glu Asn Val Leu Ala Asn
225                 230                 235                 240

Arg Glu Arg Leu Arg Gly Lys Val Asp Asp Leu Ile Asp Leu Ile His
                245                 250                 255

Tyr Ile Gly Glu Leu Leu Asp Val Glu Ala Val Ala Glu Ser Leu Ser
            260                 265                 270

Ile Leu Val Thr Thr Arg Tyr Leu Ser Pro Leu Leu Ser Ser Ile
        275                 280                 285

Ser Pro Arg Arg Asp Asn His Ser Leu Leu Leu Thr Pro Ile Ser Ala
    290                 295                 300

Leu Phe Phe Ser Glu Phe Leu Leu Ile Val Arg His His Glu Thr
305                 310                 315                 320

Ile Tyr Thr Phe Leu Ser Ser Phe Leu Phe Asp Thr Gln Asn Thr Leu
                325                 330                 335

Thr Thr His Trp Ile Arg His Asn Glu Lys Tyr Cys Leu Glu Pro Ile
            340                 345                 350

Thr Leu Ser Ser Pro Thr Gly Glu Tyr Val Asn Glu Asp His Val Phe
        355                 360                 365

Phe Asp Phe Leu Leu Glu Ala Phe Asp Ser Ser Gln Ala Asp Asp Ser
    370                 375                 380

Lys Ala Phe Tyr Gly Leu Met Leu Ile Tyr Ser Met Phe Gln Asn Asn
385                 390                 395                 400
```

-continued

```
Ala Asp Val Gly Glu Leu Leu Ser Ala Ala Asn Phe Pro Val Leu Lys
                405                 410                 415
Glu Ser Thr Thr Thr Ser Leu Ala Gln Gln Asn Leu Ala Arg Leu Arg
            420                 425                 430
Ile Ala Ser Thr Ser Ser Ile Ser Lys Arg Thr Arg Ala Ile Thr Glu
        435                 440                 445
Ile Gly Val Glu Ala Thr Glu Glu Asp Glu Ile Phe His Asp Val Pro
    450                 455                 460
Glu Glu Gln Thr Leu Glu Asp Leu Val Asp Val Leu Val Asp Thr
465                 470                 475                 480
Glu Asn Ser Ala Ile Ser Asp Pro Glu Pro Lys Asn Val Glu Ser Glu
                485                 490                 495
Ser Arg Ser Arg Phe Gln Ser Ala Val Asp Glu Leu Pro Pro Pro Ser
            500                 505                 510
Thr Ser Gly Cys Asp Gly Arg Leu Phe Asp Ala Leu Ser Ser Ile Ile
        515                 520                 525
Lys Ala Val Gly Thr Asp Asp Asn Arg Ile Arg Pro Ile Thr Leu Glu
    530                 535                 540
Leu Ala Cys Leu Val Ile Arg Gln Ile Leu Met Thr Val Asp Asp Glu
545                 550                 555                 560
Lys Val His Thr Ser Leu Thr Lys Leu Cys Phe Glu Val Arg Leu Lys
                565                 570                 575
Leu Leu Ser Ser Ile Gly Gln Tyr Val Asn Gly Glu Asn Leu Phe Leu
            580                 585                 590
Glu Trp Phe Glu Asp Glu Tyr Ala Glu Phe Glu Val Asn His Val Asn
        595                 600                 605
Phe Asp Ile Ile Gly His Glu Met Leu Leu Pro Pro Ala Ala Thr Pro
    610                 615                 620
Leu Ser Asn Leu Leu His Lys Arg Leu Pro Ser Gly Phe Glu Glu
625                 630                 635                 640
Arg Ile Arg Thr Gln Ile Val Phe Tyr Leu His Ile Arg Lys Leu Glu
                645                 650                 655
Arg Asp Leu Thr Gly Glu Gly Asp Thr Glu Leu Pro Val Arg Val Leu
            660                 665                 670
Asn Ser Asp Gln Glu Pro Val Ala Ile Gly Asp Cys Ile Asn Leu His
        675                 680                 685
Asn Ser Asp Leu Leu Ser Cys Thr Val Pro Gln Gln Leu Cys Ser
    690                 695                 700
Leu Gly Lys Pro Gly Asp Arg Leu Ala Arg Phe Leu Val Thr Asp Arg
705                 710                 715                 720
Leu Gln Leu Ile Leu Val Glu Pro Asp Ser Arg Lys Ala Gly Trp Ala
                725                 730                 735
Ile Val Arg Phe Val Gly Leu Leu Gln Asp Thr Thr Ile Asn Gly Asp
            740                 745                 750
Ser Thr Asp Ser Lys Val Leu His Val Val Glu Gly Gln Pro Ser
        755                 760                 765
Arg Ile Lys Lys Arg His Pro Val Leu Thr Ala Lys Phe Ile Phe Asp
    770                 775                 780
Asp His Ile Arg Cys Met Ala Ala Lys Gln Arg Leu Thr Lys Gly Arg
785                 790                 795                 800
Gln Thr Ala Arg Gly Leu Lys Leu Gln Ala Ile Cys Ser Ala Leu Gly
                805                 810                 815
```

```
Val Pro Arg Ile Asp Pro Ala Thr Met Thr Ser Ser Pro Arg Met Asn
            820                 825                 830

Pro Phe Arg Ile Val Lys Gly Cys Ala Pro Gly Ser Val Arg Lys Thr
            835                 840                 845

Val Ser Thr Ser Ser Ser Ser Gln Gly Arg Pro Gly His Tyr Ser
            850                 855                 860

Ala Asn Leu Arg Ser Ala Ser Arg Asn Ala Gly Met Ile Pro Asp Asp
865                 870                 875                 880

Pro Thr Gln Pro Ser Ser Ser Glu Arg Arg Ser
                885                 890

<210> SEQ ID NO 5
<211> LENGTH: 355
<212> TYPE: PRT
<213> ORGANISM: C. elegans

<400> SEQUENCE: 5

Met Ala Glu Lys Ala Glu Asn Leu Pro Ser Ser Ser Ala Glu Ala Ser
1               5                   10                  15

Glu Glu Pro Ser Pro Gln Thr Gly Pro Asn Val Asn Gln Lys Pro Ser
            20                  25                  30

Ile Leu Val Leu Gly Met Ala Gly Ser Gly Lys Thr Thr Phe Val Gln
            35                  40                  45

Arg Leu Thr Ala Phe Leu His Ala Arg Lys Thr Pro Pro Tyr Val Ile
            50                  55                  60

Asn Leu Asp Pro Ala Val Ser Lys Val Pro Tyr Pro Val Asn Val Asp
65                  70                  75                  80

Ile Arg Asp Thr Val Lys Tyr Lys Glu Val Met Lys Glu Phe Gly Met
            85                  90                  95

Gly Pro Asn Gly Ala Ile Met Thr Cys Leu Asn Leu Met Cys Thr Arg
            100                 105                 110

Phe Asp Lys Val Ile Glu Leu Ile Asn Lys Arg Ser Ser Asp Phe Ser
            115                 120                 125

Val Cys Leu Leu Asp Thr Pro Gly Gln Ile Glu Ala Phe Thr Trp Ser
            130                 135                 140

Ala Ser Gly Ser Ile Ile Thr Asp Ser Leu Ala Ser Ser His Pro Thr
145                 150                 155                 160

Val Val Met Tyr Ile Val Asp Ser Ala Arg Ala Thr Asn Pro Thr Thr
            165                 170                 175

Phe Met Ser Asn Met Leu Tyr Ala Cys Ser Ile Leu Tyr Arg Thr Lys
            180                 185                 190

Leu Pro Phe Ile Val Val Phe Asn Lys Ala Asp Ile Val Lys Pro Thr
            195                 200                 205

Phe Ala Leu Lys Trp Met Gln Asp Phe Glu Arg Phe Asp Glu Ala Leu
            210                 215                 220

Glu Asp Ala Arg Ser Ser Tyr Met Asn Asp Leu Ser Arg Ser Leu Ser
225                 230                 235                 240

Leu Val Leu Asp Glu Phe Tyr Cys Gly Leu Lys Thr Val Cys Val Ser
            245                 250                 255

Ser Ala Thr Gly Glu Gly Phe Glu Asp Val Met Thr Ala Ile Asp Glu
            260                 265                 270

Ser Val Glu Ala Tyr Lys Lys Glu Tyr Val Pro Met Tyr Glu Lys Val
            275                 280                 285

Leu Ala Glu Lys Lys Leu Leu Asp Glu Glu Arg Lys Lys Arg Asp
            290                 295                 300
```

```
Glu Glu Thr Leu Lys Gly Lys Ala Val His Asp Leu Asn Lys Val Ala
305                 310                 315                 320

Asn Pro Asp Glu Phe Leu Glu Ser Glu Leu Asn Ser Lys Ile Asp Arg
            325                 330                 335

Ile His Leu Gly Gly Val Asp Glu Glu Asn Glu Glu Asp Ala Glu Leu
            340                 345                 350

Glu Arg Ser
        355

<210> SEQ ID NO 6
<211> LENGTH: 434
<212> TYPE: PRT
<213> ORGANISM: C. elegans

<400> SEQUENCE: 6

Met Ser Glu Lys Thr Phe His Lys Ala Gln Thr Ile Arg Ala Lys Ala
1               5                   10                  15

Ser Gly Val Pro Ser Ile Val Glu Ala Val Gln Phe His Gly Val Arg
            20                  25                  30

Ile Thr Lys Asn Asp Ala Leu Val Lys Glu Val Ser Glu Leu Tyr Arg
            35                  40                  45

Ser Lys Asn Leu Asp Glu Leu Val His Asn Ser His Leu Ala Ala Arg
        50                  55                  60

His Leu Gln Glu Val Gly Leu Met Asp Asn Ala Val Ala Leu Ile Asp
65                  70                  75                  80

Thr Ser Pro Ser Ser Asn Glu Gly Tyr Val Val Asn Phe Leu Val Arg
                85                  90                  95

Glu Pro Lys Ser Phe Thr Ala Gly Val Lys Ala Gly Val Ser Thr Asn
            100                 105                 110

Gly Asp Ala Asp Val Ser Leu Asn Ala Gly Lys Gln Ser Val Gly Gly
        115                 120                 125

Arg Gly Glu Ala Ile Asn Thr Gln Tyr Thr Tyr Thr Val Lys Gly Asp
    130                 135                 140

His Cys Phe Asn Ile Ser Ala Ile Lys Pro Phe Leu Gly Trp Gln Lys
145                 150                 155                 160

Tyr Ser Asn Val Ser Ala Thr Leu Tyr Arg Ser Leu Ala His Met Pro
                165                 170                 175

Trp Asn Gln Ser Asp Val Asp Glu Asn Ala Ala Val Leu Ala Tyr Asn
            180                 185                 190

Gly Gln Leu Trp Asn Gln Lys Leu Leu His Gln Val Lys Leu Asn Ala
        195                 200                 205

Ile Trp Arg Thr Leu Arg Ala Thr Arg Asp Ala Ala Phe Ser Val Arg
    210                 215                 220

Glu Gln Ala Gly His Thr Leu Lys Phe Ser Leu Glu Asn Ala Val Ala
225                 230                 235                 240

Val Asp Thr Arg Asp Arg Pro Ile Leu Ala Ser Arg Gly Ile Leu Ala
                245                 250                 255

Arg Phe Ala Gln Glu Tyr Ala Gly Val Phe Gly Asp Ala Ser Phe Val
            260                 265                 270

Lys Asn Thr Leu Asp Leu Gln Ala Ala Pro Leu Pro Leu Gly Phe
        275                 280                 285

Ile Leu Ala Ala Ser Phe Gln Ala Lys His Leu Lys Gly Leu Gly Asp
    290                 295                 300

Arg Glu Val His Ile Leu Asp Arg Cys Tyr Leu Gly Gly Gln Gln Asp
```

-continued

```
              305                 310                 315                 320
Val Arg Gly Phe Gly Leu Asn Thr Ile Gly Val Lys Ala Asp Asn Ser
                    325                 330                 335

Cys Leu Gly Gly Gly Ala Ser Leu Ala Gly Val Val His Leu Tyr Arg
                340                 345                 350

Pro Leu Ile Pro Pro Asn Met Leu Phe Ala His Ala Phe Leu Ala Ser
                355                 360                 365

Gly Ser Val Ala Ser Val His Ser Lys Asn Leu Val Gln Gln Leu Gln
            370                 375                 380

Asp Thr Gln Arg Val Ser Ala Gly Phe Gly Leu Ala Phe Val Phe Lys
385                 390                 395                 400

Ser Ile Phe Arg Leu Glu Leu Asn Tyr Thr Tyr Pro Leu Lys Tyr Val
                    405                 410                 415

Leu Gly Asp Ser Leu Leu Gly Gly Phe His Ile Gly Ala Gly Val Asn
                420                 425                 430

Phe Leu

<210> SEQ ID NO 7
<211> LENGTH: 198
<212> TYPE: PRT
<213> ORGANISM: C. elegans

<400> SEQUENCE: 7

Met Leu Tyr Ile Leu Trp Lys Leu Asn Tyr Leu Gln Lys Lys Met Ser
1               5                   10                  15

Leu Arg Lys Ile Asn Phe Val Thr Gly Asn Val Lys Lys Leu Glu Glu
            20                  25                  30

Val Lys Ala Ile Leu Lys Asn Phe Glu Val Ser Asn Val Asp Val Asp
        35                  40                  45

Leu Asp Glu Phe Gln Gly Glu Pro Glu Phe Ile Ala Glu Arg Lys Cys
    50                  55                  60

Arg Glu Ala Val Glu Ala Val Lys Gly Pro Val Leu Val Glu Asp Thr
65                  70                  75                  80

Ser Leu Cys Phe Asn Ala Met Gly Gly Leu Pro Gly Pro Tyr Ile Lys
                85                  90                  95

Trp Phe Leu Lys Asn Leu Lys Pro Glu Gly Leu His Asn Met Leu Ala
                100                 105                 110

Gly Phe Ser Asp Lys Thr Ala Tyr Ala Gln Cys Ile Phe Ala Tyr Thr
            115                 120                 125

Glu Gly Leu Gly Lys Pro Ile His Val Phe Ala Gly Lys Cys Pro Gly
        130                 135                 140

Gln Ile Val Ala Pro Arg Gly Asp Thr Ala Phe Gly Trp Asp Pro Cys
145                 150                 155                 160

Phe Gln Pro Asp Gly Phe Lys Glu Thr Phe Gly Glu Met Asp Lys Asp
                165                 170                 175

Val Lys Asn Glu Ile Ser His Arg Ala Lys Ala Leu Glu Leu Leu Lys
            180                 185                 190

Glu Tyr Phe Gln Asn Asn
        195

<210> SEQ ID NO 8
<211> LENGTH: 20
<212> TYPE: DNA
<213> ORGANISM: C. elegans

<400> SEQUENCE: 8
```

-continued cgaacacttt atatttctcg                    20

<210> SEQ ID NO 9
<211> LENGTH: 20
<212> TYPE: DNA
<213> ORGANISM: C. elegans

<400> SEQUENCE: 9
gatagttccc ttcgttcggg                    20

<210> SEQ ID NO 10
<211> LENGTH: 20
<212> TYPE: DNA
<213> ORGANISM: C. elegans

<400> SEQUENCE: 10
tttctggatt ttaaccttcc                    20

<210> SEQ ID NO 11
<211> LENGTH: 20
<212> TYPE: DNA
<213> ORGANISM: C. elegans

<400> SEQUENCE: 11
tttccgagaa gtcacgttgg                    20

<210> SEQ ID NO 12
<211> LENGTH: 20
<212> TYPE: DNA
<213> ORGANISM: C. elegans

<400> SEQUENCE: 12
tacaggaatt tttgaacggg                    20

<210> SEQ ID NO 13
<211> LENGTH: 20
<212> TYPE: DNA
<213> ORGANISM: C. elegans

<400> SEQUENCE: 13
cttcagatga cgtggattcc                    20

<210> SEQ ID NO 14
<211> LENGTH: 20
<212> TYPE: DNA
<213> ORGANISM: C. elegans

<400> SEQUENCE: 14
ggaatccgaa aaagtgaact                    20

<210> SEQ ID NO 15
<211> LENGTH: 20
<212> TYPE: DNA
<213> ORGANISM: C. elegans

<400> SEQUENCE: 15
aagagataca ctcaatgggg                    20

<210> SEQ ID NO 16
<211> LENGTH: 20
<212> TYPE: DNA
<213> ORGANISM: C. elegans

```
<400> SEQUENCE: 16
atcgatacca ccgtctctgg                                              20

<210> SEQ ID NO 17
<211> LENGTH: 20
<212> TYPE: DNA
<213> ORGANISM: C. elegans

<400> SEQUENCE: 17
ttgaatctac actaatcacc                                              20

<210> SEQ ID NO 18
<211> LENGTH: 20
<212> TYPE: DNA
<213> ORGANISM: C. elegans

<400> SEQUENCE: 18
ccaattatct tttccagtca                                              20

<210> SEQ ID NO 19
<211> LENGTH: 20
<212> TYPE: DNA
<213> ORGANISM: C. elegans

<400> SEQUENCE: 19
acattataaa gttactgtcc                                              20

<210> SEQ ID NO 20
<211> LENGTH: 20
<212> TYPE: DNA
<213> ORGANISM: C. elegans

<400> SEQUENCE: 20
ttttagttaa agcattgacc                                              20

<210> SEQ ID NO 21
<211> LENGTH: 20
<212> TYPE: DNA
<213> ORGANISM: C. elegans

<400> SEQUENCE: 21
acatctttat ccatttctcc                                              20

<210> SEQ ID NO 22
<211> LENGTH: 20
<212> TYPE: DNA
<213> ORGANISM: C. elegans

<400> SEQUENCE: 22
tgcaaaggct ctggaactcc                                              20

<210> SEQ ID NO 23
<211> LENGTH: 20
<212> TYPE: DNA
<213> ORGANISM: C. elegans

<400> SEQUENCE: 23
aaaaaccact tgatataagg                                              20

<210> SEQ ID NO 24
<211> LENGTH: 20
<212> TYPE: DNA
<213> ORGANISM: C. elegans
```

```
<400> SEQUENCE: 24
catccaaaag cagtatcacc                                              20

<210> SEQ ID NO 25
<211> LENGTH: 21
<212> TYPE: DNA
<213> ORGANISM: C. elegans

<400> SEQUENCE: 25
ttaattggat gcaagcaccc c                                            21

<210> SEQ ID NO 26
<211> LENGTH: 20
<212> TYPE: DNA
<213> ORGANISM: C. elegans

<400> SEQUENCE: 26
attactatac gaacatttcc                                              20

<210> SEQ ID NO 27
<211> LENGTH: 20
<212> TYPE: DNA
<213> ORGANISM: C. elegans

<400> SEQUENCE: 27
ttgtaaaggc gttagtttgg                                              20

<210> SEQ ID NO 28
<211> LENGTH: 20
<212> TYPE: DNA
<213> ORGANISM: C. elegans

<400> SEQUENCE: 28
caggagtatt tggtgatgcg                                              20

<210> SEQ ID NO 29
<211> LENGTH: 20
<212> TYPE: DNA
<213> ORGANISM: C. elegans

<400> SEQUENCE: 29
cgacggggag aaggtgacgg                                              20

<210> SEQ ID NO 30
<211> LENGTH: 20
<212> TYPE: DNA
<213> ORGANISM: C. elegans

<400> SEQUENCE: 30
aaaacttcta ccaacaatgg                                              20

<210> SEQ ID NO 31
<211> LENGTH: 20
<212> TYPE: DNA
<213> ORGANISM: C. elegans

<400> SEQUENCE: 31
cgtaatctct ctcgattagc                                              20

<210> SEQ ID NO 32
<211> LENGTH: 20
<212> TYPE: DNA
```

```
<213> ORGANISM: C. elegans

<400> SEQUENCE: 32
ccgtgggatg gctacttgcc                                          20

<210> SEQ ID NO 33
<211> LENGTH: 20
<212> TYPE: DNA
<213> ORGANISM: C. elegans

<400> SEQUENCE: 33
tggatttgtg gcacgagcgg                                          20

<210> SEQ ID NO 34
<211> LENGTH: 20
<212> TYPE: DNA
<213> ORGANISM: C. elegans

<400> SEQUENCE: 34
ttgattgcct ctcctcgtcc                                          20

<210> SEQ ID NO 35
<211> LENGTH: 20
<212> TYPE: DNA
<213> ORGANISM: C. elegans

<400> SEQUENCE: 35
atcaacatct gattgattcc                                          20

<210> SEQ ID NO 36
<211> LENGTH: 32
<212> TYPE: DNA
<213> ORGANISM: C. elegans

<400> SEQUENCE: 36
cagcgagcgc atgcaactat atattgagca gg                            32

<210> SEQ ID NO 37
<211> LENGTH: 41
<212> TYPE: DNA
<213> ORGANISM: C. elegans

<400> SEQUENCE: 37
aataaatatt taaatattca gatataccct gaactctaca g                  41

<210> SEQ ID NO 38
<211> LENGTH: 45
<212> TYPE: DNA
<213> ORGANISM: C. elegans

<400> SEQUENCE: 38
aaactgtaga gttcagggta tatctgaata tttaaatatt tattc              45

<210> SEQ ID NO 39
<211> LENGTH: 34
<212> TYPE: DNA
<213> ORGANISM: C. elegans

<400> SEQUENCE: 39
gtacgtggag ctctgcaact atatattgag cagg                          34

<210> SEQ ID NO 40
<211> LENGTH: 32
```

```
<212> TYPE: DNA
<213> ORGANISM: C. elegans

<400> SEQUENCE: 40
atgacactgc aggatagttc ccttcgttcg gg                              32

<210> SEQ ID NO 41
<211> LENGTH: 20
<212> TYPE: DNA
<213> ORGANISM: C. elegans

<400> SEQUENCE: 41
gtgttgcatc agttcattcc                                            20

<210> SEQ ID NO 42
<211> LENGTH: 20
<212> TYPE: DNA
<213> ORGANISM: C. elegans

<400> SEQUENCE: 42
gctgtgctag aagtcagagg                                            20

<210> SEQ ID NO 43
<211> LENGTH: 20
<212> TYPE: DNA
<213> ORGANISM: C. elegans

<400> SEQUENCE: 43
gttctccttg gaattcatcc                                            20

<210> SEQ ID NO 44
<211> LENGTH: 32
<212> TYPE: DNA
<213> ORGANISM: C. elegans

<400> SEQUENCE: 44
agtatatcta gatgtgcgag tctctgccaa tt                              32

<210> SEQ ID NO 45
<211> LENGTH: 20
<212> TYPE: DNA
<213> ORGANISM: C. elegans

<400> SEQUENCE: 45
agtaattgta catttagtgg                                            20

<210> SEQ ID NO 46
<211> LENGTH: 20
<212> TYPE: DNA
<213> ORGANISM: C. elegans

<400> SEQUENCE: 46
attaacctta cttacttacc                                            20

<210> SEQ ID NO 47
<211> LENGTH: 20
<212> TYPE: DNA
<213> ORGANISM: C. elegans

<400> SEQUENCE: 47
ctaaactaag taatataacc                                            20

<210> SEQ ID NO 48
```

-continued

```
<211> LENGTH: 20
<212> TYPE: DNA
<213> ORGANISM: C. elegans

<400> SEQUENCE: 48
gttgattctt tgagcactgg                                            20

<210> SEQ ID NO 49
<211> LENGTH: 20
<212> TYPE: DNA
<213> ORGANISM: C. elegans

<400> SEQUENCE: 49
aattcgacca attacattgg                                            20

<210> SEQ ID NO 50
<211> LENGTH: 20
<212> TYPE: DNA
<213> ORGANISM: C. elegans

<400> SEQUENCE: 50
aacatagttg ttgaggaagg                                            20

<210> SEQ ID NO 51
<211> LENGTH: 20
<212> TYPE: DNA
<213> ORGANISM: C. elegans

<400> SEQUENCE: 51
aattaatgga gattctacgg                                            20

<210> SEQ ID NO 52
<211> LENGTH: 20
<212> TYPE: DNA
<213> ORGANISM: C. elegans

<400> SEQUENCE: 52
tcagcatcta gaaatgcagg                                            20

<210> SEQ ID NO 53
<211> LENGTH: 20
<212> TYPE: DNA
<213> ORGANISM: C. elegans

<400> SEQUENCE: 53
cgaatgtcaa cattcactgg                                            20

<210> SEQ ID NO 54
<211> LENGTH: 20
<212> TYPE: DNA
<213> ORGANISM: C. elegans

<400> SEQUENCE: 54
cttaacctga tgtgtactcg                                            20

<210> SEQ ID NO 55
<211> LENGTH: 20
<212> TYPE: DNA
<213> ORGANISM: C. elegans

<400> SEQUENCE: 55
atgaagcttt agaggatgcc                                            20
```

```
<210> SEQ ID NO 56
<211> LENGTH: 20
<212> TYPE: DNA
<213> ORGANISM: C. elegans

<400> SEQUENCE: 56
cgacgaattt ctggagtcgg                                              20

<210> SEQ ID NO 57
<211> LENGTH: 20
<212> TYPE: DNA
<213> ORGANISM: C. elegans

<400> SEQUENCE: 57
actgcattat ccattaatcc                                              20

<210> SEQ ID NO 58
<211> LENGTH: 20
<212> TYPE: DNA
<213> ORGANISM: C. elegans

<400> SEQUENCE: 58
cacccaaata acatctatcc                                              20

<210> SEQ ID NO 59
<211> LENGTH: 20
<212> TYPE: DNA
<213> ORGANISM: C. elegans

<400> SEQUENCE: 59
tttaacctca tcttcgctgg                                              20

<210> SEQ ID NO 60
<211> LENGTH: 20
<212> TYPE: DNA
<213> ORGANISM: C. elegans

<400> SEQUENCE: 60
atgttccgca agcttggttc                                              20

<210> SEQ ID NO 61
<211> LENGTH: 20
<212> TYPE: DNA
<213> ORGANISM: C. elegans

<400> SEQUENCE: 61
tttaattacc caagtttgag                                              20

<210> SEQ ID NO 62
<211> LENGTH: 20
<212> TYPE: DNA
<213> ORGANISM: C. elegans

<400> SEQUENCE: 62
ttttaaccca gttactcaag                                              20

<210> SEQ ID NO 63
<211> LENGTH: 441
<212> TYPE: PRT
<213> ORGANISM: Homo sapiens

<400> SEQUENCE: 63

Met Ala Ser Val Ala Ala Ala Arg Ala Val Pro Val Gly Ser Gly Leu
 1               5                  10                  15
```

```
Arg Gly Leu Gln Arg Thr Leu Pro Leu Val Ile Leu Gly Ala Thr
            20              25                  30
Gly Thr Gly Lys Ser Thr Leu Ala Leu Gln Leu Gly Gln Arg Leu Gly
        35                  40                  45
Gly Glu Ile Val Ser Ala Asp Ser Met Gln Val Tyr Glu Gly Leu Asp
        50                  55                  60
Ile Ile Thr Asn Lys Val Ser Ala Gln Glu Gln Arg Ile Cys Arg His
65                  70                  75                  80
His Met Ile Ser Phe Val Asp Pro Leu Val Thr Asn Tyr Thr Val Val
                85                  90                  95
Asp Phe Arg Asn Arg Ala Thr Ala Leu Ile Glu Asp Ile Phe Ala Arg
            100                 105                 110
Asp Lys Ile Pro Ile Val Val Gly Gly Thr Asn Tyr Tyr Ile Glu Ser
            115                 120                 125
Leu Leu Trp Lys Val Leu Val Asn Thr Lys Pro Gln Glu Met Gly Thr
        130                 135                 140
Glu Lys Val Ile Asp Arg Lys Val Glu Leu Glu Lys Glu Asp Gly Leu
145                 150                 155                 160
Val Leu His Lys Arg Leu Ser Gln Val Asp Pro Glu Met Ala Ala Lys
                165                 170                 175
Leu His Pro His Asp Lys Arg Lys Val Ala Arg Ser Leu Gln Val Phe
            180                 185                 190
Glu Glu Thr Gly Ile Ser His Ser Glu Phe Leu His Arg Gln His Thr
        195                 200                 205
Glu Glu Gly Gly Gly Pro Leu Gly Gly Pro Leu Lys Phe Ser Asn Pro
        210                 215                 220
Cys Ile Leu Trp Leu His Ala Asp Gln Ala Val Leu Asp Glu Arg Leu
225                 230                 235                 240
Asp Lys Arg Val Asp Asp Met Leu Ala Ala Gly Leu Leu Glu Glu Leu
                245                 250                 255
Arg Asp Phe His Arg Arg Tyr Asn Gln Lys Asn Val Ser Glu Asn Ser
            260                 265                 270
Gln Asp Tyr Gln His Gly Ile Phe Gln Ser Ile Gly Phe Lys Glu Phe
        275                 280                 285
His Glu Tyr Leu Ile Thr Glu Gly Lys Cys Thr Leu Glu Thr Ser Asn
        290                 295                 300
Gln Leu Leu Lys Lys Gly Pro Gly Pro Ile Val Pro Pro Val Tyr Gly
305                 310                 315                 320
Leu Glu Val Ser Asp Val Ser Lys Trp Glu Glu Ser Val Leu Glu Pro
                325                 330                 335
Ala Leu Glu Ile Val Gln Ser Phe Ile Gln Gly His Lys Pro Thr Ala
            340                 345                 350
Thr Pro Ile Lys Met Pro Tyr Asn Glu Ala Glu Asn Lys Arg Ser Tyr
            355                 360                 365
His Leu Cys Asp Leu Cys Asp Arg Ile Ile Ile Gly Asp Arg Glu Trp
        370                 375                 380
Ala Ala His Ile Lys Ser Lys Ser His Leu Asn Gln Leu Lys Lys Arg
385                 390                 395                 400
Arg Arg Leu Asp Ser Asp Ala Val Ala Asn Thr Ile Glu Ser Gln Ser
                405                 410                 415
Val Ser Pro Asp Tyr Asn Lys Glu Pro Lys Gly Lys Gly Ser Pro Gly
            420                 425                 430
```

```
Gln Asn Asp Glu Leu Lys Cys Ser Val
        435             440
```

<210> SEQ ID NO 64
<211> LENGTH: 223
<212> TYPE: DNA
<213> ORGANISM: C. elegans

<400> SEQUENCE: 64

```
tgattttac  taactctata  aactaaattt  cagcacgccg  agtacataat  cacagcaaat    60
atggtgtcac gttggtctta aagaattcgt tccatggctc aatttggacc catcagaaag   120
agatacactc aatggggata aattgttcaa gcaagggtaa tttaaattta ttttcaattt   180
ttataattcc aagctatttt cagatgcgat gatgtgaagc ttc                     223
```

<210> SEQ ID NO 65
<211> LENGTH: 43
<212> TYPE: PRT
<213> ORGANISM: C. elegans

<400> SEQUENCE: 65

```
His Glu Ala Tyr Ile Asn His Ser Lys Tyr Gly Val Thr Leu Val Leu
1               5                   10                  15
Asn Ser Phe His Gly Ile Trp Thr His Gln Lys Trp Ile His Ser Met
            20                  25                  30
Gly Ile Asn Cys Ser Ser Lys Asp Ala Met Met
        35                  40
```

<210> SEQ ID NO 66
<211> LENGTH: 1401
<212> TYPE: DNA
<213> ORGANISM: C. elegans

<400> SEQUENCE: 66

```
aaaatatcgt caggaaataa taacatttca gatataccct gaactctaca gtttatgata    60
ttcaggaaat ttctgaattt tctgaaacct tacaaaatgc gaacggatcc gattattttc   120
gtgattgggt gcactggaac cgggaaaagt gatcttggag tggcaattgc aaagaaatat   180
ggaggagagg tgattagtgt agattcaatg caatttata aaggtacatg ggttttgttt    240
caattttaaa ttaattaatt ttcgttttc aggacttgac attgccacga ataagataac   300
ggaagaagaa tctgaaggga ttcaacatca tatgatgtca ttttgaatc catctgaatc   360
atcatcttat aatgtacata gtttccgaga agtcacgttg gatcttatta aagtgcttaa   420
ttcgccactt tttgaacttg atcctaattt tcataatttt cagaaaatcc gcgcccgttc   480
aaaaattcct gtaattgtcg gaggaaccac ttattatgct gaaagtgtcc tttatgagaa   540
taatctgatt gaaaccaaca cttcagatga cgtggattcc aaatcgagaa catcatcaga   600
atcgtcatct gaagacactg aagaaggaat tagtaatcaa gaattatggg atgaattgaa   660
aaaaatcgac gaaaaatcag cacttcttct acatccaaat aatcgttatc gagtacagag   720
agcattgcaa attttcagag aaactggtaa ttgattgca aatttccaga ttaaaaacaa    780
atcaagtaaa gttttttgca ggaatccgaa aagtgaact tgttgaaaaa cagaaatcag    840
atgaaactgt tgatttgggt ggacgactac gatttgataa ttctttagtt attttttatgg   900
atgcaacacc tgaagttta gaagaaagac ttgatggaag agttgataaa atgattaaat   960
tgggtttgaa gaatgaaatt gatcgagttt ataacgagg taaatatttg aattttccta   1020
gaaaaaaaaa gaaaatttttt tattatttg tttttttttc attctttact attttccaaa   1080
```

-continued

```
aaagtttaaa cttttgaaaa ctgttcagaa aatgttcgtg tatttatttt agcttactga   1140
ggcattattt cattgtgatt tttactatac tctataaact aaattttcag cacgccgagt   1200
acataaatca cagcaaatat ggtgtcatgc aatgtattgg tcttaaagaa ttcgttccat   1260
ggctcaattt ggacccatca gaaagagata cactcaatgg ggataaattg ttcaagcaag   1320
ggtaatttaa atttattttc aattttata aattccaagc tattttcaga tgcgatgatg   1380
tgaagcttca cactcgacaa t                                             1401
```

<210> SEQ ID NO 67
<211> LENGTH: 418
<212> TYPE: PRT
<213> ORGANISM: S.cerevisiae

<400> SEQUENCE: 67

```
Met Leu Lys Gly Pro Leu Lys Gly Cys Leu Asn Met Ser Lys Lys Val
1               5                   10                  15

Ile Val Ile Ala Gly Thr Thr Gly Val Gly Lys Ser Gln Leu Ser Ile
            20                  25                  30

Gln Leu Ala Gln Lys Phe Asn Gly Glu Val Ile Asn Ser Asp Ser Met
        35                  40                  45

Gln Val Tyr Lys Asp Ile Pro Ile Ile Thr Asn Lys His Pro Leu Gln
    50                  55                  60

Glu Arg Glu Gly Ile Pro His Val Met Asn Asn Val Asp Trp Ser Glu
65                  70                  75                  80

Glu Tyr Tyr Ser His Arg Phe Glu Thr Glu Cys Met Asn Ala Ile Glu
                85                  90                  95

Asp Ile His Arg Arg Gly Lys Ile Pro Ile Val Val Gly Gly Thr His
            100                 105                 110

Tyr Tyr Leu Gln Thr Leu Phe Asn Lys Arg Val Asp Thr Lys Ser Ser
        115                 120                 125

Glu Arg Lys Leu Thr Arg Lys Gln Leu Asp Ile Leu Glu Ser Asp Pro
    130                 135                 140

Asp Val Ile Tyr Asn Thr Leu Val Lys Cys Asp Pro Asp Ile Ala Thr
145                 150                 155                 160

Lys Tyr His Pro Asn Asp Tyr Arg Arg Val Gln Arg Met Leu Glu Ile
                165                 170                 175

Tyr Tyr Lys Thr Gly Lys Lys Pro Ser Glu Thr Phe Asn Glu Gln Lys
            180                 185                 190

Ile Thr Leu Lys Phe Asp Leu Phe Leu Trp Leu Tyr Ser Lys Pro Glu
        195                 200                 205

Pro Leu Phe Gln Arg Leu Asp Asp Arg Val Asp Met Leu Glu Arg
    210                 215                 220

Gly Ala Leu Gln Glu Ile Lys Gln Leu Tyr Glu Tyr Ser Gln Asn
225                 230                 235                 240

Lys Phe Thr Pro Glu Gln Cys Glu Asn Gly Val Trp Gln Val Ile Gly
                245                 250                 255

Phe Lys Glu Phe Leu Pro Trp Leu Thr Gly Lys Thr Asp Asp Asn Thr
            260                 265                 270

Lys Leu Glu Asp Cys Ile Glu Arg Met Lys Thr Arg Thr Arg Gln Tyr
        275                 280                 285

Ala Lys Arg Gln Val Lys Trp Ile Lys Met Leu Ile Pro Asp Ile
    290                 295                 300

Lys Gly Asp Ile Leu Leu Asp Ala Thr Asp Leu Ser Gln Trp Asp Thr
```

-continued

```
            305                 310                 315                 320
Asn Ala Ser Gln Arg Ala Ile Ala Ile Ser Asn Asp Phe Ile Ser Asn
                325                 330                 335
Arg Pro Ile Lys Gln Glu Arg Ala Lys Ala Leu Glu Glu Leu Leu Ser
            340                 345                 350
Lys Gly Glu Thr Thr Met Lys Lys Leu Asp Asp Trp Thr His Tyr Thr
            355                 360                 365
Arg Asn Val Cys Arg Asn Ala Asp Gly Lys Asn Val Val Ala Ile Gly
            370                 375                 380
Glu Lys Tyr Trp Lys Ile His Leu Gly Ser Arg Arg His Lys Ser Asn
385                 390                 395                 400
Leu Lys Arg Asn Thr Arg Gln Ala Asp Phe Glu Lys Trp Lys Ile Asn
                405                 410                 415
Lys Lys

<210> SEQ ID NO 68
<211> LENGTH: 313
<212> TYPE: PRT
<213> ORGANISM: E. coli

<400> SEQUENCE: 68

Met Ser Asp Ile Ser Lys Ala Ser Leu Pro Lys Ala Ile Phe Leu Met
1               5                   10                  15
Gly Pro Thr Ala Ser Gly Lys Thr Ala Leu Ala Ile Glu Leu Arg Lys
            20                  25                  30
Ile Leu Pro Val Glu Leu Ile Ser Val Asp Ser Ala Leu Ile Tyr Lys
        35                  40                  45
Gly Met Asp Ile Gly Thr Ala Lys Pro Asn Ala Glu Glu Leu Leu Ala
    50                  55                  60
Ala Pro Arg Leu Leu Asp Ile Arg Asp Pro Ser Gln Ala Tyr Ser Ala
65                  70                  75                  80
Ala Asp Phe Arg Arg Asp Ala Leu Ala Glu Met Ala Asp Ile Thr Ala
                85                  90                  95
Ala Gly Arg Ile Pro Leu Leu Val Gly Gly Thr Met Leu Tyr Phe Lys
            100                 105                 110
Ala Leu Leu Glu Gly Leu Ser Pro Leu Pro Ser Ala Asp Pro Glu Val
        115                 120                 125
Arg Ala Arg Ile Glu Gln Gln Ala Ala Glu Glu Gly Trp Glu Ser Leu
    130                 135                 140
His Arg Gln Leu Gln Glu Val Asp Pro Val Ala Ala Arg Ile His Pro
145                 150                 155                 160
Pro Asn Asp Pro Gln Arg Leu Ser Arg Ala Leu Glu Val Phe Phe Ile
                165                 170                 175
Ser Gly Lys Thr Leu Thr Glu Leu Thr Gln Thr Ser Gly Asp Ala Leu
            180                 185                 190
Pro Tyr Gln Val Gln Phe Ala Ile Ala Pro Ala Ser Arg Glu Leu Leu
        195                 200                 205
His Gln Arg Ile Glu Gln Arg Phe His Gln Met Leu Ala Ser Gly Phe
    210                 215                 220
Glu Ala Glu Val Arg Ala Leu Phe Ala Arg Gly Asp Leu His Thr Asp
225                 230                 235                 240
Leu Pro Ser Ile Arg Cys Val Gly Thr Arg Gln Met Trp Ser Tyr Leu
                245                 250                 255
Glu Gly Glu Ile Ser Tyr Asp Glu Met Val Tyr Arg Gly Val Ala Thr
```

-continued

```
                   260                 265                 270
Arg Gln Leu Ala Lys Arg Gln Ile Thr Trp Leu Arg Gly Trp Glu Gly
            275                 280                 285

Val His Trp Leu Asp Ser Glu Lys Pro Glu Gln Ala Arg Asp Glu Val
        290                 295                 300

Leu Gln Val Val Gly Ala Ile Ala Gly
305                 310

<210> SEQ ID NO 69
<211> LENGTH: 192
<212> TYPE: PRT
<213> ORGANISM: H. sapiens
<220> FEATURE:
<221> NAME/KEY: misc_feature
<222> LOCATION: (46)..(46)
<223> OTHER INFORMATION: Xaa can be any naturally occurring amino acid
<220> FEATURE:
<221> NAME/KEY: misc_feature
<222> LOCATION: (82)..(82)
<223> OTHER INFORMATION: Xaa can be any naturally occurring amino acid

<400> SEQUENCE: 69

Met Ala Ala Ser Leu Val Gly Lys Lys Ile Val Phe Val Thr Gly Asn
1               5                   10                  15

Ala Lys Lys Leu Glu Glu Val Val Gln Ile Leu Gly Asp Lys Phe Pro
            20                  25                  30

Cys Thr Leu Val Ala Gln Lys Ile Asp Leu Pro Glu Tyr Xaa Gly Glu
        35                  40                  45

Pro Asp Glu Ile Ser Ile Gln Lys Cys Gln Glu Ala Val Arg Gln Val
    50                  55                  60

Gln Gly Pro Val Leu Val Glu Asp Thr Cys Leu Cys Phe Asn Ala Leu
65                  70                  75                  80

Gly Xaa Leu Pro Gly Pro Tyr Ile Lys Trp Phe Leu Glu Lys Leu Lys
                85                  90                  95

Pro Glu Gly Leu His Gln Leu Leu Ala Gly Phe Glu Asp Lys Ser Ala
            100                 105                 110

Tyr Ala Leu Cys Thr Phe Ala Leu Ser Thr Gly Asp Pro Ser Gln Pro
        115                 120                 125

Val Arg Leu Phe Arg Gly Thr Ser Gly Arg Ile Val Ala Pro Arg Gly
    130                 135                 140

Cys Gln Asp Phe Gly Trp Asp Pro Cys Phe Gln Pro Asp Gly Tyr Glu
145                 150                 155                 160

Gln Thr Tyr Ala Glu Met Pro Lys Ala Glu Lys Asn Ala Val Ser His
                165                 170                 175

Arg Phe Ala Leu Leu Glu Leu Gln Glu Tyr Phe Gly Ser Leu Ala Ala
            180                 185                 190

<210> SEQ ID NO 70
<211> LENGTH: 196
<212> TYPE: PRT
<213> ORGANISM: S.cerevisiae

<400> SEQUENCE: 70

Met Ser Asn Asn Glu Ile Val Phe Val Thr Gly Asn Ala Asn Lys Leu
1               5                   10                  15

Lys Glu Val Gln Ser Ile Leu Thr Gln Glu Val Asp Asn Asn Asn Lys
            20                  25                  30

Thr Ile His Leu Ile Asn Glu Ala Leu Asp Leu Glu Glu Leu Gln Asp
        35                  40                  45
```

```
Thr Asp Leu Asn Ala Ile Ala Leu Ala Lys Gly Lys Gln Ala Val Ala
        50                  55                  60

Ala Leu Gly Lys Gly Lys Pro Val Phe Val Glu Asp Thr Ala Leu Arg
 65                  70                  75                  80

Phe Asp Glu Phe Asn Gly Leu Pro Gly Ala Tyr Ile Lys Trp Phe Leu
                 85                  90                  95

Lys Ser Met Gly Leu Glu Lys Ile Val Lys Met Leu Glu Pro Phe Glu
            100                 105                 110

Asn Lys Asn Ala Glu Ala Val Thr Thr Ile Cys Phe Ala Asp Ser Arg
            115                 120                 125

Gly Glu Tyr His Phe Gln Gly Ile Thr Arg Gly Lys Ile Val Pro
        130                 135                 140

Ser Arg Gly Pro Thr Thr Phe Gly Trp Asp Ser Ile Phe Glu Pro Phe
145                 150                 155                 160

Asp Ser His Gly Leu Thr Tyr Ala Glu Met Ser Lys Asp Ala Lys Asn
                165                 170                 175

Ala Ile Ser His Arg Gly Ala Phe Ala Gln Phe Lys Glu Tyr Leu Tyr
                180                 185                 190

Gln Asn Asp Phe
        195

<210> SEQ ID NO 71
<211> LENGTH: 198
<212> TYPE: PRT
<213> ORGANISM: E.coli

<400> SEQUENCE: 71

Met Gln Lys Val Val Leu Ala Thr Gly Asn Val Gly Lys Val Arg Glu
 1               5                  10                  15

Leu Ala Ser Leu Leu Ser Asp Phe Gly Leu Asp Ile Val Ala Gln Thr
            20                  25                  30

Asp Leu Gly Val Asp Ser Ala Glu Glu Thr Gly Leu Thr Phe Ile Glu
        35                  40                  45

Asn Ala Ile Leu Lys Ala Arg His Ala Ala Lys Val Thr Ala Leu Pro
 50                  55                  60

Ala Ile Ala Asp Asp Ser Gly Leu Ala Val Asp Val Leu Gly Gly Ala
 65                  70                  75                  80

Pro Gly Ile Tyr Ser Ala Arg Tyr Ser Gly Glu Asp Ala Thr Asp Gln
                 85                  90                  95

Lys Asn Leu Gln Lys Leu Leu Glu Thr Met Lys Asp Val Pro Asp Asp
            100                 105                 110

Gln Arg Gln Ala Arg Phe His Cys Val Leu Val Tyr Leu Arg His Ala
        115                 120                 125

Glu Asp Pro Thr Pro Leu Val Cys His Gly Ser Trp Pro Gly Val Ile
130                 135                 140

Thr Arg Glu Pro Ala Gly Thr Gly Phe Gly Tyr Asp Pro Ile Phe
145                 150                 155                 160

Phe Val Pro Ser Glu Gly Lys Thr Ala Ala Glu Leu Thr Arg Glu Glu
                165                 170                 175

Lys Ser Ala Ile Glu Ser His Arg Gly Gln Ala Leu Lys Leu Leu Leu
                180                 185                 190

Asp Ala Leu Arg Asn Gly
        195
```

<210> SEQ ID NO 72
<211> LENGTH: 221
<212> TYPE: PRT
<213> ORGANISM: Artificial sequence
<220> FEATURE:
<223> OTHER INFORMATION: Drosophila conceptual translation

<400> SEQUENCE: 72

```
Pro Ile Thr Cys Lys His Lys Lys Gln Leu Thr Ala Thr Ser Gly Ser
1               5                   10                  15

Val Pro Ile Gly Ile His Val Leu Lys Thr Cys Gly Phe Tyr Leu Pro
            20                  25                  30

Leu Thr Ile His Ser Gln Val Glu Met Ile Arg Lys Val Pro Leu Ile
        35                  40                  45

Val Val Leu Gly Ser Thr Gly Thr Gly Lys Thr Lys Leu Ser Leu Gln
50                  55                  60

Leu Ala Glu Arg Phe Gly Gly Glu Ile Ile Ser Ala Asp Ser Met Gln
65                  70                  75                  80

Val Tyr Thr His Leu Asp Ile Ala Thr Ala Lys Ala Thr Lys Glu Glu
                85                  90                  95

Gln Ser Arg Ala Arg His His Leu Leu Asp Val Ala Thr Pro Ala Glu
            100                 105                 110

Pro Phe Thr Val Thr His Phe Arg Asn Ala Ala Leu Pro Ile Val Glu
        115                 120                 125

Arg Leu Leu Ala Lys Asp Thr Ser Pro Ile Val Val Gly Gly Thr Asn
130                 135                 140

Tyr Tyr Ile Glu Ser Leu Leu Trp Asp Ile Leu Val Asp Ser Asp Val
145                 150                 155                 160

Lys Pro Asp Glu Gly Lys His Ser Gly Glu His Leu Lys Asp Ala Glu
                165                 170                 175

Leu Asn Ala Leu Ser Thr Leu Glu Leu His Gln His Leu Ala Lys Ile
            180                 185                 190

Asp Ala Gly Ser Ala Asn Arg Ile His Pro Asn Asn Arg Arg Lys Ile
        195                 200                 205

Ile Arg Ala Ile Glu Val Tyr Gln Ser Thr Gly Gln Thr
210                 215                 220
```

<210> SEQ ID NO 73
<211> LENGTH: 4849
<212> TYPE: DNA
<213> ORGANISM: C. elegans

<400> SEQUENCE: 73

```
atcgtgttcc aggtgcaact atatattgag caggaggacg agttgtttgt ttcatgctgc    60
ttaaaaataa aaatggaaaa ttgagtcaaa agttgagat aaaacaaatt aaaacaattt    120
tctgaaaaat aaacaactga aatttgaagt aataaacaac acgcgaaaac gttatttcgg    180
agcatcgttt gagaagtaaa acttttttc ggcgcaccct tgtgcgcagt ttttatcttc    240
tcttttaatt taattttcaa gctaaatctt tcttttaaa ctttgaataa atatttaaat    300
attcagaatg caccaataaa cctggaacaa aatcgataat gttccgcaag cttggttctt    360
ctgggtcact atggaagccg aaaaatccgc attctttgga atacctcaaa tatttacaag    420
gagtgctcac aaaaaatgag aaagttacgg aaaaacaataa gaaatatta gtagaagcat    480 tacgagctat cgcagaaatt ctcatttggg gcgatcagaa tgatgcttcg gttttttgagt    540 gagttttttt ccaatgtttt tttcaaatc tgatgttgaa tttcagtttc ttccttgagc    600
```

-continued

```
ggcaaatgct tctttatttc ttgaaaatta tggaacaagg aaacacacca ctaaatgtac    660
aattactgca gactttgaac attttattcg aaaatattcg acatgaaact tcactttgta    720
agttttttat atggattttc gcttaaaatt gccagttttc agatttcctt ctaagtaaca    780
atcatgtaaa ctcgattatt tcccacaaat tcgatttaca aaatgatgag atcatggctt    840
actacattag ttttctgaaa actctttcat ttaaactgaa tccagctaca atccacttct    900
tcttcaatga aacgactgaa gaatttccat tgttggtaga agttttgaag ctttataatt    960
ggaatgaatc aatggttcga attgctgtta gaaatattct tttaaatatt gtgagagttc   1020
aagatgattc aatgattatt ttcgctatca agcatacaaa agttagtaga aaattatttt   1080
gaaaaggtgt atttaagcaa taaatattac aggaatatct atcggagtta atagattctc   1140
tagttggtct ctcacttgaa atggacacat ttgtacgatc tgctgagaat gtgttagcta   1200
atcgagagag attacgagga aaagtggatg atttaattga tttgattcat tatattggtg   1260
aactattgga tgtggaagct gtcgccgaaa gtttatcaat tttaggtcag ttttactgct   1320
ggaaaatcaa gttttaatg ttaaattttc agtaacaaca cgatacttaa gccctctatt   1380
actttcaagt atatcaccaa gaagagataa tcattcactt ctactcactc cgatttctgc   1440 gttattttt ttctctgaat ttttattggt gagttttaac atttaaaatt cattttttct   1500
aatttattta tttttcagat agttcgtcac catgaaacaa tatatacatt tttatcatct   1560
ttcctatttg acactcagaa tactttgacg acccattgga tacgtcataa tgagaaatat   1620
tgcttagaac cgattacatt atcatccaca accggagaat atgtgaatga agaccagtaa   1680
gagctgaaat tttaaaattt ttgctttgaa tatagtattt tcagcgtatt tttcgatttt   1740
ctactggaag catttgattc cagtcaagca gacgattcga aggcattcta tggattaatg   1800
ctgatttatt caatgtttca gaataatggt gagttttaaa aaattgattt gttaaattaa   1860
aatttccatt tccaataact cctcttcaga cagtaagttt tcaatgttgt aaagttcctg   1920
ttcatctgtg atcgttttct tcattttttt agttttgcat gaacagtttt caaattttt   1980 tgatatcata cagtaaatat cgtcatccag ataattttct attaaaaaa aatgaataaa    2040 aagagggcgc gcagaaattg ccgaagtaat gtaaatttaa agggacacat gcgtagcttg   2100
ttgtgtgggt ctcgccgcgc tttgtttgat ttatcttgtt ttctgctcaa agagctgttt   2160 ttatttagc gttgaatgct tttttaccgt tctcatcggc ttttaatag gaatatttaa    2220 aaaaaaggt ttaataaatc ttcgttttta caaaatccat ctaagatttg catttgtgaa    2280
gctcaacaag taaagtttaa gtaacattgt tttttaaaaa acaattgaac caaattttgc   2340
cgaaacatta ataacatgac gatactctat aaaatattcc tcttttcaaa ataaattttc   2400
aaaaaaaatc cattttttcag ccgatgttgg agaacttcta tctgctgcca acttcccagt  2460
gctcaaagaa tcaacgacaa cttcattagc tcaacagaat cttgctcgtc tccgaatagc   2520
atctacgtct tccatatcaa agcgaacgag agctatcact gaaattggag tagaagcgac   2580
cgaggaagat gagattttc atgatgttcc tgaagaacaa acgttggtaa gtaaataaat   2640
caacattgat tgttacacaa actttaatat ttttaaattt gaaaattttc ttcaaagtgc   2700
tcaaaaatcc tgtcgaaaat tacaggaaga tctggtggat gatgtattgg ttgatactga   2760
aaattcagca ataagtgatc cagaagtgag tagaaaacgt gcatgtatta attattaaaa   2820
aaaaaatata gttttcccca gttttccttg acctaaaact cagcaatttc agcctaaaaa   2880
cgtggagtca gaatctcgtt ctcgatttca atctgctgtt gatgagcttc cacctccgtc   2940
gacttctgga tgtgatggtc gacttttga tgcactttca tcgattatca aagcagttgg   3000
```

-continued

```
aacagatgac aatcgaattc gaccaattac attggaactt gcatgtcttg taattcggca    3060
aattttaatg actgttgatg atgaaaaagt aagattacaa attcaaaatt gagcaaaatc    3120
agaatctaaa tttcataaat tgttcaggta cataccagtt taacgaaatt atgcttcgaa    3180
gttcgtctaa aacttttatc atcaattgga caatatgtta atggagagaa tctgtttttg    3240
gagtggtttg aggatgaata tgcagaattt gaagtaagcc aagaggtccg aaaataattt    3300
aattcatcct ttttattcag gtgaatcacg tgaatttcga tataatcggt cacgaaatgc    3360
ttcttcctcc agctgcaact cctctttcga atctgctact tcataagcga ttgcccagtg    3420
gatttgaaga acgaataaga actgtaggaa acttttttaaa tttgaaaatt aattatatat    3480
atatttgcag caaatcgtat tctacctaca tattcgaaaa ttggaacgag atttgaccgg    3540
tgaaggagac acagaattac ctgtgagagt gttgaattct gatcaggaac cagttgccat    3600
cggtgattgt attaatttac gtgagttcat ctgcatagaa acaccatat ttctactcaa     3660 attaacaatt ttcagataat tcggatcttc tatcctgcac tgtggttcct caacaactat    3720
gttctcttgg aaaacctggt gatcgtcttg ctcgattcct tgtcactgat agacttcaat    3780
taattcttgt cgaaccggat tctcgaaaag ccggatgggc aattgttcga ttcgtaggac    3840
ttcttcaaga tacaacaatt aatggagatt ctacggattc gaaagttttg catgttgtgg    3900
tggaagggca accctcgaga attaaggtaa gaatactaac gggaaaaaaa aatcaaaaaa    3960
ttacttctgt ttcagaaaag acatccggtt ttaactgcaa agttcatatt cgatgatcac    4020
attcggtgta tggcagcaaa gcaacggctc accaaggtaa cggaaaaaat aaccaaaaag    4080
acggaaagtt attgtaaatg gacgaaatcg gcgaaattaa ttgaaaacgt ttgaatttgc    4140
cgctaaaacc aaacgaaaac caaacgaaag cgaaatttaa ctatcccttc aggtagaata    4200 tacatttat ttctctttat agggtcgcca aacagcacgt ggtctgaaac ttcaggcgat     4260
atgttcagct cttggagttc cacgtatcga tccagcgaca atgacgtcat caccacgaat    4320
gaatccattc agaattgtga aaggatgcgc accgggaagt gtacgaaaaa ctgtttccac    4380
atcatcatcg tcaagccaag gacgtcccgg acattattct gcaaatctta gatcagcatc    4440
tagaaatgca ggaatgatac cagatgatcc aactcaaccg agtagttctt cggaaagaag    4500
atcctaggga tcaatatctc ttcagtttca tcattttatg ctgtaaattg tatttaagta    4560
ttcctattct ttgtagtact gtatttacac atcgtctagt taaaatcaca aatctccgaa    4620
aaaacaaacc agtgaacatg tgatatttct cttgcccata gttctctttt tttttttgaaa   4680 caaaaacaat tactttatg ctcacctatt cgagccatat ttttttccca attaccggtt     4740
gtttatttta atttctttttt tttttctgta aatctacttt atttttaaaa ctgcatttga   4800
gattgtgtat attttttcaa aatggttcaa atgccgaatc tatctactt                4849
```

<210> SEQ ID NO 74
<211> LENGTH: 1650
<212> TYPE: DNA
<213> ORGANISM: C. elegans

<400> SEQUENCE: 74

```
tttaatcatt attcaaacag aaaaaccgat tatttattca gattctcaaa aatggctgaa      60
aaagctgaaa atcttccatc ttcttcggcc gaagcttcag aagagccatc acctcaaact     120
ggaccaaatg tgaatcaaaa accatcgatt ttggttcttg gaatggctgg ttctggaaaa     180
acgacatttg ttcaggtaac tttcattcaa ttttgagagt tttcaaacat tactattttc     240
```

-continued

| | |
|---|---|
| agcgtctcac agcattccta catgctcgta aaacacctcc atatgtgatt aatctggatc | 300 |
| cggcagttag caaagtacct tatccagtga atgttgacat tcgagatact gtgaaataca | 360 |
| aggaagttat gaaagaattc ggaatgggac caaatggagc aattatgaca tgtcttaacc | 420 |
| tgatgtgtac tcgttttgat aaagtaattg agttgattaa taagagatct tctgatttct | 480 |
| cagtttgtct tcttgatact cctggacaaa ttgaagcatt cacttggagt gctagtggat | 540 |
| ctattatcac tgattcattg gcaagtagcc atcccacggt aagggatttt gatttatgaa | 600 |
| atctgcttga aatgaaaaaa gattctaata aattttgac ttttaaacat tttttacagt | 660 |
| tatatttggt ctattttcta tcattaaaag caaaatgaaa agtcgattct actccatatt | 720 |
| tattaatttc gacttttcag gtggtaatgt acattgtgga ttccgctcgt gccacaaatc | 780 |
| caactacatt catgtccaat atgctctacg catgttccat tctctaccgt accaaacttc | 840 |
| cattcattgt cgttttcaac aaagctgata ttgtcaaacc aacatttgca ctcaaatgga | 900 |
| tgcaagattt cgaagatttt gatgaagctt tagaggatgc cagaagcagt tatatgaatg | 960 |
| atttgagtcg ttcattgagt ctcgttcttg atgaattcta ttgcggactg aaaacaggtt | 1020 |
| tttattcgaa ataaaacctt ttttaaataa taaatttcag tttgcgtcag ttctgcaact | 1080 |
| ggagaaggat tcgaagatgt aatgacagca atcgatgaaa gtgttgaagc atacaaaaaa | 1140 |
| gaatatgttc caatgtatga aaaagtgttg gctgagaaaa aactattgga tgaggaggag | 1200 |
| agaaagaaaa gagatgaaga ggtaattgta gtaatttaat tctgattatc ttcaaatttt | 1260 |
| cagactctga aaggaaaagc tgttcacgac ctgaacaaag tcgccaatcc cgacgaattt | 1320 |
| ctggagtcgg agttgaattc aaaaatcgat agaattcatt tgggcggagt cgatgaagag | 1380 |
| aatgaggagg atgctgaact cgaaagatcc tgattttctt tttgtttttg aattttatt | 1440 |
| ctatttgat ccctgtttac ttcttattgt tctcattttg ttgcgttgtt ttacatttta | 1500 |
| ctcattttg cataaacttg ttgcaaaaat caatataatt tttgatctgg aaatggtttt | 1560 |
| aaaccttaac ctttcatata ttaataattt tttttcaaaa aaacgttcta aaaaggttcc | 1620 |
| tcatttttc aatataggaa attttgaaga | 1650 |

<210> SEQ ID NO 75
<211> LENGTH: 3251
<212> TYPE: DNA
<213> ORGANISM: C. elegans

<400> SEQUENCE: 75

| | |
|---|---|
| tcttttccaa aaatgaggtt cttcgcttga aaagccaaca tttaaaacct tttttttttcc | 60 |
| agaaacctag tggttaatgt ctgaaaagac gttccacaag gcacagacca tccgtgcaaa | 120 |
| ggcatccgga gtgccttcaa tcgtcgaagc tgtacagttt catggagttc gcatcacaaa | 180 |
| aaacgatgct ttggttaagg aggtactacc caaatttcaa aatgttgcac aattcaattg | 240 |
| aaaatataaa ttgtgaatta aattcaactt acatgttttt tcaggtttcc gaattataca | 300 |
| gaagtaaaaa tctagatgaa cttgttcata actctcatct ggcggctcgt catcttcaag | 360 |
| aagttggatt aatggataat gcagttgctc taattgatac atctccaagc tcaaatgaag | 420 |
| gatatgttgt caatttccta gttcgagaac caaaatcatt cactgctgga gtcaaagcag | 480 |
| gagtttcaac gaatggagat gcggatgtca gtttaaatgc cggaaaacaa agtgttggag | 540 |
| gacgaggaga ggcaatcaat acacagtata catatactgt aaaggtaagg acgagagttg | 600 |
| gcactgccag tttggcatgt tctcccaata ttttttaatt ataaaatttg gaagtataaa | 660 |
| aaaatgtttg cttcatctaa aaatagcctt tttcacatga aaaaaattga aaaaaagtgc | 720 |

-continued

```
tcaaaaattt cagaaatttc caatttccaa acaattttgg agaactttca aaaattttc    780
caactgaaat taaagctata ttctatcact aaattttata caagtcttaa gagaaaatga    840
tgaagtggct cattttgtag aatttcctaa aaaataatat cttcagggcg atcactgctt    900
caacatttcc gcaatcaaac cattcctggg atggcaaaaa tattcgaatg tatcagcgac    960
tctataccgt tcacttgcac atatgccatg aatcaatca gatgttgatg agaatgcagc   1020
tgttcttgca tataatggac aactatggaa tcaaagctt ttgcatcaag tcaaattgaa   1080
tgcggtaaag tattataagt gttttgtcca actatgata cagttcttca gatatggaga   1140
acacttcgtg ccactcgaga tgccgcattt tcagttcgtg aacaagccgg acacactttg   1200
aaattctcgt tggagaatgc tgtagctgtt gatacaagag atagacctat tcttgcaagt   1260
cgtggaattc ttggtaagag taacaacgac tattttaaaa aaatatcttt ttcgaaaaaa   1320
ttacgaacga aaaaaactg tattatgtac ccaaacgcga aattttgcag ttcttgcgcg   1380
ttcttgttga taaaaatat gtaaaaaatt ggaaaaacta cgaaaagtcg ataaaaattc   1440
cgtaccaacc ggaaaatgtt tcattaattt ctcttccttt tttcagctcg ttttgctcaa   1500
gagtacgcag gagtatttgg tgatgcgtca tttgtgaaga atacattaga tttacaggta   1560
acaaccttat ttcaacaatt atttcaaatt ctattaaaaa taattccagg cagctgcccc   1620
tcttccactc ggtttcattc ttgccgcctc attccaagcg aaacatttga aaggactcgg   1680
agatcgagaa gttcatattt tggatagatg ttatttgggt ggacaacagg atgttcgagg   1740
atttggtctg aatactattg gagtgagttt taacgaaatt ctcttgaaag tcaaataatc   1800
attttcaggt taaagcagat aacagttgtc ttggaggagg tgcttcactt gctggtgtcg   1860
ttcatttgta tcggccattg attccaccaa atatgctatt tgcacacgca ttccttgcat   1920
ctggaagtgt tgcatcagtt cattccaaaa atttggtgca acaattacag gatactcaac   1980
gagtatcagc cggatttggt gagtttgaaa tttaggaaac atttggatga atgtattttt   2040
ttaaaaatag atcagcttta tttatttgaa aaaaacgct cattaatcaa tagtgatagt   2100
tccattctga gtttcttctt cttcctcgcg gaatacaatt tttgacttgt tcgcatcctt   2160
cttgtgtact ttgtcaccaa tcttctcatc aactaaatct cgaaactgaa aaaatttcaa   2220
aattattcca aaaaatattg atgcagacta ccttttttgat ggcttctggt acgtttctag   2280
cgtcgaatgg attggctcct ccaataatta agtctcgtt cggtagttta gccagacgga   2340
cggtgtgctt caacattttt ctaattaatc tatttcaatt caagtcactc actctctctt   2400
gacgtcttct tctatattcc aagaactctg cagaaaatcc gtgtccgcct tgtgtgtttc   2460
tagttggcgt cggaggattc acgggtccaa gacgaatgga tgtctaaaaa atgttatatt   2520
tttgcataaa gaaaacacca taccttcacc acttttgag ttgtgggcgt tctgaatgga   2580
attgatcgat tattattgct cttcttgat ttgcttctat cagctgcgta atgaggtgtt   2640
ctaaagatca gctttaattc atttggacaa gtgctcctct aataaactta ccctgtactc   2700
attttttgaaa cgatttacga tgataagatt gaaagtggaa gttaaattta gtctttcaaa   2760
gttgaaataa atcttcata aataaataaa tttaaatgaa agattaaata aattaacgtt   2820
cacgtagtta aaaaaataat ttaaatctta aacttctaat aaaaaatctc aattttccag   2880
gactcgcatt cgtgttcaaa agtattttcc ggctggaact caactacacg tatccattga   2940
aatatgtgct cggcgattca ttgctcggtg gattccatat tggagctggt gtcaacttct   3000
tgtagagatt aattggatgc aagcaccct caaaaagatt tttttgaaaa acgataaatt   3060
```

```
cacagaattt cagttctttt tctcccccctt ttattgttat tttcatcgta atgctgtgct    3120
agaagtcaga gtaaatatga gttttttttgt gttctaggaa ttccattttt tcaggaagca    3180
aatttaataa aaattatcga atttcttgct ctaaagatgt tgtacatttt atggaaatgt    3240
tcgtatagta a                                                         3251
```

<210> SEQ ID NO 76
<211> LENGTH: 1200
<212> TYPE: DNA
<213> ORGANISM: C. elegans

<400> SEQUENCE: 76

```
ttcgaacact ttatatttct cgttttaaaa ctgtcggtgt tttatagtaa actatcttca      60 gaaaaaatg agcctacgaa aaatcaattt cgtaactgga acgtgaaga agcttgaaga      120 agtcaaggct atttttgaaga atttcgaggt aaaatatatt tgatattatt cgaacgcgaa   180
attttgcgcc aaaagtacga tgcctggtct caacacgaca atattttgtt aaatacaaac    240
gaatgtgcgc cttcaaagaa aagtttcaat cttttcgttgc cgtggagata tttttagagt   300
ttttgtttaa attatatatt tgtcgtatcg aaaccgggta ccgtaatcaa tcaattaaat    360
attttcaggt ttcaaacgtg gatgtcgatt tggatgaatt ccaaggagaa cccgaattta    420
ttgccgaaag aaagtgccgt gaggctgttg aagctgtaaa agggcccgtt ttggtatgga    480
aaattgtatt tgttctaaaa attgtcaaat ttcaggtcga agacacaagt ttatgcttca    540
acgcaatggg cggtcttcct ggaccttata tcaagtggtt tttgaagaat ttgaaaccag    600
aaggactaca taatatgcta ggtaaatatt ttaattttttt gaaaaaactt attttttcagc   660 cggatttttct gacaaaaccg cctatgctca atgcatcttt gcgtacactg aaggactcgg    720
aaaacctatt catgtatttg ctggtatgat tttttgaatt taattcttta attttatatg     780
ttaatttagt tgtttcattc ctcaatttat gagagattt tttttcaatt tttctatttc     840
aggaaaatgt cctggtcaaa ttgttgctcc acgtggtgat actgcttttg gatgggatcc     900
atgcttccag ccagatggtt ttaaagaaac attcggagaa atggataaag atgtaaaaaa     960
tgaaatttct catcgtgcaa aggctctgga actcctcaag gaatattttc agaataatta    1020
aattattttt tctcatctat gcaatttctt gaaaatttgt taagtttccg ttgttatgca    1080
tttgctttta tttaaaaaaa aaagaatatt tttacattaa tattagatat gagaaaagag    1140
taatttctgg attttaacct tcctacaaaa gaatatttat attttttgta tgatttttta    1200
```

<210> SEQ ID NO 77
<211> LENGTH: 184
<212> TYPE: PRT
<213> ORGANISM: C. elegans

<400> SEQUENCE: 77

```
Met Ser Leu Arg Lys Ile Asn Phe Val Thr Gly Asn Val Lys Lys Leu
1               5                   10                  15

Glu Glu Val Lys Ala Ile Leu Lys Asn Phe Glu Val Ser Asn Val Asp
            20                  25                  30

Val Asp Leu Asp Glu Phe Gln Gly Glu Pro Glu Phe Ile Ala Glu Arg
        35                  40                  45

Lys Cys Arg Glu Ala Val Glu Ala Val Lys Gly Pro Val Leu Val Glu
    50                  55                  60

Asp Thr Ser Leu Cys Phe Asn Ala Met Gly Gly Leu Pro Gly Pro Tyr
65                  70                  75                  80
```

-continued

```
Ile Lys Trp Phe Leu Lys Asn Leu Lys Pro Glu Gly Leu His Asn Met
             85                  90                  95

Leu Ala Gly Phe Ser Asp Lys Thr Ala Tyr Ala Gln Cys Ile Phe Ala
            100                 105                 110

Tyr Thr Glu Gly Leu Gly Lys Pro Ile His Val Phe Ala Gly Lys Cys
        115                 120                 125

Pro Gly Gln Ile Val Ala Pro Arg Gly Asp Thr Ala Phe Gly Trp Asp
        130                 135                 140

Pro Cys Phe Gln Pro Asp Gly Phe Lys Glu Thr Phe Gly Glu Met Asp
145                 150                 155                 160

Lys Asp Val Lys Asn Glu Ile Ser His Arg Ala Lys Ala Leu Glu Leu
                165                 170                 175

Leu Lys Glu Tyr Phe Gln Asn Asn
            180
```

What is claimed is:

1. An isolated polynucleotide comprising a nucleotide sequence of SEQ ID NO:3, or the complete complement thereof.

2. An isolated polynucleotide that encodes a polypeptide comprising:
   (i) the amino acid sequence encoded by the nucleotide sequence of SEQ ID NO:3, or
   (ii) the amino acid sequence of SEQ ID NO: 63; or the complete complement of said polynucleotide.

3. The polynucleotide of claim 1 or 2 further comprising one or more nucleic acid sequences encoding a heterologous polypeptide.

4. The polynucleotide of claim 3 wherein the heterologous polypeptide is green fluorescent protein (GFP).

5. A vector comprising the polynucleotide of claim 1 or 2.

6. The vector of claim 5 that is an expression vector.

7. An isolated host cell which comprises the vector of claim 5.

8. An isolated host cell which comprises the vector of claim 6.

* * * * *